(12) United States Patent
Puskas et al.

(10) Patent No.: US 8,710,156 B2
(45) Date of Patent: Apr. 29, 2014

(54) PROCESS OF PREPARING FUNCTIONALIZED POLYMERS VIA ENZYMATIC CATALYSIS

(76) Inventors: Judit E. Puskas, Akron, OH (US); Mustafa Yasin Sen, Akron, OH (US)

( * ) Notice: Subject to any disclaimer, the term of this patent is extended or adjusted under 35 U.S.C. 154(b) by 197 days.

(21) Appl. No.: 12/732,467

(22) Filed: Mar. 26, 2010

(65) Prior Publication Data
US 2010/0240837 A1 Sep. 23, 2010

Related U.S. Application Data

(63) Continuation-in-part of application No. PCT/US2008/077777, filed on Sep. 26, 2008.

(60) Provisional application No. 60/975,625, filed on Sep. 27, 2007, provisional application No. 61/040,395, filed on Mar. 28, 2008.

(51) Int. Cl.
*C08G 77/38* (2006.01)
*C08G 65/332* (2006.01)
*C08G 65/333* (2006.01)
*C08L 71/02* (2006.01)

(52) U.S. Cl.
CPC ...... *C08G 65/3322* (2013.01); *C08G 65/33317* (2013.01); *C08G 65/33303* (2013.01); *C08G 2650/50* (2013.01); *C08L 71/02* (2013.01)
USPC .............. 525/386; 525/233; 525/8; 525/54.1; 525/375; 525/379; 562/517; 562/524; 562/509; 526/320; 435/128; 435/197; 435/132; 435/135; 435/227

(58) Field of Classification Search
CPC ................ C08G 65/3322; C08G 65/33317; C08G 65/33303; C08G 2650/50; C08L 71/02
USPC ........... 560/517, 524, 209; 522/181; 526/320; 525/233, 8, 54.1, 348, 379, 386; 435/128, 197, 132, 135, 227; 562/517, 562/524, 95
See application file for complete search history.

(56) References Cited

U.S. PATENT DOCUMENTS 6,268,521 B1 * 7/2001 Gruning et al. ............... 560/209
(Continued)

FOREIGN PATENT DOCUMENTS

WO   WO 2006111566 A2 * 10/2006 ............. C12P 13/02

OTHER PUBLICATIONS

Cordova Biomacromolecules 2001, 2, 1347-13-51.*
(Continued)

*Primary Examiner* — Mark Kaucher
(74) *Attorney, Agent, or Firm* — Renner Kenner Greive Bobak Taylor & Weber

(57) ABSTRACT

The invention relates to functionalized, telechelic polymers synthesized by enzymatic catalysis and methods, and the functionalization of polymers via Michael addition with a lipase catalyst, and the crosslinking of mono- or difunctional (telechelic) polymers made by enzymatic catalysis, such as by using multifunctional coupling agents and enzyme catalysts. Quantitative transesterification of vinyl methacrylate with poly(ethylene glycol), poly(isobutylene) and poly(dimethylsiloxane) was achieved using *Candida antarctica* lipase B. In addition, methacrylate-functionalized poly(ethylene glycol) monomethyl ether has been successfully coupled to aminoethoxy poly(ethylene glycol) monomethyl ether via Michael addition using *Candida antarctica* lipase B. Amine-functionalized poly(ethylene glycol)s have also been used for the preparation of poly(ethylene glycol)-based dendrimers and gels through Michael addition of the polymer onto triacryloyl hexahydro-triazine using the same enzyme. $^1$H and $^{13}$C NMR spectroscopy verified the structure of the functionalized polymers.

18 Claims, 56 Drawing Sheets

(56) References Cited

U.S. PATENT DOCUMENTS

2003/0168633 A1* 9/2003 Wellinghoff et al. .... 252/299.01
2006/0009589 A1* 1/2006 Haering et al. ........... 525/330.1
2008/0194767 A1* 8/2008 Haring et al. ................ 525/259
2010/0239659 A1* 9/2010 Diwan et al. .................. 424/451

OTHER PUBLICATIONS

Cai Biotechnology Letters 2004, 26, 525-528.*

* cited by examiner

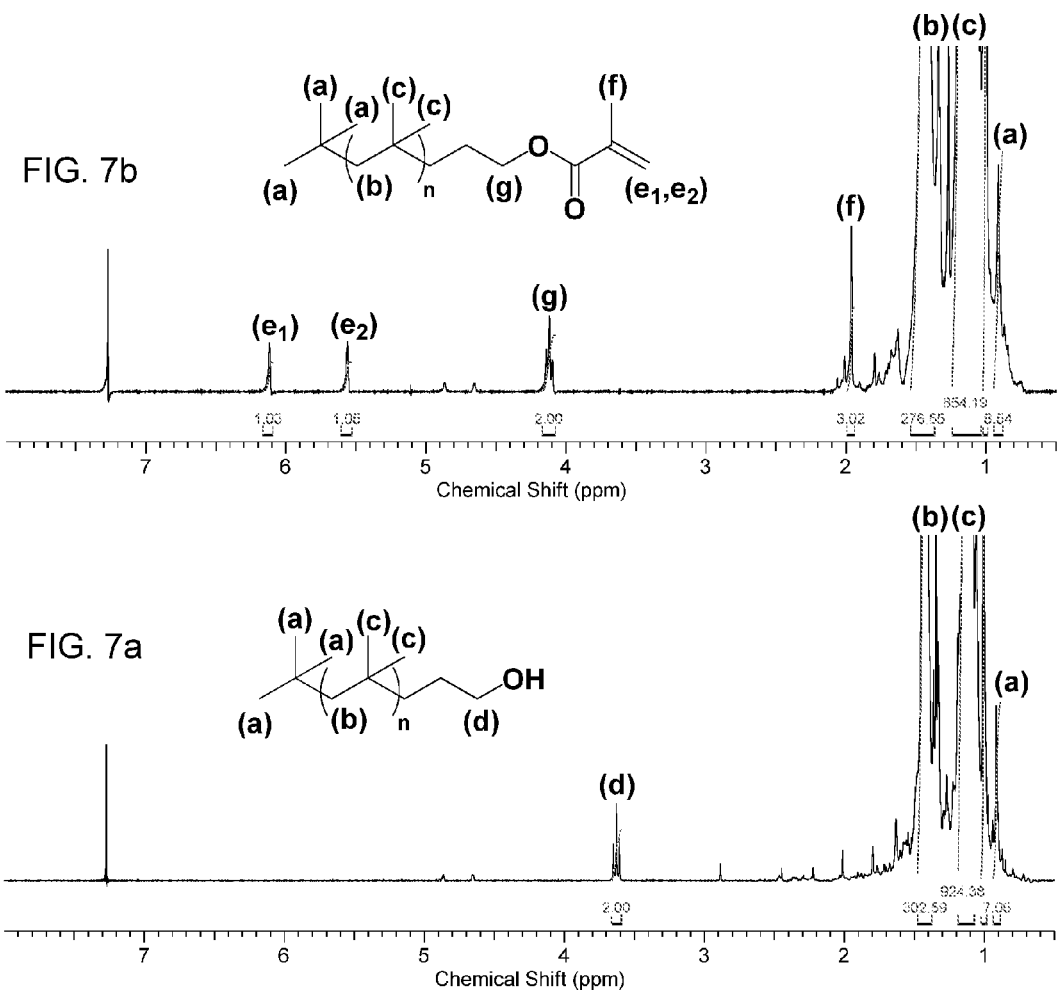

FIG. 34a
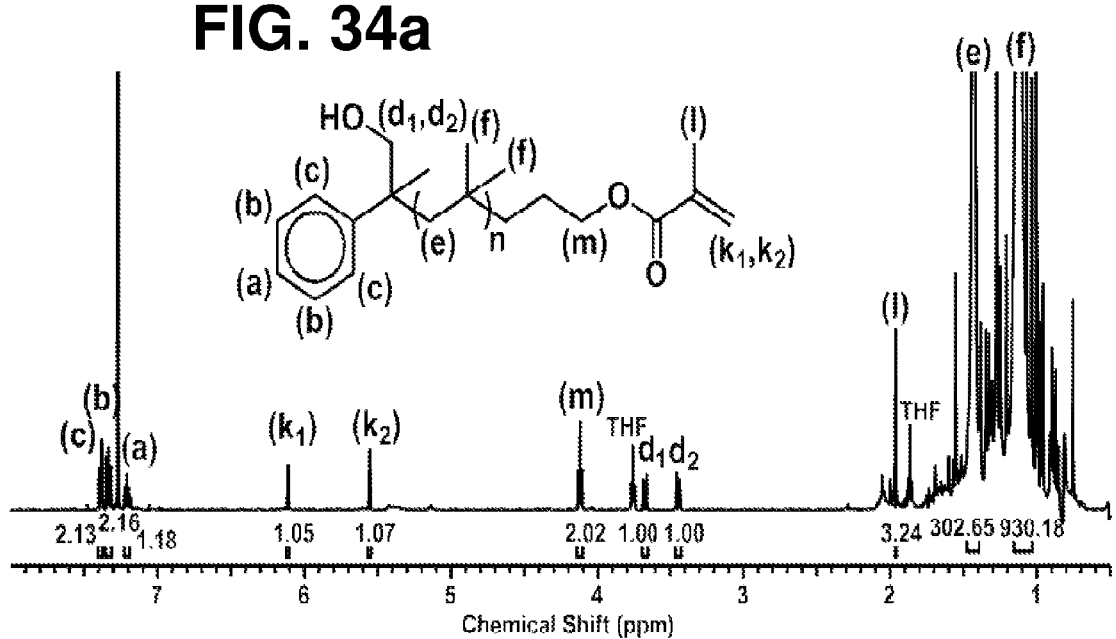
FIG. 34b
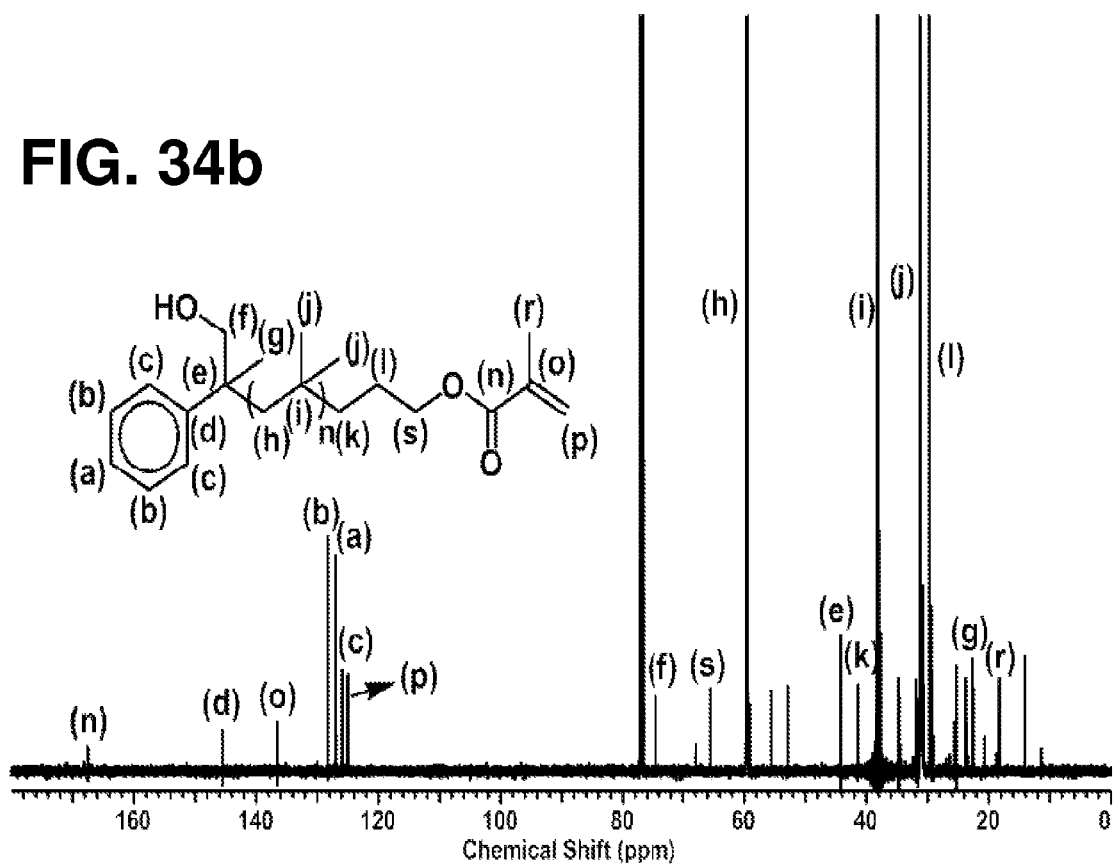
FIG. 34

PROCESS OF PREPARING FUNCTIONALIZED POLYMERS VIA ENZYMATIC CATALYSIS

CROSS REFERENCE TO RELATED APPLICATION

This U.S. patent application is a continuation-in-part (CIP) application of PCT International Application No. PCT/US08/77777, filed Sep. 26, 2008, which claims priority to U.S. Provisional Patent Application Ser. Nos. 61/040,395 filed on Mar. 28, 2008 and 60/975,625 filed on Sep. 27, 2007, which are hereby incorporated by reference in their entirety.

TECHNICAL FIELD

The invention relates to methods of functionalizing polymers via enzymatic catalysis, and the polymer materials produced thereby. More particularly, the invention relates to methods of preparing functionalized polymers via a transesterification process with a catalyst. In examples, the invention relates to a method of preparing functionalized glycol ethers, functionalized polyisobutylenes and functionalized polysiloxanes via a transesterification process with a lipase catalyst. In other examples, the invention relates to functionalization of polymers via Michael addition with a lipase catalyst, and the crosslinking of mono- or difunctional (telechelic) polymers made by enzymatic catalysis as outlined in this invention, using multifunctional coupling agents and enzyme catalysts.

BACKGROUND OF THE INVENTION

The modification of natural or synthetic polymers with enzymes is an environmentally friendly alternative to classical chemical modification reactions which generally require harsh reaction conditions. Despite the advantage of using enzymes in functionalization reactions, i.e. milder reaction conditions and highly specific transformations, only a few examples have been reported in the literature involving either natural or synthetic polymers.

Mushroom tyrosinase has been used to introduce phenolic functionalities into chitosan. The synthetic pathway involved enzyme-catalyzed oxidation of phenol to an o-quinone which dissociated from the enzyme and freely diffused to the nucleophilic amine site of the chitosan polymer. In addition to the incorporation of quinone into the chitosan, subsequent polymerization of quinone into oligomeric phenols was also observed as determined by UV-Vis spectroscopy. The effectiveness of the reactions was not discussed. Polysaccharides have been functionalized with fatty acids by transesterification using ion-paired subtilisin Carlsberg protease in organic solvents. It has been observed that the enzyme selectively acylated the primary hydroxyl groups on polysaccharides and that the degrees of substitution per glucose moiety in amylose and β-cyclodextrin were 0.185 and 0.250, respectively. Lactose was attached to the hydroxyl groups of hydroxyethylcellulose (HEC) by transglycosylation in sodium acetate buffer using *Aspergillus oryzae*. Although the number of sites available in each HEC unit is 3, the maximum degree of substitution obtained by this method was only 0.033. The same natural polymer, HEC, has recently been modified by enzymatic transesterification with both vinyl propionate and vinyl acrylate in the presence of subtilisin Carlsberg in anhydrous pyridine. These biotransformations of cellulose were promising; however, low conversions limited their viability. It has been reported that the phosphorylation of cotton cellulose using bakers' yeast hexokinase as the enzyme and ATP as the phosphoryl donor. The phosphorylation of 0.03% of the glycopyranose units in the cellulose resulted in improved dyeability and flame resistance. All of the examples listed here were hindered by low conversion.

Even fewer examples have been reported for synthetic polymer functionalization using enzymatic catalysis, which are also characterized by low conversion. For instance, 16% of the pendant nitrile groups of polyacrylonitrile fibers were converted to the corresponding amides by a nitrile hydratase enzyme, resulting in a significant increase in the hydrophilicity of the fiber surface. Mushroom tyrosinase has been utilized to graft poly(4-hydroxystyrene) (PHS) onto chitosan. In this approach, first 1-2% of the phenolic moieties of PHS were enzymatically oxidized and then the resulting polymer was reacted with the amine groups of chitosan. Lipase-catalyzed acylation of poly[N-(2-hydroxypropyl)-11-methacryloylaminoundecanamide-co-styrene] and the corresponding monomer with vinyl acetate, phenyl acetate, 4-fluorophenyl acetate and phenyl stearate has been reported. $^1$H NMR results revealed that the reactivity of the monomer was higher than that of the copolymer and that the copolymer could be acylated with up to 40% conversion. In addition, it was found that the reactivity of copolymer was dependent on copolymer composition which indicated the effect of steric hindrance and hydrophobicity on reaction kinetics. The synthesis of organosilicon carbohydrate macromers by *Candida antarctica* lipase B catalyzed esterification has been reported. Diacid-endblocked siloxanes were reacted with α,β-ethyl glucoside under vacuum in bulk. Esterification occurred with high regioselectivity (>98%) at the primary hydroxyl (C6) of the glucoside, but electrospray ionization mass spectrometry (ESI MS) showed the presence of a mixture of mono- and diesters.

The preparation of polyolefin-based telechelic polymers, such as methacrylate-terminated polyisobutylenes (PIB-MAs), has been shown in the prior art by a variety of strategies. In one example, PIB-Cl$^t$ prepared by the inifer technique was first converted to the corresponding exo-olefin by dehydrochlorination with t-BuOK, followed by hydroboration/oxidation to yield PIB-OH which was subsequently converted to PIB-MA by acylation with methacryloyl chloride. In another process, PIB-OH was synthesized by hydroboration/oxidation of allyl-terminated PIB, prepared by end-quenching of living PIB$^+$ with allyltrimethylsilane, and the latter was converted to PIB-MA with methacryloyl chloride. A further process describes how PIB-MA was synthesized by nucleophilic substitution of PIB-CH$_2$—CH$_2$—CH$_2$—Br (prepared by anti-Markovnikov hydrobromination of allyl-terminated PIB) with sodium methacrylate. This same method was also applied to Glissopal®2300, a commercially available PIB with olefinic end groups. Quantitative syntheses of primary hydroxyl terminated PIB and Glissopal-OH has also been described.

Notwithstanding the state of the art as described herein, there is a need for further improvements in the preparation of functionalized polymers (monofunctional or difunctional (telechelic) polymers) via enzymatic catalysis which is an environmentally friendly method when compared with toxic acylating agents such as methacryloyl chloride, and catalysts; and is useful in biomaterials prepared from these functionalized polymers.

SUMMARY OF THE INVENTION

The invention provides methods and functionalized polymers that are prepared through enzymatic catalysis, and the polymer materials produced thereby. The materials produced according to the invention may be useful for biomaterials, due to the absence of potentially toxic catalyst metal residues. In one embodiment of the invention, the functionalized polymer is prepared by reacting a polymer and at least one acyl donor in the presence of an effective amount of an enzymatic catalyst in a transesterification reaction. Other functionalized polymers may be prepared from other chemical reactions, such as epoxidation, Michael addition, hydrolysis, or other techniques, through enzymatic catalysis.

In another embodiment of the invention, poly(ethylene glycol) is transesterified with at least one ester in the presence of an effective amount of a lipase to form a functionalized, telechelic polymer.

Furthermore, the invention provides methods of preparing a telechelic polymer through enzymatic catalysis. The method includes the steps of reacting a glycol ether, such as poly(ethylene) glycol, with at least one ester in the presence of an effective amount of a lipase in a transesterification reaction.

The invention also provides methods and functionalized polyolefin-based polymers that are prepared through enzymatic catalysis, and the polymer materials produced thereby. In one embodiment of the invention, the functionalized polymer is prepared by reacting a polyolefin-based polymer and at least one acyl donor in the presence of an effective amount of an enzymatic catalyst in a transesterification reaction. Other functionalized polymers may be prepared from other chemical reactions, such as epoxidation, Michael addition, hydrolysis, or other techniques, through enzymatic catalysis.

In another embodiment of the invention, hydroxyl-functionalized polyisobutylene is transesterified with at least one ester in the presence of an effective amount of a lipase to form mono- or difunctionalized (telechelic) polymer.

In yet another embodiment of the invention, a block copolymer is prepared. The method of preparing the block copolymer through enzymatic catalysis includes the steps of reacting a methacrylate functionalized polymer prepared by enzymatic transesterification with another polymer bearing amine functionality in the presence of an effective amount of an enzyme catalyst via Michael addition reaction.

In still yet another embodiment of the invention, a dendrimer is prepared. The method of preparing the dendrimer includes the steps of reacting a polyether diamine with a functionalized nitrogen heterocycle in the presence of an effective amount of the enzyme catalyst. Depending on the stoichiometry of the reaction, a polymer gel will be formed.

In another embodiment of the invention, another dendrimer is prepared. The method of preparing the dendrimer includes the steps of reacting an aminoethoxy glycol ether with a functionalized nitrogen heterocycle in the presence of an effective amount of the enzyme catalyst.

Various other examples of the invention are also set forth. These include for example, preparation of thymine-functionalized PEG by transesterification processes, regioselective enzymatic methacrylation of functionalized PIBs, methacrylation of primary hydroxyl-functionalized polystyrene possessing a spacer, transesterification of vinyl acrylate with HO-PEG-OH, transesterification of vinyl methacrylate with HO-PEG-OH, transesterification of vinyl crotonate with OH-PEG-OH, transesterification of divinyl adipate with MPEG-OH, synthesis of $(HO)_2$-PEG-$(OH)_2$ as a dendrimer core and other examples.

BRIEF DESCRIPTION OF THE DRAWINGS

FIGS. 7a and 7b are the $^1$H NMR spectra of polyisobutylene before and after methacrylation;

FIG. 34 shows the (a) NMR spectra of the methacrylation product of HO-PIB-$CH_2$—$CH_2$—$CH_2$—OH: (a) $^1$H NMR spectrum and (b) $^{13}$C NMR spectrum (solvent: $CDCl_3$).

DETAILED DESCRIPTION OF THE INVENTION

Figure 1:
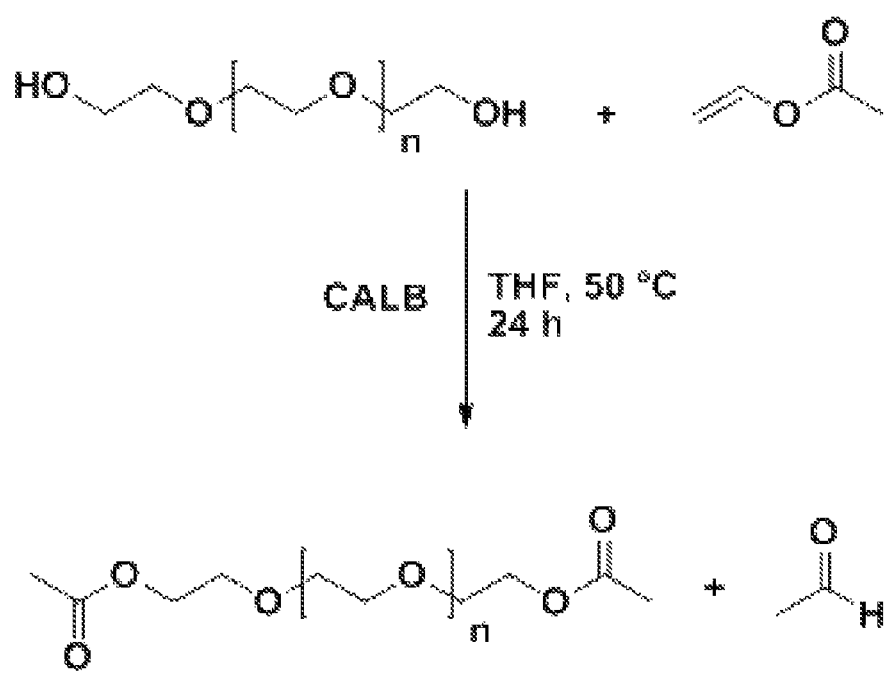
FIG. 1 illustrates the scheme of the transesterification of vinyl acetate with poly(ethylene glycol)

An example of the invention relates to methods of preparing functionalized polymers through enzymatic catalysis. In an example of the invention, the functionalized polymer is prepared by reacting a polyol with an ester and an effective amount of an enzymatic catalyst in a transesterification reaction. Other chemical reactions, such as epoxidation, Michael addition, hydrolysis, or other techniques, may also be used to prepare functionalized polymers through enzymatic catalysis.

In an embodiment of the invention the polyol includes, but is not limited to, unsaturated diols such as polybutadiene diol or saturated diols such as ethylene glycol, diethylene glycol, polyethylene glycol, aminoethoxy glycol ether, such as aminoethoxy polyethylene glycol monomethyl ether, polyethylene glycol monomethyl ether, propylene glycol, dipropylene glycol, polypropylene glycol, 2-methyl-1,3-propanediol, 1,2-, 1,3-, 1,4-, or 2,3-butanediols, 2-methyl-1,4-butanediol, 2,3-dimethyl-2,3-butanediol, 1,5-pentanediol, 1,6-hexanediol; unsaturated triols such as castor oil (i.e., triricinoleoyl glycerol); saturated triols such as 1,2,4-butanetriol, 1,2,6-hexanetriol, trimethylolethane (i.e., 1,1,1-tri(hydroxymethyl)ethane), trimethylolpropane (i.e., 2,2-di(hydroxymethyl)-1-butanol), triethanolamine, triisopropanolamine; unsaturated tetraols such as 2,4,6-tris(N-methyl-N-hydroxymethyl-aminomethyl)phenyl; saturated tetraols such as pentaerythritol (i.e., tetramethylolmethane), tetrahydroxypropylene ethylenediamine (i.e., N,N,N',N'-tetrakis(2-hydroxypropyl)-ethylenediamine); and other polyols such as mannitol (i.e., 1,2,3,4,5,6-hexanehexyl) and sorbitol.

Another embodiment of the invention relates to methods preparing functionalized polymers through enzymatic catalysis. In an example of the invention, the functionalized polymer is prepared by reacting a polyolefin or a polyolefin-derived material with an ester and an effective amount of an enzymatic catalyst in a transesterification reaction. Other chemical reactions, such as epoxidation, hydrolysis, or other techniques, may also be used to prepare functionalized polymers through enzymatic catalysis.

In another embodiment of the invention the polyolefin or polyolefin-derived material includes, but is not limited to, polychloroprene, polybutadiene, polyisoprene, polyisobutylene, polysiloxanes, such as polydimethylsiloxane, nitrile-butadiene rubber, styrene-butadiene rubber, chlorinated polyethylene, chlorosulfonated polyethylene, epichlorohydrin rubber, butyl rubber, or halobutyl rubber. The above-mentioned materials may be hydroxyl functionalized for use in preparing the functionalized polymer.

In yet a further embodiment of the invention, the acyl donor refers to a compound that is capable of leading to the formation of an ester in the presence of an enzymatic catalyst and a substrate. Examples of acyl donors include butyl acetate, ethyl phenyl acetate, ethyl acetate, ethyl trichloroacetate, ethyl trifluoroacetate, isopropenyl acetate, vinyl acetate, ethyl methoxy acetate, 2,2,2-trifluoroethyl butyrate, diketene, vinyl propionate and vinyl methacrylate.

In further embodiment of the invention, the enzymatic catalyst is capable of catalyzing a transesterification reaction. In particular the enzymatic catalyst is a lipase or an esterase. Examples of such lipases and esterases are *Candida cylindracea, Candida lipolytica, Candida rugosa, Candida antarctica, Candida utilis, Chromobacterium viscosum, Geotrichum viscosum, Geotrichum candidum, Mucor javanicus, Mucor mihei, pig pancreas, Pseudomonas* spp., *Pseudomonas fluorescens, Pseudomonas cepacia, Rhizopus arrhizus, Rhizopus delemar, Rhizopus niveus, Rhizopus oryzae, Aspergillus niger, Penicillium roquefortii, Penicillium camembertii* or esterases of *Bacillus* spp. and *Bacillus thermoglucosidasius*. Amanolipase was also found to work in catalyzing Michael addition. The enzymes mentioned are commercially available, for example from Novozymes Biotech Inc., Denmark.

Materials, Methods and Characterization

Materials

*Candida antarctica* lipase B (CALB) immobilized on macroporous polyacrylic resin beads (Novozyme 435; Aldrich), Amano lipase M from *Mucor javanicus* (Aldrich), poly(ethylene glycol) ($M_n$=2000, 4600, 10,000 g/mol, broad molecular weight distribution MWD, Aldrich; and $M_n$=1000, 10,100 g/mol, $M_w/M_n$<1.1, American Polymer Standards Corp.), Ω-ω-diamino terminated poly(ethylene glycol) ($M_n$=2,000 g/mol, $M_w/M_n$<1.1, Polymer Source Inc.), ω-amino terminated poly(ethylene glycol) monomethyl ether ($M_n$=2,000 g/mol, $M_w/M_n$<1.1, Polymer Source Inc.), polyethylene glycol monomethyl ether ($M_n$=2,000 g/mol, broad MWD, Aldrich) silanol-terminated poly(dimethyl siloxane) ($M_n$=3,300 g/mol, Aldrich), monocarbinol-terminated poly(dimethyl siloxane) ($M_n$=5,000 g/mol, Gelest), vinyl methacrylate (98%, Alfa Aesar), vinyl acrylate (>90%, Monomer-Polymer & Dajac Labs), divinyl adipate (>98%, TCI America), vinyl crotonate (>99%, TCI America), thymine (99%, Aldrich), triethylamine (≥99.5%, Aldrich) and folic acid (98%, Aldrich) were used as received. Tetrahydrofuran (Fischer Scientific) and hexane (Fisher Scientific) were distilled over sodium benzophenone (Aldrich) and vinyl acetate (≥99%, Aldrich) was distilled from calcium chloride (Aldrich) prior to use.

Glissopal®2300 (nominal $M_n$=2,145 g/mol, $M_w/M_n$=1.98) was obtained courtesy of BASF. Primary hydroxyl-functionalized PIBs (PIB-OH and Glissopal-OH) were prepared as described in S. Ummadisetty, J. P. Kennedy *J. Polym. Sci. Part A Polym. Chem.* 2008, 46, 4236.

Characterization $^1$H and $^{13}$C NMR spectra were recorded on a Varian Mercury-300 NMR or a Varian NMRS 500 spectrometer. Deuterated chloroform (Chemical Isotope Laboratories, 99.8% CDCl$_3$) and dimethyl sulfoxide-d$_6$ [Chemical Isotope Laboratories, (D, 99.9%)] were used as the solvents. The resonances of non-deuterated chloroform at δ7.27 ppm and δ77.23 ppm were internal references for the $^1$H and $^{13}$C NMR spectra, respectively; and the resonances of non-deuterated dimethyl sulfoxide peaks at δ2.5 ppm and δ39.51 ppm were used as internal reference for $^1$H and $^{13}$C NMR spectra respectively. The molecular weight (MW) and molecular weight distribution (MWD) of the PEGs and PIBs before and after acylation or methacrylation were determined by size exclusion chromatography (SEC) using two different SEC set-up. The first system consisted of a Waters 515 HPLC pump, a Waters 2487 Dual Absorbance UV Detector, a Wyatt OPTILAB DSP Interferometric Refractometer, a Wyatt DAWN EOS multi-angle light scattering detector, a Wyatt ViscoStar viscometer, a Wyatt QELS quasi-elastic light scattering instrument, a Waters 717 plus autosampler and 6 Styragel® columns (HR0.5, HR1, HR3, HR4, HR5 and H6). The RI detector and the columns were thermostated at 35° C. and THF freshly distilled from $CaH_2$ was used as the mobile phase at a flow rate of 1 mL/min. The second set-up was a Waters 150C-Plus system equipped with a Waters 410 differential refractometer, a Wyatt DAWN EOS light scattering detector and 3 Styragel® columns (HR1, HR4E and HR5E) thermostated at 35° C., with THF as the mobile phase at a flow rate of 1 mL/min. The results were analyzed using the ASTRA software (Wyatt Technology) with dn/dc (specific refractive index increment)=0.068 and 0.108 for PEG and PIB respectively, and assuming 100% mass recovery.

In the foregoing examples, the MALDI-ToF mass spectra were acquired on a Bruker Ultraflex-III ToF/ToF mass spectrometer (Bruker Daltonics, Inc., Billerica, Mass.) equipped with a Nd:YAG laser (355 nm). All spectra were measured in positive reflector mode. The instrument was calibrated prior to each measurement with an external PMMA standard. For example, individual solutions of PEG dimethacrylate (10 mg/mL), 1,8,9-trihydroxyanthracene (dithranol, 20 mg/mL, 97%, Alfa Aesar), and sodium trifluoroacetate (NaTFA, 10 mg/mL) in anhydrous THF were mixed in the ratio of polymer:matrix:cationizing salt (1:10:2), and 0.5 µL of the resulting mixture were deposited on microtiter plate wells (MTP 384-well ground steel plate). After evaporation of the solvent, the plate was inserted into the MALDI source. The attenuation of the Nd:YAG laser was adjusted to minimize unwanted polymer fragmentation and to maximize the sensitivity.

Transesterification Method

In the transesterification method, an ester was reacted with the polyol in the presence of an effective amount of the enzyme catalyst. In one embodiment of the invention, the ester is vinylacetate, vinyl methacrylate or combination thereof. In another embodiment of the invention, the polyol is poly(ethylene glycol). In yet a further embodiment of the invention, the enzyme catalyst is a lipase, wherein the lipase is CALB. In particular, the transesterification method proceeded when about 3 equivalents of an ester, vinyl acetate (about 0.11 mL, 1.2 mmol) or vinyl methacrylate (about 0.14 mL, 1.2 mmol), was reacted with poly(ethylene glycol) (about 0.2 g, 0.2 mmol) in THF (about 4.5 mL) in the presence of CALB (about 10 mg/mL), and the reaction mixture was stirred at about 300 rpm for 24 hours at about 50° C. After the reaction, the mixture was filtered to remove the enzyme. THF, unreacted vinyl acetate and the by-product acetaldehyde were removed by a rotary evaporator and the polymer was dried in a vacuum oven at room temperature for about 24 hours. The methacrylate-functionalized polymer was precipitated into hexane after filtering off the enzyme, and dried in a vacuum oven at room temperature for about 24 hours.

For the transesterification reactions, vinyl acetate and vinyl methacrylate (VMA) were chosen as suitable acyl donors since they rendered the transesterification reaction substantially irreversible by forming an unstable enol, i.e. vinyl alcohol, which rapidly tautomerized to acetaldehyde. Among several lipases used in transesterification reactions CALB was found to be one of the most active and stable lipases. THF was used as the solvent due to its relatively low polarity, ability to maintain the catalytically active conformation of the enzyme, as well as being a good solvent for the polymer. Anhydrous conditions were employed to prevent possible hydrolysis; and the reaction was run at 50° C. because the optimum temperature range of enzyme stability is 40-60° C.

Figure 2:
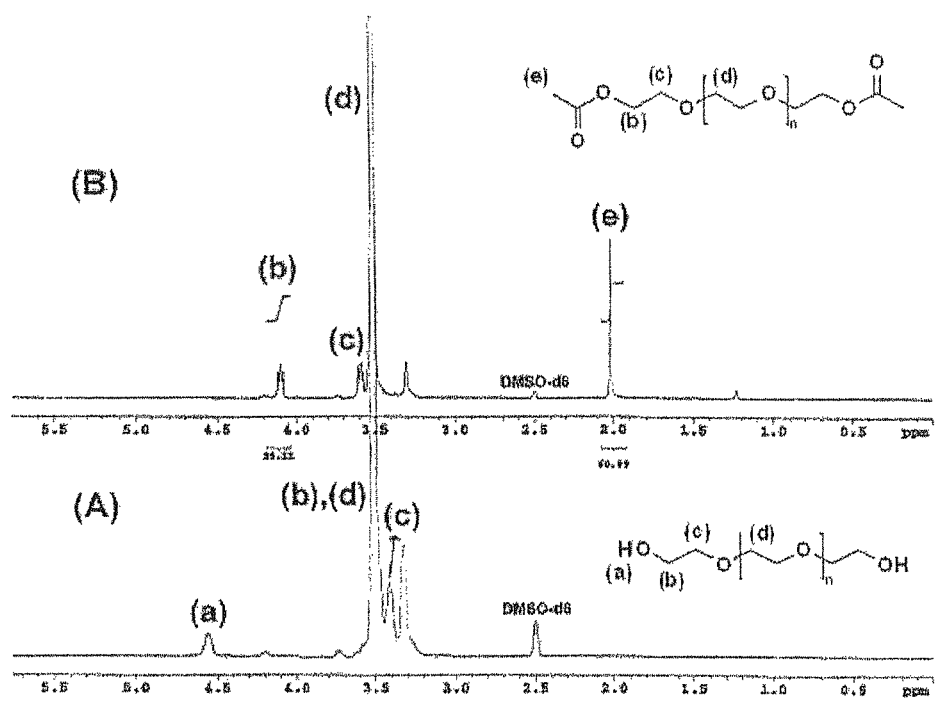
FIG. 2 is the $^1$H NMR spectra of PEG ($M_n$=1000 g/mol, $M_w/M_n$=1.06) before (A) and after (B) acylation.

It was determined that under the experimental conditions that were developed (FIG. 1) both narrow and broad MWD PEGs reacted quantitatively with vinyl acetate. The $^1$H NMR spectra of the PEG with $M_n$=1,000 g/mol, $M_w/M_n$=1.06) before and after acylation are shown in FIG. 2. The peak at δ4.6 ppm (a) attributed to the protons of the terminal hydroxyl groups of the polymer disappeared and new peaks corresponding to the methyl protons of the acyl end group and the methylene protons next to the ester bond at δ2.0 (e) and 4.1 ppm (b), respectively, were observed. From the integration ratio of the three methyl protons of the acyl end group (e) to two methylene protons adjacent to the acyl end group (b) the conversion was readily calculated as 100%. The reactions proceeded smoothly with all PEG samples, yielding α-ω telechelic PEG-acetates.

Figure 3B:
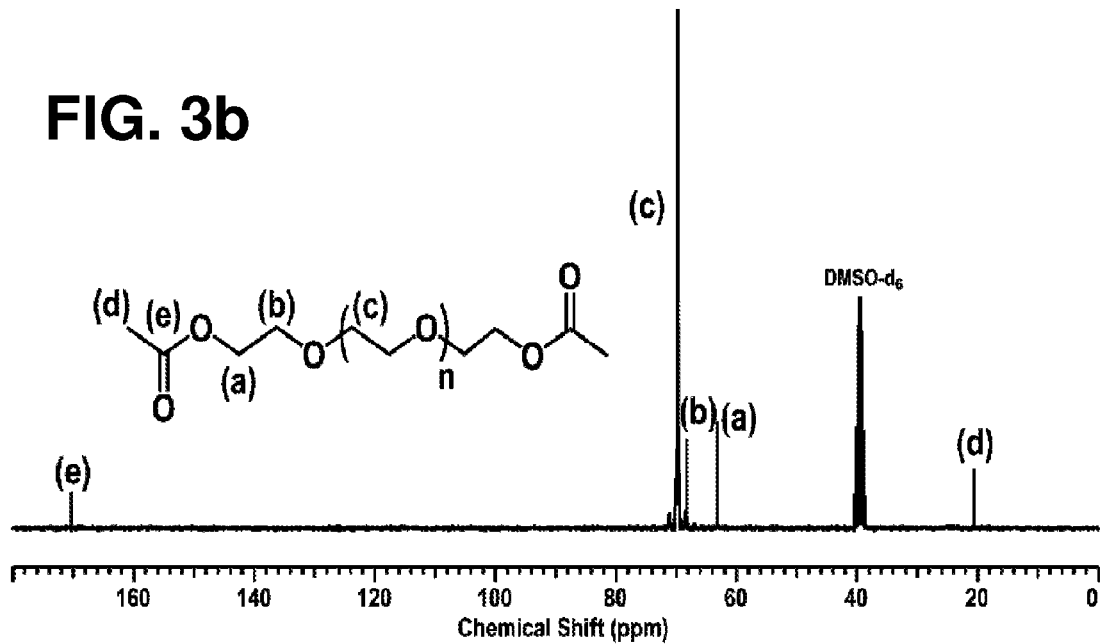
FIG. 3 is the $^{13}$C NMR spectra of PEG ($M_n$=1000 g/mol, $M_w/M_n$=1.06) before (A) and after (B) acylation.
Figure 3A:
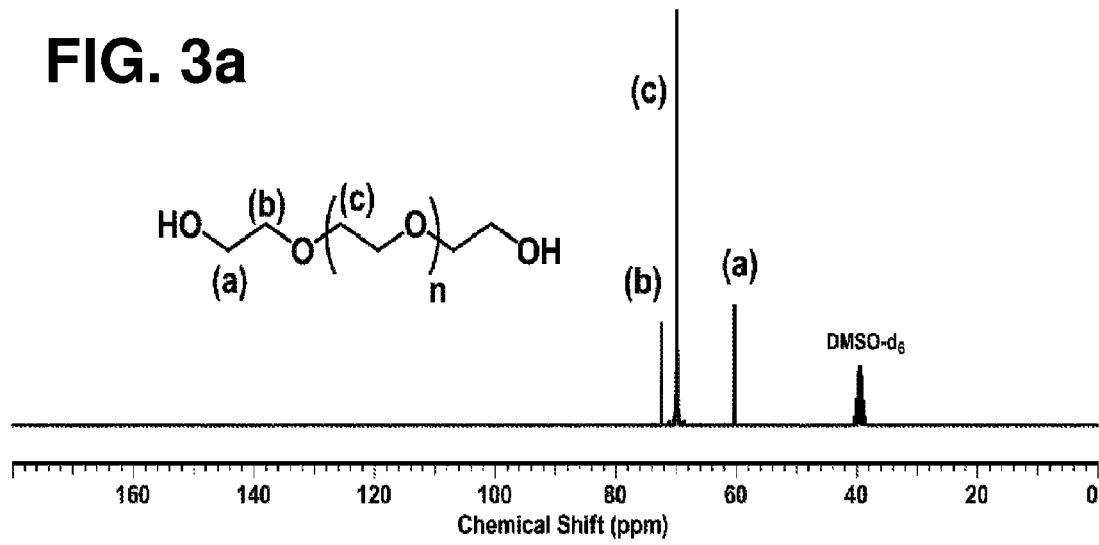

The $^{13}$C NMR spectrum corresponding to FIG. 2 is shown in FIG. 3. The carbons connected to the hydroxyl-end groups observed at δ60 ppm in the $^{13}$C NMR spectrum of the starting material disappeared after the reaction and the new resonances observed at δ20.8 and δ170.7 ppm were attributed to the methyl carbon and the carbonyl carbon of the acyl end group, respectively.

Figure 4:
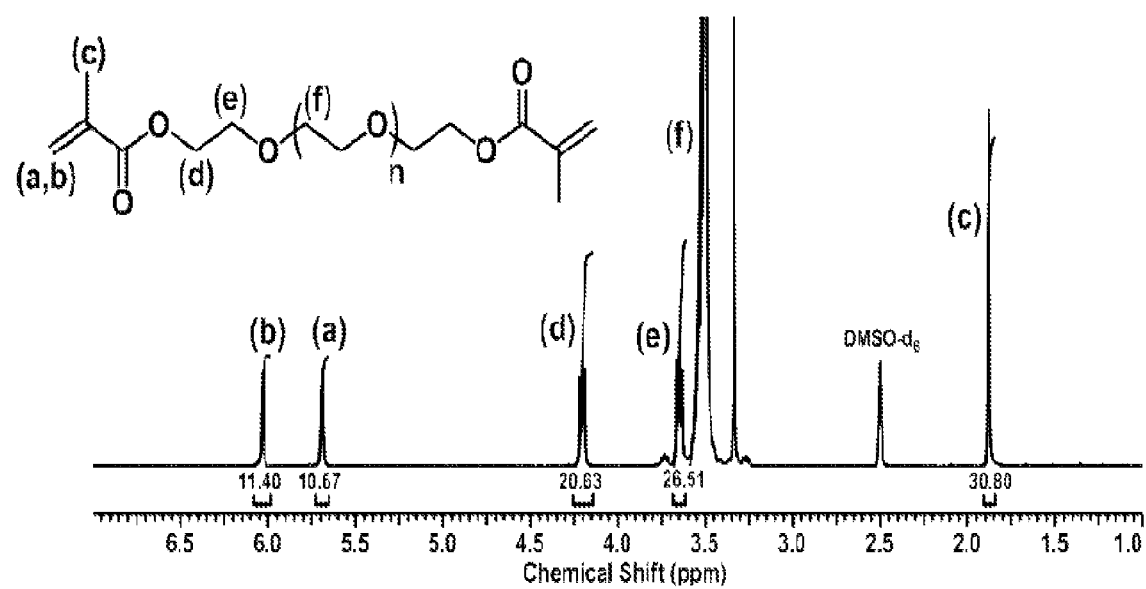
FIG. 4 is the $^1$H NMR spectrum of methacrylated-PEG ($M_n$=2000 g/mol, broad MWD)
Figure 5:
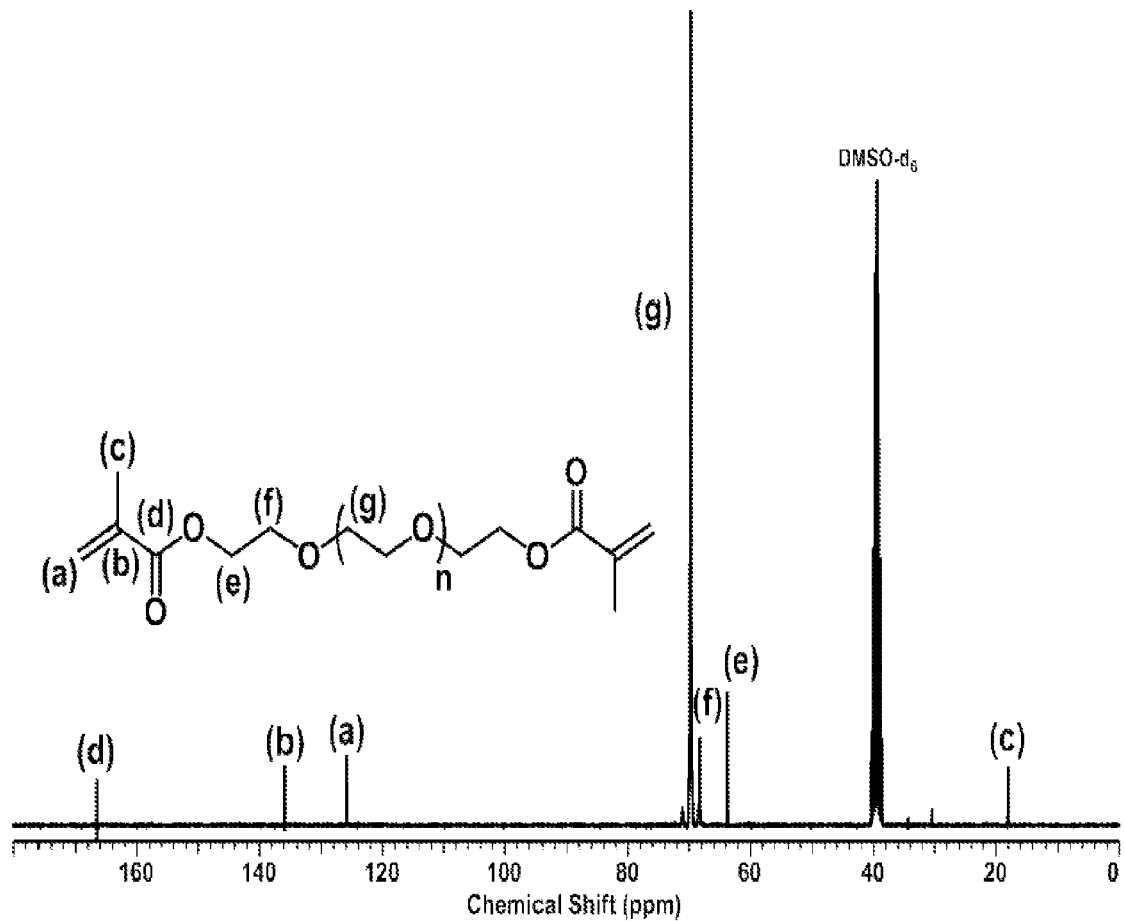
FIG. 5 is the $^{13}$C NMR spectrum of methacrylated-PEG ($M_n$=2000 g/mol, broad MWD)

Following the same strategy, poly(ethylene glycol) dimethacrylate was prepared using vinyl methacrylate as the ester. The $^1$H and $^{13}$C NMR spectra of a methacrylated poly (ethylene glycol) ($M_n$=2,000 g/mol, broad MWD) are shown in FIGS. 4 and 5, respectively. The integration ratios of the two vinylidene (δ5.7 (a) and δ6.0 (b)) and the three methyl δ1.9 (c) protons in the methacrylate groups, and the two methylene protons adjacent to the methacrylate end group (d) were 1:1:3:2 which indicated quantitative functionalization.

In the $^{13}$C NMR spectrum, similarly to the acyl-functionalized PEG, no peaks at δ60 ppm attributed to carbons adjacent to hydroxyl-end groups in the starting material were observed and the new resonances appeared at the expected positions confirming the structure of the product. All PEG samples reacted quantitatively, yielding α-ω telechelic PEG-methacrylates.

From the data presented herein, α-ω telechelic PEG-acetates and PEG-methacrylates were successfully synthesized and characterized. The synthetic strategy involved enzyme-catalyzed transesterification using vinyl esters which rendered the reactions irreversible.

In another embodiment of the invention, the transesterification method includes reacting an ester with a polyolefin in the presence of an effective amount of the enzyme catalyst. In one embodiment of the invention, the ester may be selected from vinyl acetate, vinyl methacrylate and combinations thereof. In another embodiment of the invention, the polyolefin is polyisobutylene. In yet a further embodiment of the invention, the enzyme catalyst is a lipase, wherein the lipase is CALB.

Figure 6:
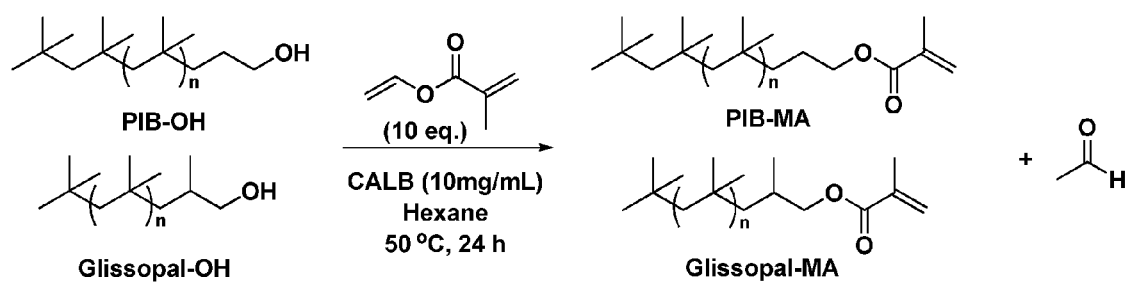
FIG. 6 illustrates the scheme of the transesterification of vinyl methacrylate with polyisobutylene.

In particular, the primary hydroxyl terminated PIB (PIB-OH) ($M_n$=5,240 g/mol and $M_1/M_w$=1.09) was enzymatically methacrylated according to the scheme as shown in FIG. 6. Hexane solvent was used since the catalytically active conformation of the enzyme is best maintained in low polarity solvents. The transesterification method proceeded with PIB-OH (about 0.4 g, 0.08 mmol) being placed in a 10 mL round bottom flask containing hexane (about 5 mL), CALB (about 10 mg/mL) and vinyl methacrylate (about 0.1 mL, 0.8 mmol). The flask was sealed with a septum and purged with nitrogen. The resulting solution was stirred at 300 rpm for 24 hours at 50° C. After filtering off the enzyme, the polymer was precipitated into methanol and dried in vacuum for 24 hours at room temperature (yield: about 0.25 g, conversion: ~100%).

The $^1$H NMR spectrum of the PIB before, as seen in FIG. 7a, and after, as seen in FIG. 7b, methacrylation are provided. The resonance at δ3.6 ppm, corresponding to the —$CH_2$— protons next to the hydroxyl group, as seen in FIG. 7a, disappeared and new resonances attributed to the vinylidene

[δ5.6 (e$_2$), δ6.1 (e$_1$)], methyl [δ2.0 (f)] and methylene protons adjacent to the methacrylate end group [δ4.2 (g)] appeared at the expected positions. The integration ratios of (e$_2$):(e$_1$):(g): (f) were 1:1:2:3 which demonstrated quantitative functionalization. The use of THF solvent gave incomplete conversion after 24 hours, although PEG-MA was obtained in quantitative yield under similar conditions. At this point we do not understand the reason for this discrepancy. We hope to get a better understanding of the mechanism of enzymatic polymerizations, which we are actively investigating.

Figure 8B:
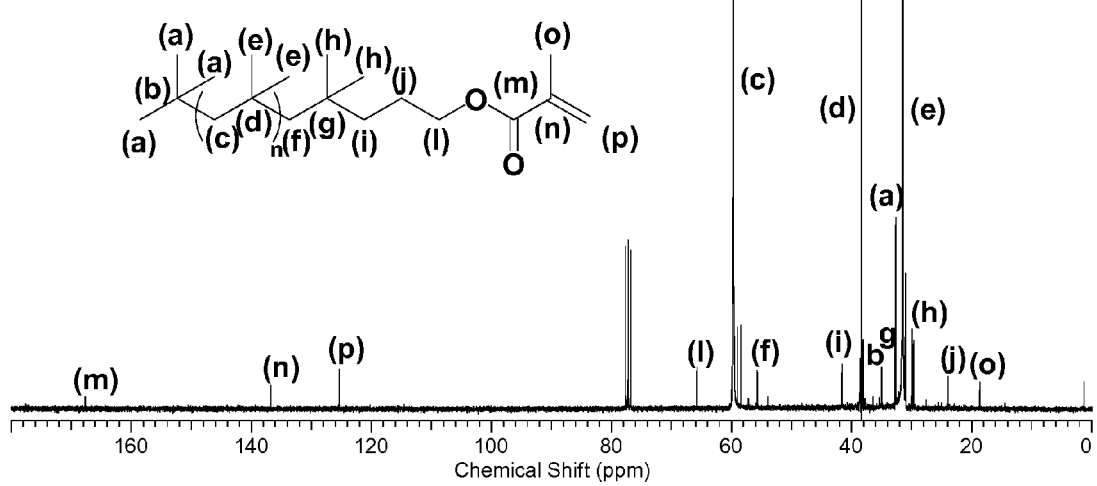
FIGS. 8a and 8b are the $^{13}$C NMR spectra of polyisobutylene before and after methacrylation.
Figure 8A:
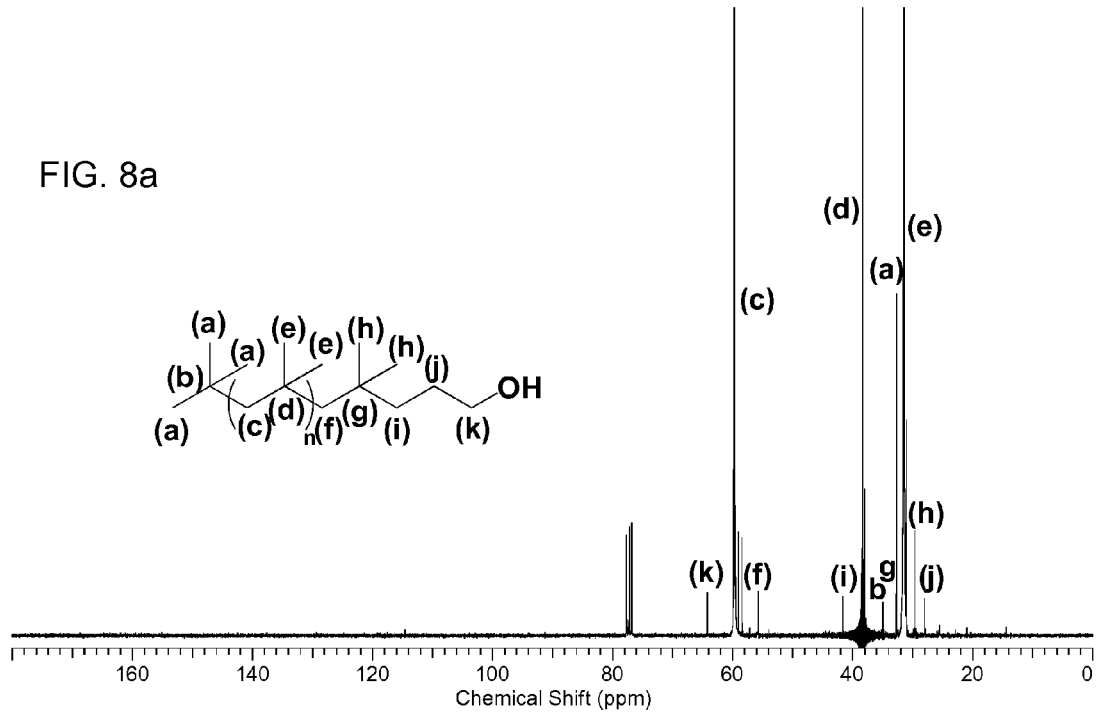

The $^{13}$C NMR spectrum of PIB before, as seen in FIG. 8*a*, and after, as seen in FIG. 8*b*, methacrylation are provided. The carbon connected to the —CH$_2$— protons next to the hydroxyl group at δ62.0 in the starting material shifted downfield to δ66.0 upon methacrylation, and new resonances appeared at the expected positions, confirming the structure of the product.

Figure 9:
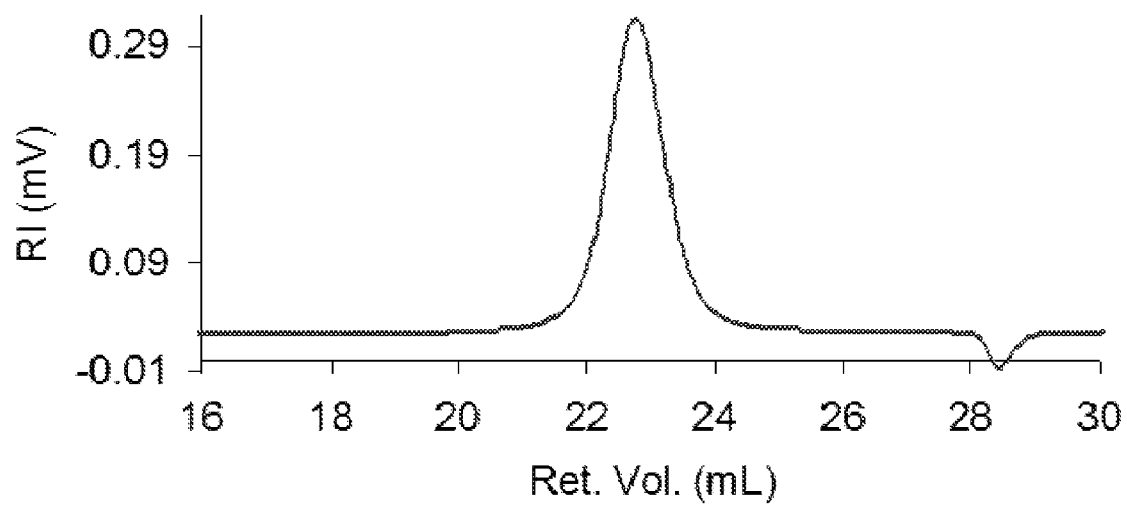
FIG. 9 is a size exclusion chromatography trace of a polyisobutylene-methacrylate polymer according to one embodiment of the invention.

The SEC trace of PIB-MA with M$_n$=5,260 g/mol and M$_n$/M$_w$=1.11 is shown in FIG. 9. Since the dn/dc of PIB-OH and PIB-MA are not known the M$_n$ values may not be accurate; however, the discrepancy should be minor and the measured values agree with the expected values within experimental error.

In another embodiment of the invention, Glissopal-OH made from Glissopal®2300, a commercially available PIB produced by BASF with ~82% exo- and ~18% endo-terminal unsaturated portions, was also methacrylated enzymatically as seen according to the scheme as shown in FIG. 6. Measurements revealed that the Glissopal®2300 had M$_n$=3,520 g/mol and M$_n$/M$_w$=1.37, and the resulting Glissopal-OH had M$_n$=3,570 g/mol, M$_1$/M$_w$=1.34.

Figure 10B:
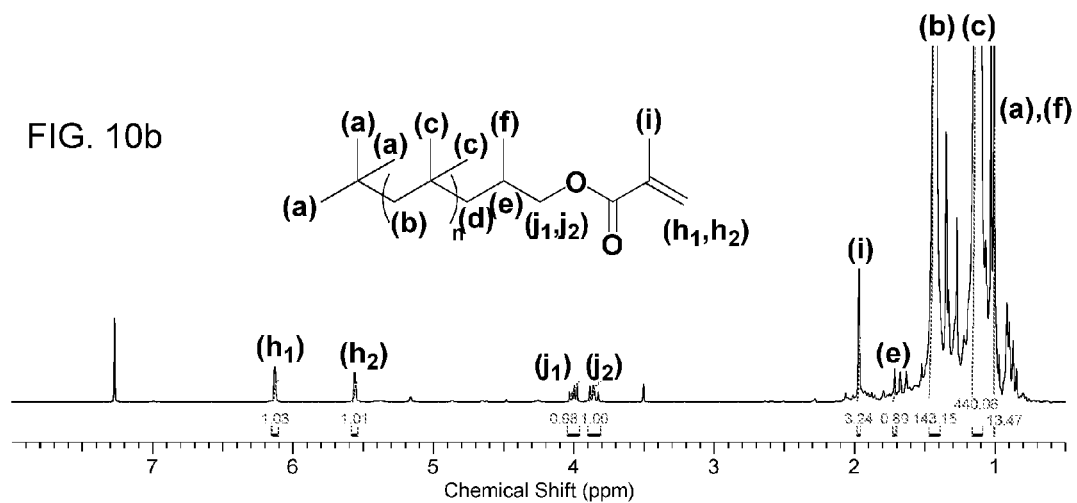
FIGS. 10a and 10b are the $^1$H NMR spectra of Glissopal-OH before and after methacrylation.
Figure 10A:
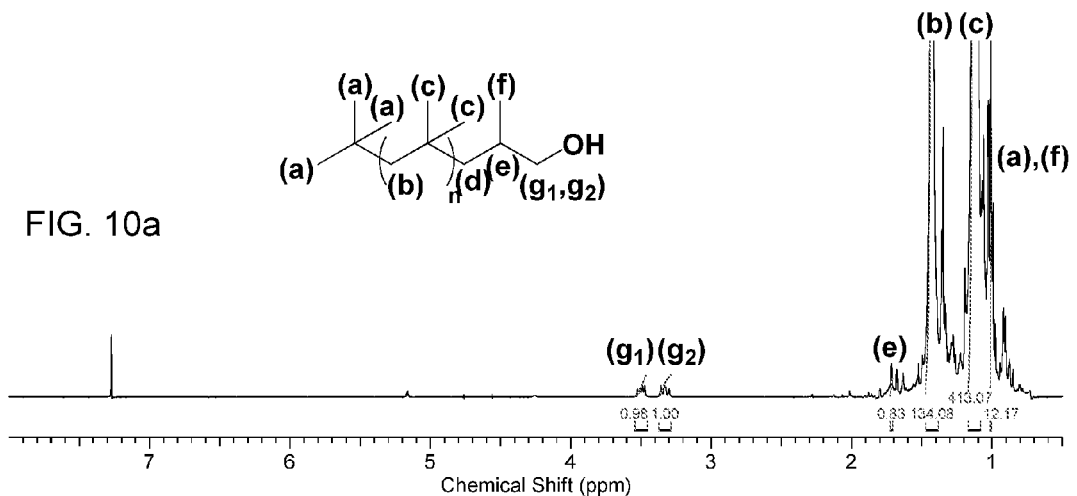
Figure 11B:
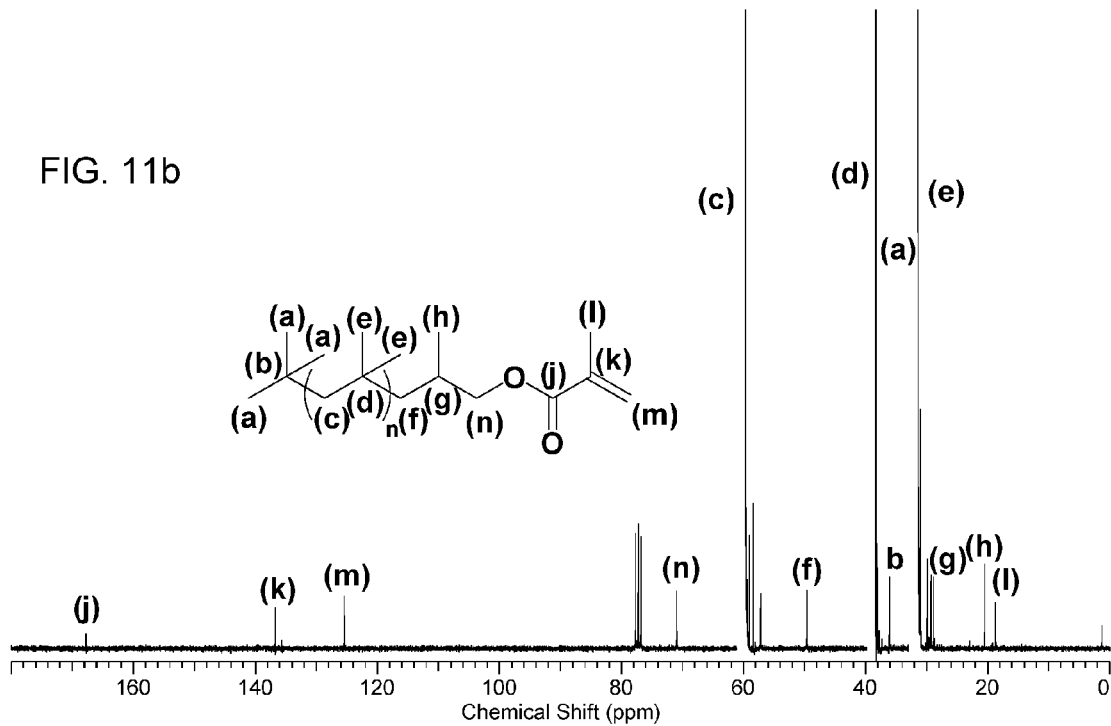
FIGS. 11a and 11b are the $^{13}$C NMR spectra of Glissopal-OH before and after methacrylation.
Figure 11A:
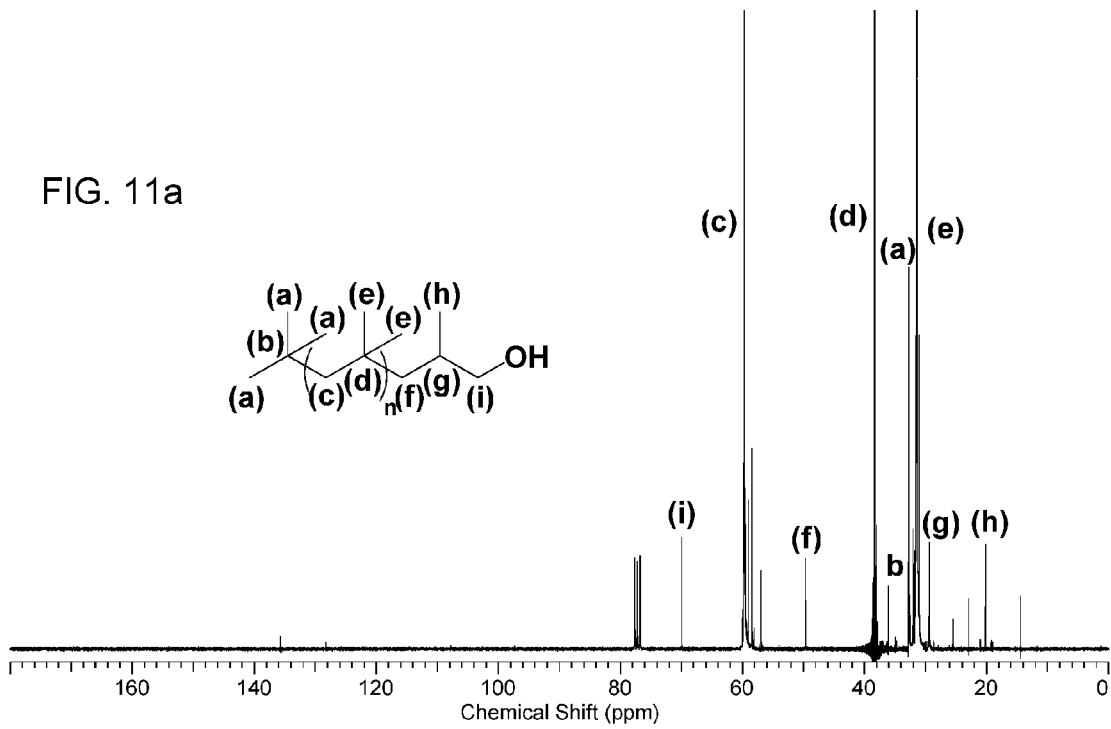

The $^1$H NMR spectrum of Glissopal-OH before, as seen in FIG. 10*a*, and after, as seen in FIG. 10*b*, methacrylation are provided. As seen in FIG. 10*b*, the —CH$_2$— proton resonances shifted downfield from δ3.3-3.6 to δ3.8-4.0 ppm, and the new peaks corresponding to the vinylidene [δ5.6 (h$_2$) and 6.2 ppm(h$_1$)] and methyl protons [δ1.9 ppm (i)] of the methacrylate end group appeared at expected positions, with the integral values confirming quantitative functionalization. The Glissopal-MA had M$_n$=3,720 g/mol and M$_n$/M$_w$=1.45. $^{13}$C NMR spectra of Glissopal-OH and Glissopal-MA also confirmed the structure of the product as seen in FIGS. 11*a* and 11*b*.

Figure 12B:
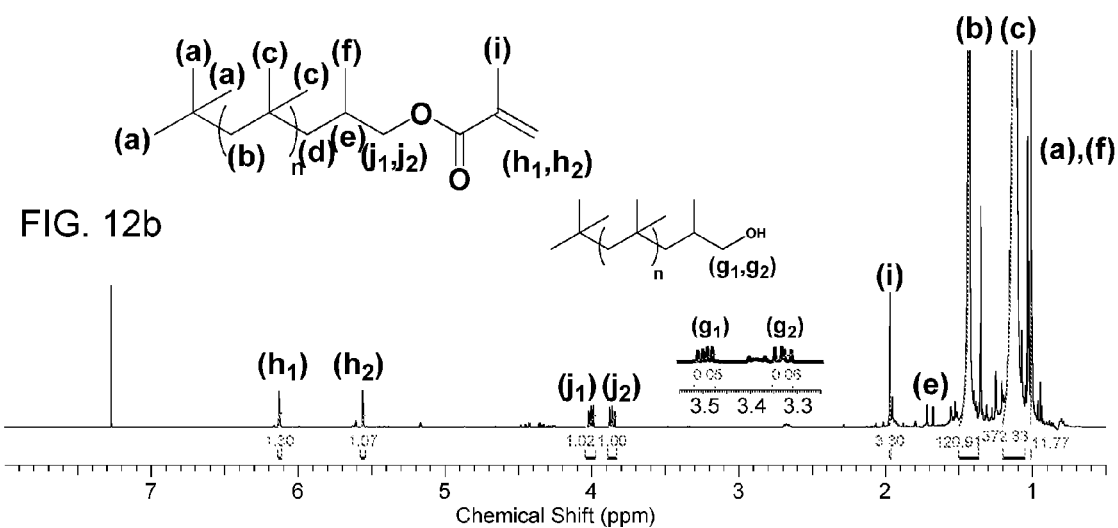
FIG. 12b is the H NMR spectrum of the reaction product of Glissopal-OH with vinylmethacrylate in bulk.
Figure 12A:
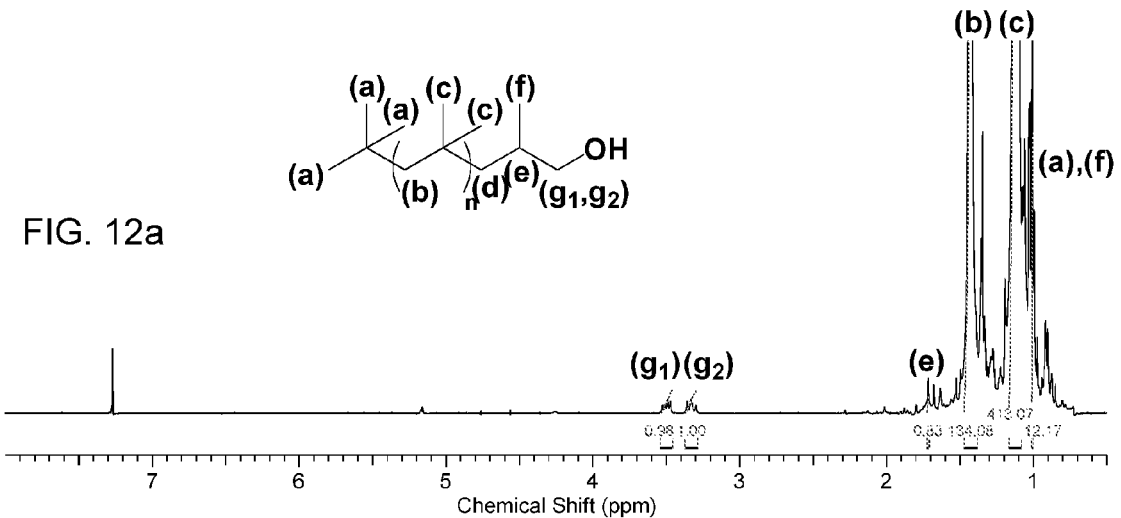
FIG. 12a is the $^1$H NMR spectrum of Glissopal-OH.

In another embodiment of the invention, Glissopal-OH made from Glissopal®2300 was enzymatically methacrylated in bulk. Glissopal-OH (about 0.39 g, 0.11 mmol) was placed in a 5 mL round bottom flask containing vinyl methacrylate (about 0.14 mL, 1.11 mmol) and CALB (about 10% by weight w.r.t. total weight of reactants). The flask was sealed with a septum and purged with nitrogen. The resulting mixture was stirred at about 300 rpm for about 24 hours at 50° C. After the reaction, the polymer was dried under reduced pressure for 3 hours at about 50° C. The $^1$H NMR spectra of Glissopal-OH and that of the reaction product of Glissopal-OH with vinylmethacrylate in bulk are shown in FIGS. 12*a* and 12*b* respectively. Similarly to the reaction in THF (FIGS. 10*a* and 10*b*), the conversion was quantitative. The resonances at δ3.3-3.5 ppm corresponding to the —CH$_2$— protons next to the hydroxyl group in Glissopal-OH shifted downfield to δ3.8-4.0 ppm upon methacrylation; and the new peaks corresponding to the vinylidene [δ5.6 (h$_2$) and 6.1 ppm(h$_1$)] and methyl protons [δ2.0 ppm (i)] of the methacrylate end group appeared at expected positions.

In yet another embodiment of the invention, the transesterification method includes reacting an ester with a polysiloxane in the presence of an effective amount of the enzyme catalyst. In one embodiment of the invention, the ester may be selected from vinyl acetate, vinyl methacrylate and combinations thereof. In another embodiment of the invention, the polysiloxane is polydimethylsiloxane. In yet a further embodiment of the invention, the enzyme catalyst is a lipase, wherein the lipase is CALB.

Methacrylate-functionalized polydimethylsiloxanes may be used as macromonomers in the production of hydrogels including soft contact lens applications. They can either be prepared by reacting an amount of a polydimethylsiloxane diol with a predetermined amount of methacryloyl chloride or a diisocyanate followed by reaction with hydroxyethylmethacrylate (HEMA). In the former case the use of methacryloyl chloride is disadvantageous due to its high toxicity. In the latter case, even when an appropriate stoichiometry is used, chain extension is unavoidable. Therefore, an enzymatic transesterification strategy may be an alternative for the production of this macromonomer.

Figure 13:
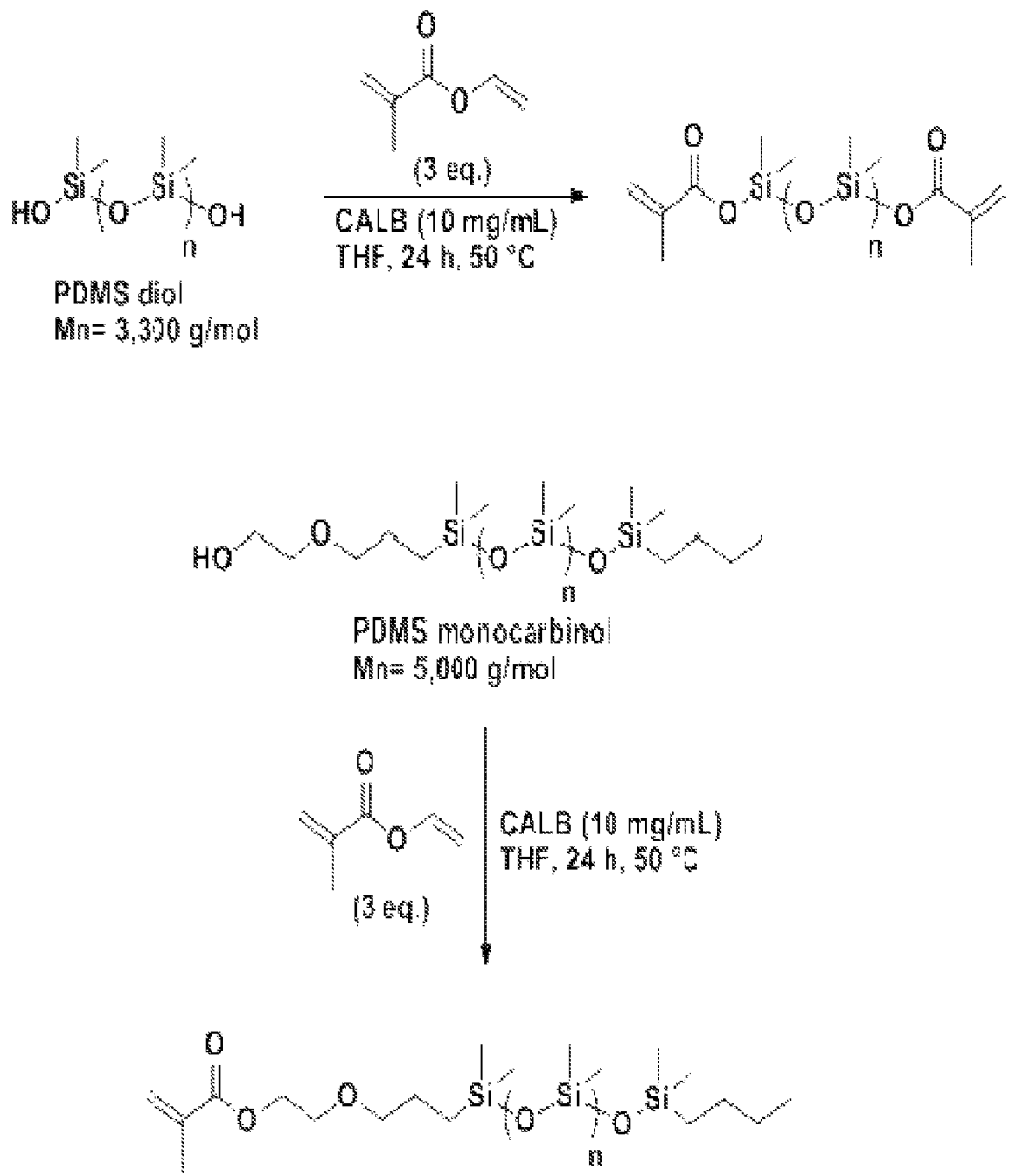
FIG. 13 illustrates the scheme of the transesterification of vinyl methacrylate with poly(dimethylsiloxane)s.

In one embodiment of the invention, a methacrylate-functionalized poly(dimethylsiloxane) was prepared by introducing polydimethylsiloxane diol (about 0.75 g, about 0.23 mmol) in a 25 mL round bottom flask containing CALB (about 10 mg/mL), vinyl methacrylate (about 0.17 mL, about 1.4 mmol) and about 10 mL of THF distilled from sodium benzophenone. The flask was sealed with a septum and purged with nitrogen. The resulting solution was stirred at about 300 rpm for about 24 hours at 50° C. After the reaction, the enzyme was filtered, the polymer was dried under reduced pressure overnight at about 50° C. (yield: about 0.66 g). In another embodiment of the invention, and following the same procedure, polydimethylsiloxane monocarbinol (about 0.98 g, about 0.2 mmol) was methacrylated and the yield was about 0.85 g. Both of these reactions are shown schematically in FIG. 13.

Figure 14B:
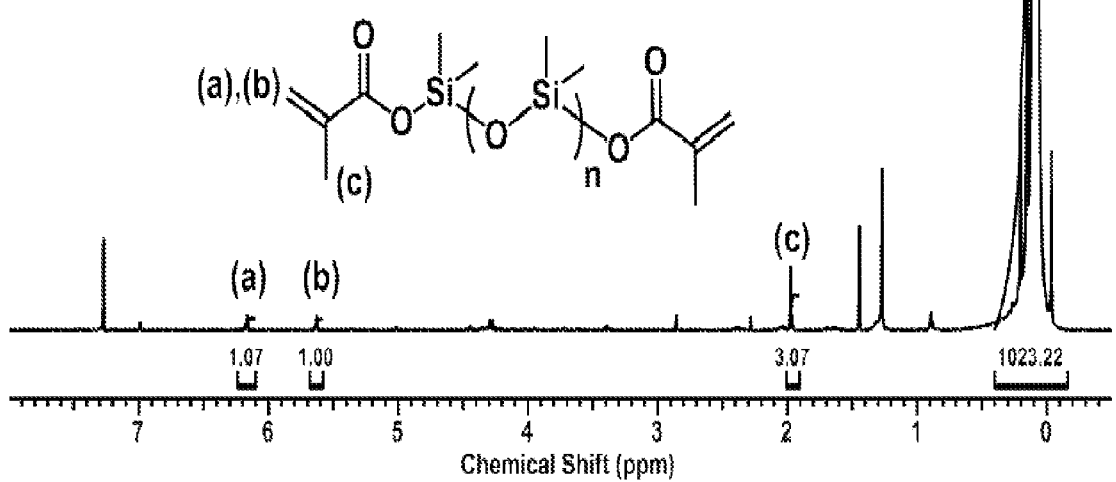
FIG. 14b is the $^1$H NMR of the reaction product of poly (dimethylsiloxane) diol with vinylmethacrylate.
Figure 14A:
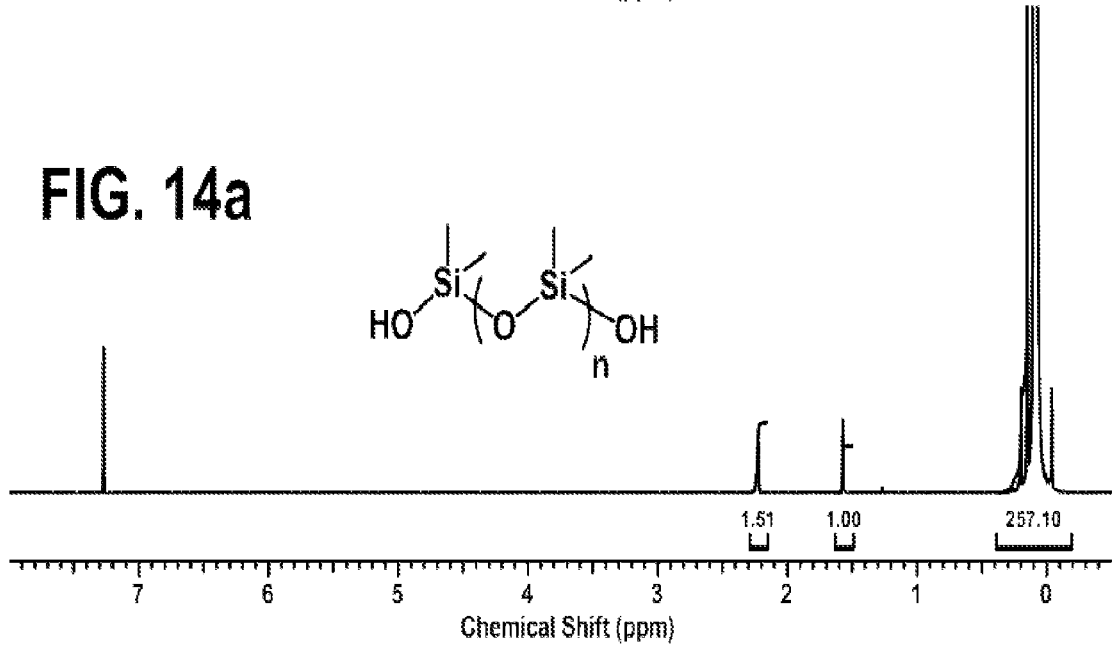
FIG. 14a is the $^1$H NMR of poly(dimethylsiloxane) diol.

As seen in FIGS. 14*a* and 14*b*, the $^1$H NMR of PDMS diol and the reaction product of PDMS diol with VMA are shown. The vinylidene protons at δ 5.65 and 6.20 ppm (a and b), and the methyl protons of the methacrylate group at δ 1.95 ppm (c) proved that the PDMS-diol does react with the VMA. The peaks at δ 1.5 and 2.25 ppm in the starting material NMR spectrum could not be assigned to anything. However, both peaks disappeared upon methacrylation. In order to see if these peaks were coming from hydroxyl protons, deuterium oxide was added to the NMR solution, but no change in the spectrum was observed.

Figure 15B:
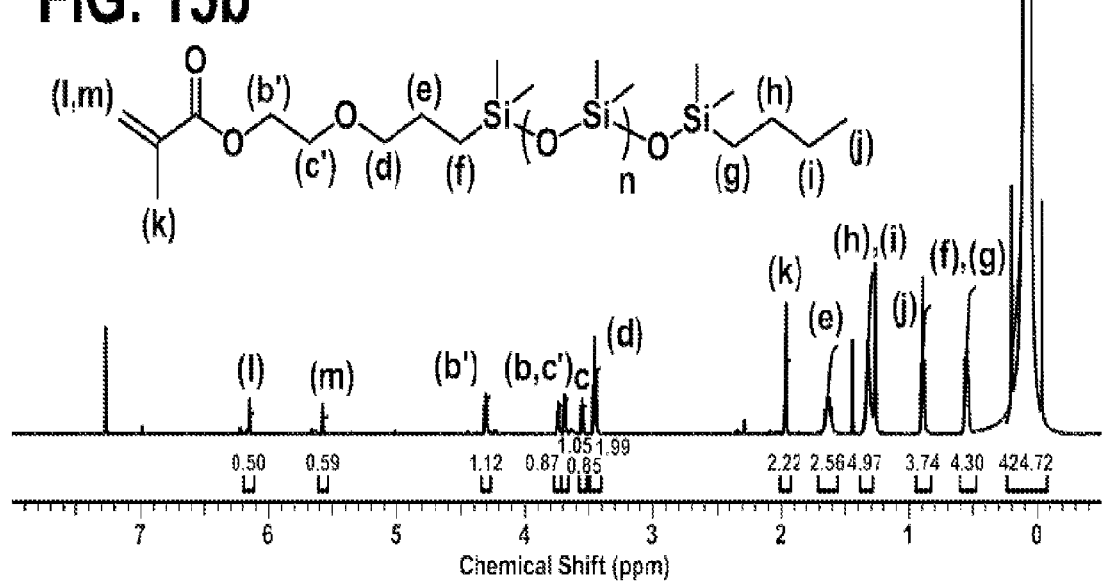
FIG. 15b is the $^1$H NMR spectrum of the reaction product of poly(dimethylsiloxane) monocarbinol with vinylmethacrylate.
Figure 15A:
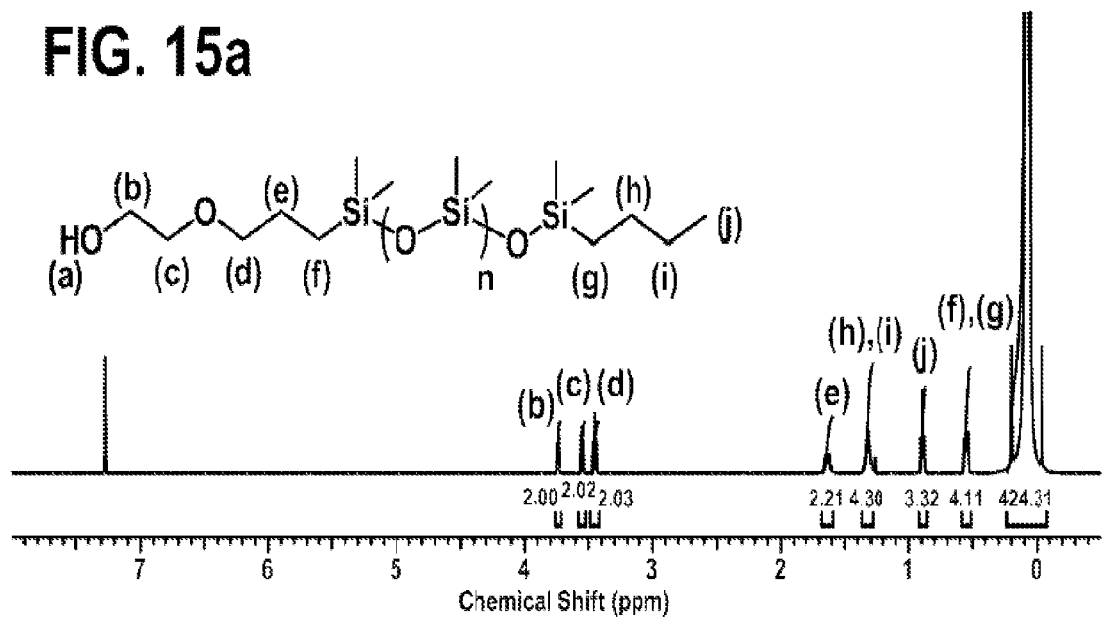
FIG. 15a is the $^1$H NMR spectrum of poly(dimethylsiloxane) monocarbinol.

The $^1$H NMR of PDMS monocarbinol and the reaction product of PDMS monocarbinol with VMA are shown in FIGS. 15*a* and 15*b*. The NMR of the product showed that the desired methacrylated-PDMS was obtained as seen from the vinylidene protons δ 5.60 and 6.20 ppm (l and m), and methyl protons of the methacrylate group (k) at δ 1.95 ppm. The ratio between vinylidene protons (l) and (m) and (b') was 1:1:2 which was in accordance with the expected structure, though in 1H NMR of silicons, the integral ratios may not be good indications of relative amounts of products.

In yet another embodiment of the invention, the methacrylate-functionalized poly(dimethylsiloxane)s were prepared in bulk by introducing polydimethylsiloxane diol (about 1.04 g, about 0.32 mmol) in a 5 mL round bottom flask containing CALB (about 10% by weight w.r.t. total weight of reactants) and vinyl methacrylate (about 0.23 mL, about 1.9 mmol). The flask was sealed with a septum and purged with nitrogen. The resulting mixture was stirred at about 300 rpm for about 24 hours at 50° C. After the reaction, the enzyme was filtered; the polymer was dried under reduced pressure overnight at about 50° C. In still yet another embodiment of the invention, polydimethylsiloxane monocarbinol (about 1.12 g, about 0.22 mmol) was methacrylated by following the same procedure.

Figure 16B:
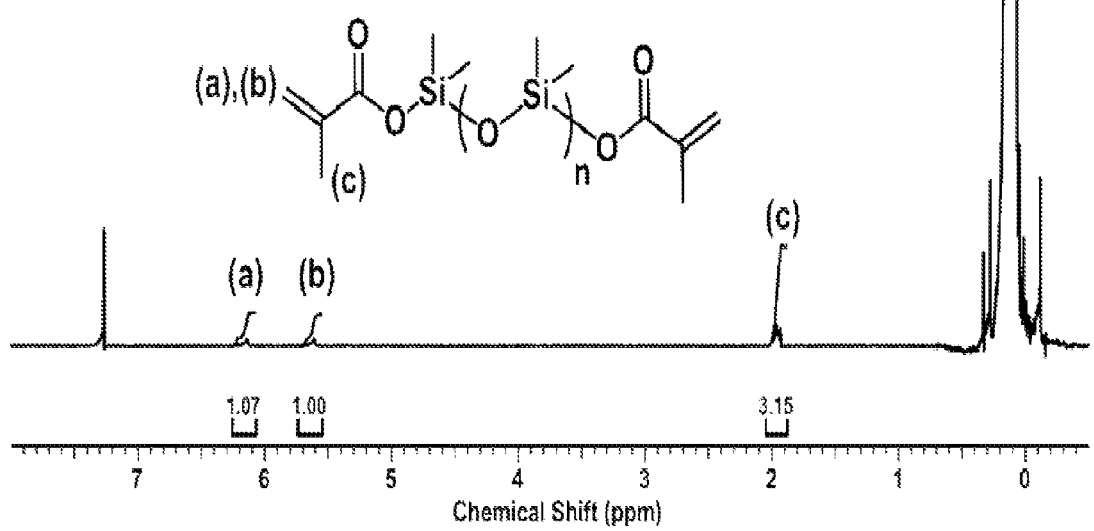
FIG. 16b is the $^1$H NMR of the reaction product of poly (dimethylsiloxane) diol with vinylmethacrylate in bulk.
Figure 16A:
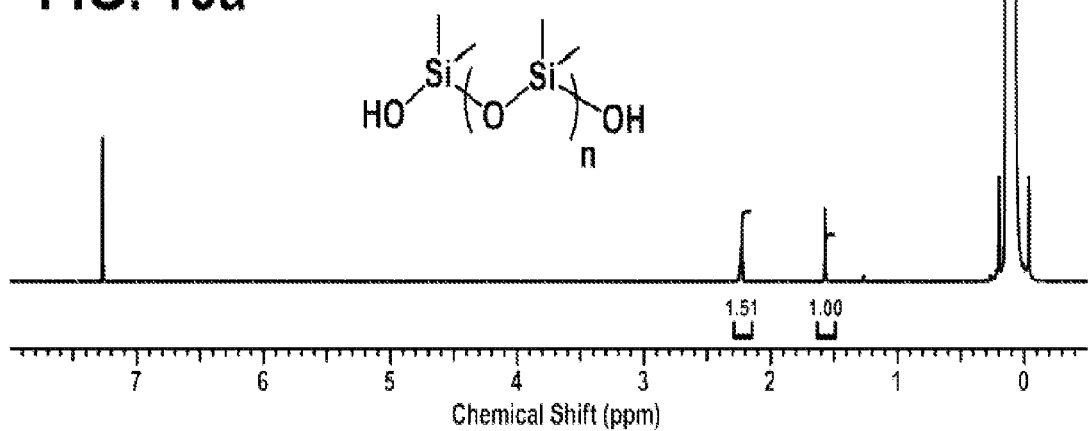
FIG. 16a is the $^1$H NMR of poly(dimethylsiloxane) diol.
Figure 17B:
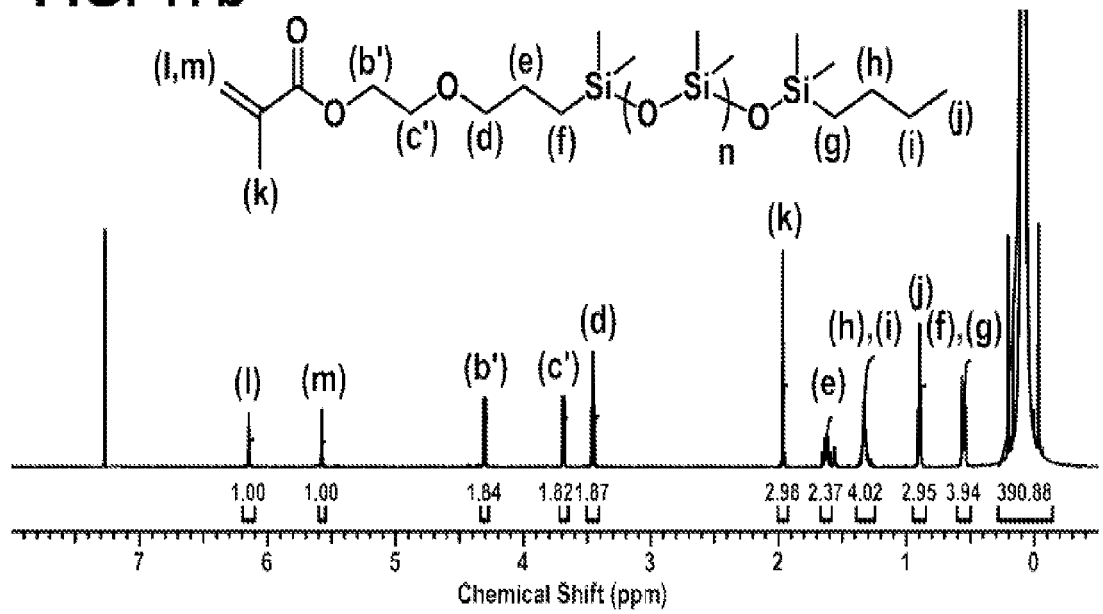
FIG. 17b is the $^1$H NMR spectrum of the reaction product of poly(dimethylsiloxane) monocarbinol with vinylmethacrylate in bulk.
Figure 17A:
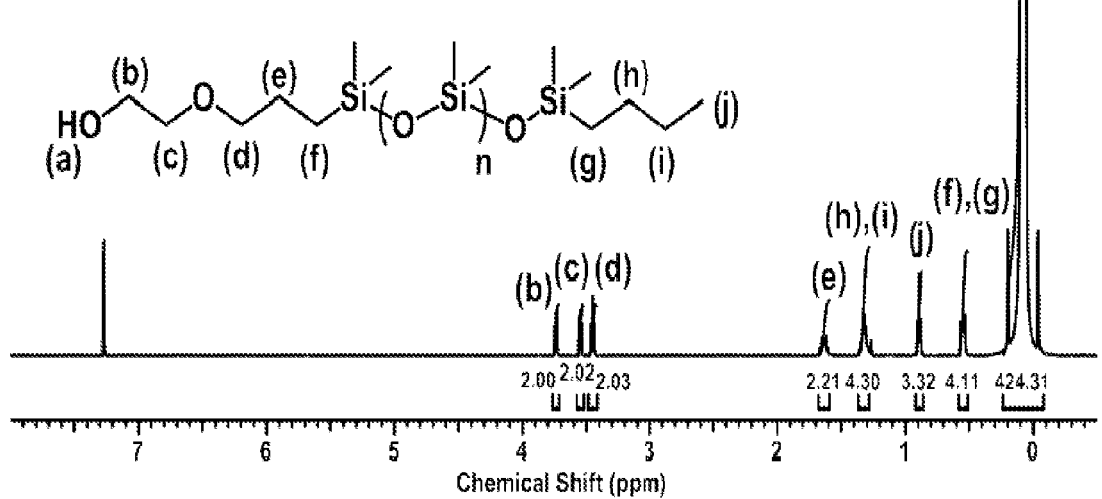
FIG. 17a is the $^1$H NMR spectrum of poly(dimethylsiloxane) monocarbinol.

The $^1$H NMR spectra of silanol-terminated poly(dimethylsiloxane) before and after methacrylation are shown in FIGS. 16a and 16b respectively; and that of monocarbinol-terminated poly(dimethylsiloxane) before and after methacrylation are given in FIGS. 17a and 17b respectively.

It was observed by $^1$H NMR spectroscopy that the monocarbinol-terminated poly(dimethylsiloxane) reacted completely with vinyl methacrylate resulting in pure methacrylated polymer as indicated in FIG. 17b. Moreover, there was no chain extension in the resulting polymer as the integral value of the peak in the range δ–0.05-0.25 ppm corresponding to the backbone methyl protons stayed approximately the same upon methacrylation.

Figure 18:
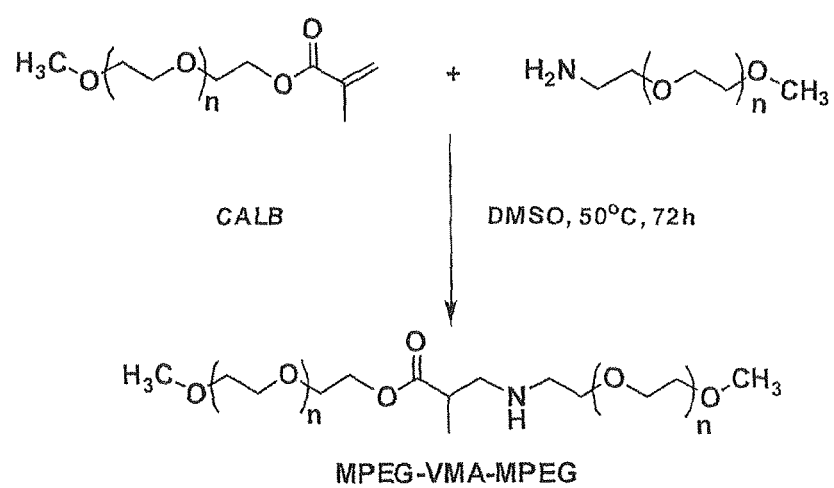
FIG. 18 illustrates the scheme of the vinyl methacrylate linking reaction between two poly(ethylene glycol)s.

In yet another embodiment of the invention, vinyl methacrylate was used as a linker by reacting the transesterification reaction product, prepared by reacting a glycol ether and vinyl methacrylate in the presence of an effective amount of an enzyme catalyst, with an aminoethoxy glycol ether in the presence of an effective amount of an enzyme catalyst via Michael addition. In one embodiment of the invention, the glycol ether may be polyethylene glycol monomethyl ether and the aminoethoxy glycol ether is aminoethoxy polyethylene glycol monomethyl ether. In yet another embodiment of the invention, the enzyme catalyst is a lipase, wherein the lipase is CALB or Amano Lipase M (ALM). The reaction is shown schematically in FIG. 18.

Figure 19:
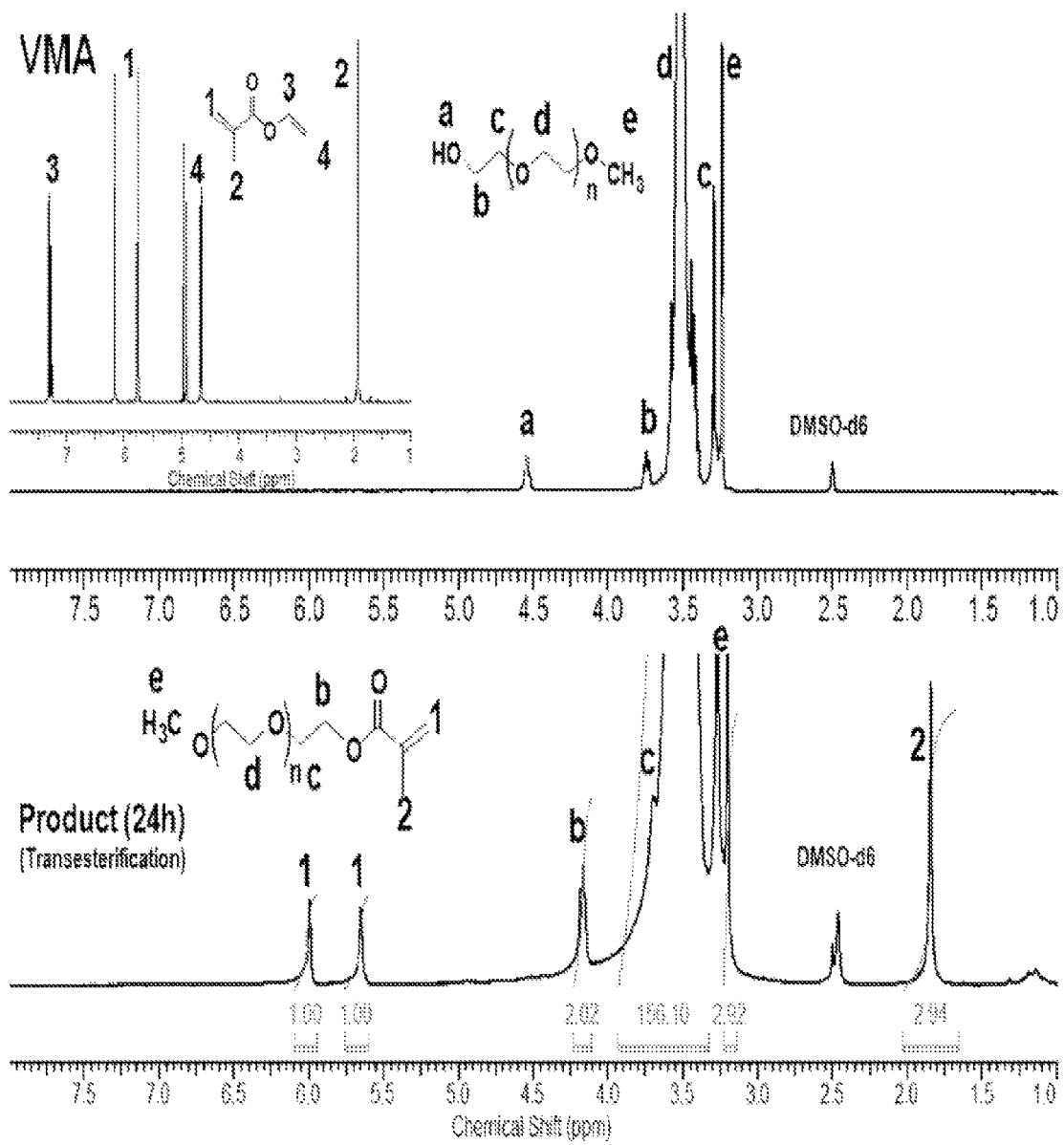
FIG. 19 is the $^1$H NMR spectrum of the product of the first step: the reaction between poly(ethylene glycol) monomethyl ether and vinyl methacrylate, according to one embodiment of the invention.

The transesterification reaction product of a glycol ether and vinyl methacrylate in the presence of an effective amount of an enzyme catalyst was prepared by dissolving about 1.0 g of polyethylene glycol monomethyl ether (about 0.5 mmol) and about 0.168 g of vinyl methacrylate (about 1.5 mmol) in about 22.5 mL of distilled THF. About 225 mg of CALB (about 10 mg/mL) was then added into the solution. The suspension was stirred for about 24 hours at about 50° C. The CALB was filtered out using a sintered funnel with a vacuum pump. The THF and unreacted VMA were removed by evaporating under the reduced pressure (about 50 mbar) at about 40° C. The white product was dissolved in distilled THF and precipitated in about 150 mL of hexane. The precipitate was dried in vacuum and the $^1$H NMR of the product is shown in FIG. 19.

Figure 20:
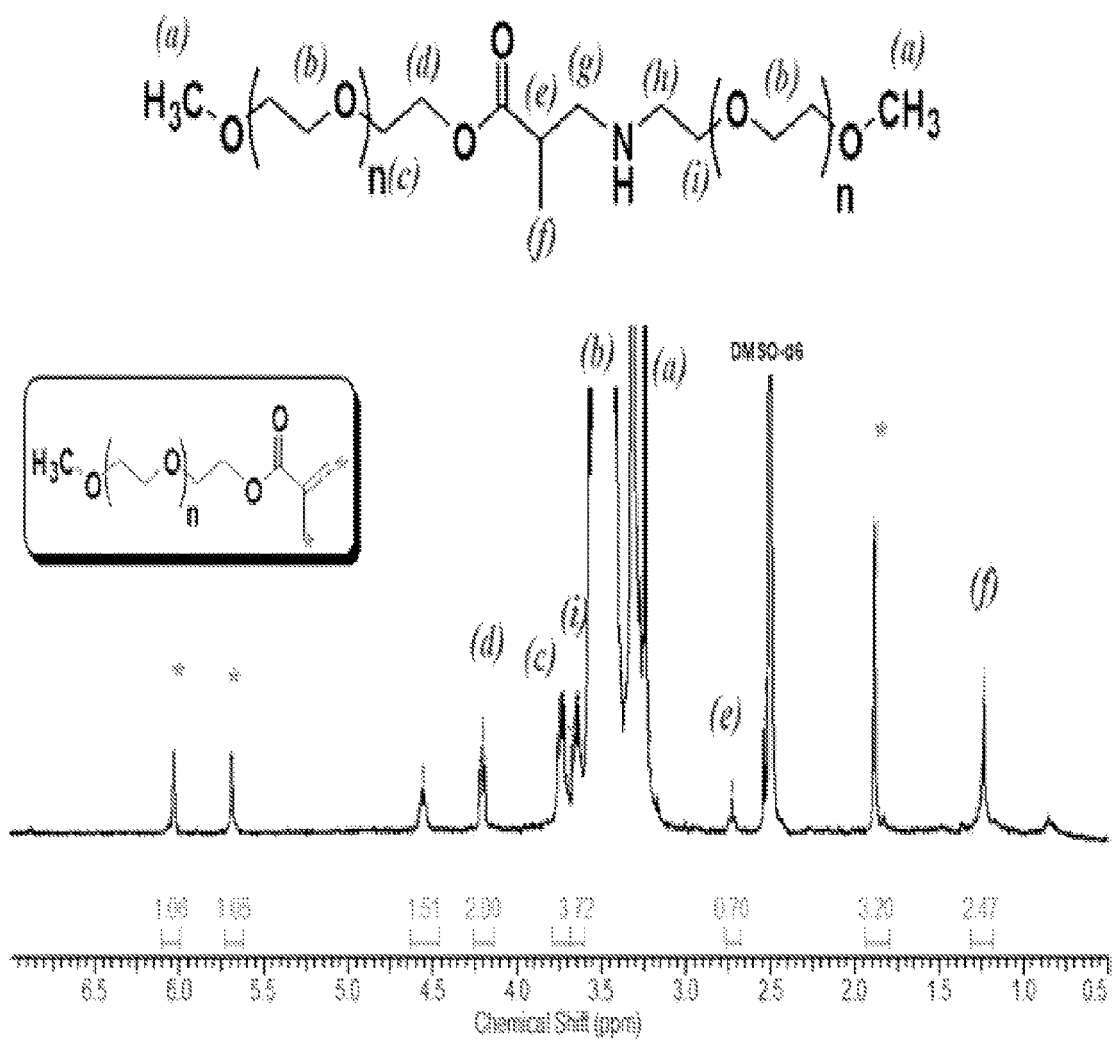
FIG. 20 is the $^1$H NMR spectrum of the product of the reaction depicted in FIG. 18.

The polymer coupling reaction was carried out by dissolving about 0.1 g of aminoethoxy polyethylene glycol monomethyl ether (about 50 μmol) and 0.1575 g of methacrylate-functionalized poly(ethylene glycol) monomethyl ether (about 1.5 eq.) in about 5 mL of anhydrous DMSO. About 200 mg of CALB was added into the solution and stirred for about 72 hours. The product was centrifuged and the upper solution was collected into volumetric flask. The solvent was removed under vacuum at about 70° C. The precipitate was dried in vacuum and the $^1$H NMR of the product is shown in FIG. 20. Using the same method, block copolymers such as PEG-PIB, PEG-PDMS and their variations (diblocks, triblocks or multiblocks) can be prepared.

In still yet another embodiment of the invention, the transesterification method includes preparing a dendrimer by reacting a polyether diamine or an aminoethoxy glycol ether with a functionalized nitrogen heterocycle in the presence of an effective amount of the enzyme catalyst. In one embodiment of the invention, the polyether diamine is a polyethylene glycol diamine and the aminoethoxy glycol ether is aminoethoxy polyethylene glycol monomethyl ether. In another embodiment of the invention, the functionalized nitrogen heterocycle includes functionalized pyridines, functionalized diazines, functionalized triazines and functionalized tetrazines. An example of a functionalized triazine is triacryloyl hexahydro-triazine. In yet a further embodiment of the invention, the enzyme catalyst is a lipase, wherein the lipase is CALB.

Figure 21:
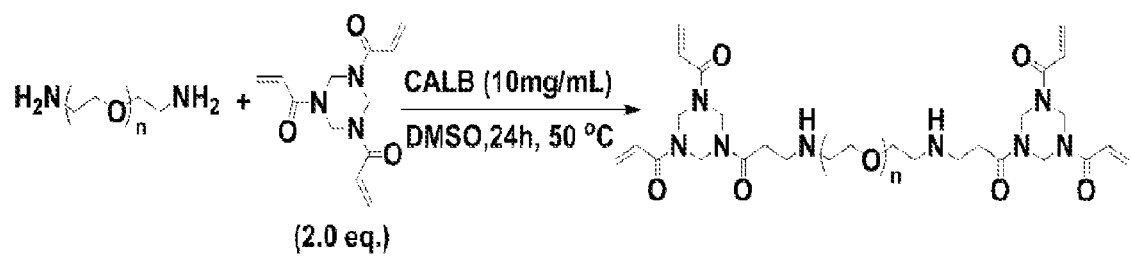
FIG. 21 illustrates a scheme of a reaction for forming the core of a dendrimer according to one embodiment of the invention; transesterification with HO-PEG-OH will yield the first generation.

In one embodiment of the invention, a dendrimer may be prepared via a Michael addition reaction, as seen in FIG. 21. However, based on the stoichiometry, a polymer gel formed when about 0.2 g (about 0.1 mmol) of polyethylene glycol diamine and about 0.0977 g (about 0.4 mmol) of triacryloyl hexahydro-triazine was reacted in about 5 mL of anhydrous DMSO. About 50 mg of CALB (about 10 mg/mL) was added into the solution. The suspension was stirred for about 24 hours at about 50° C. The product was a gelled, crosslinked polyethylene glycol.

Figure 22:
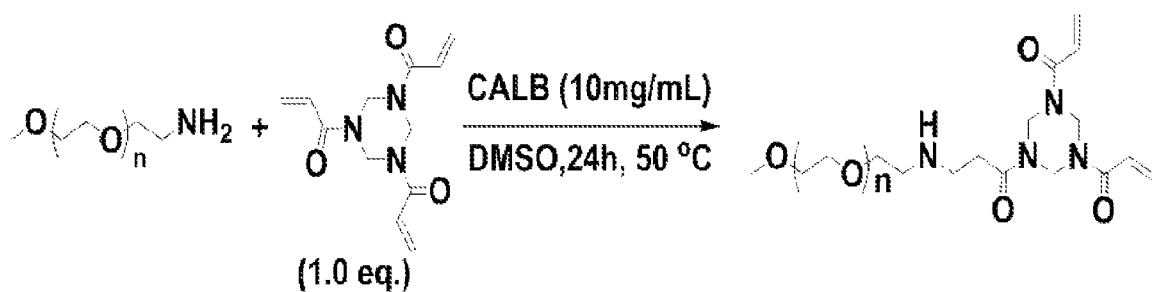
FIG. 22 illustrates a scheme of a reaction for a selective reaction according to another embodiment of the invention.
Figure 23:
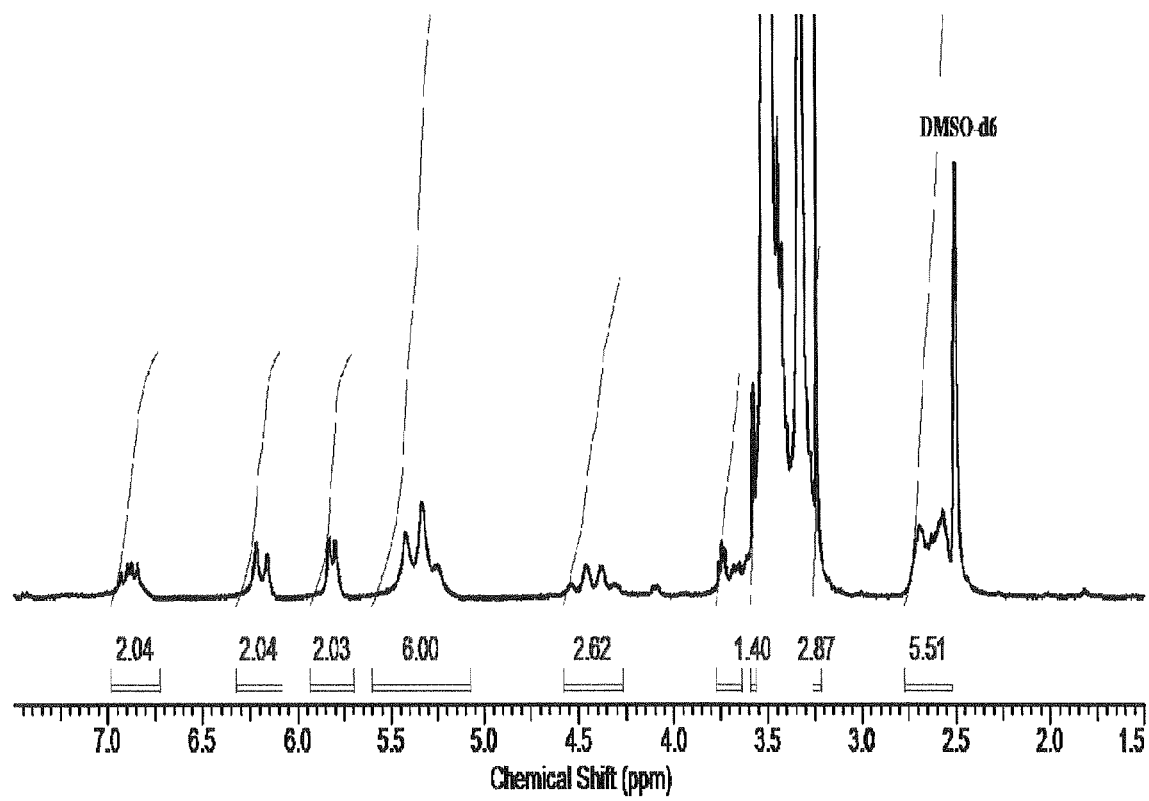
FIG. 23 is the $^1$H NMR spectrum of a monosubstituted compound prepared according to the reaction of FIG. 22.

In another embodiment of the invention, the dendrimer may be prepared via a Michael addition reaction, as seen in FIG. 22, by dissolving about 0.1 g (about 50 μmol) aminoethoxy polyethylene glycol monomethyl ether and about 0.0125 g (about 50 μmol) of triacryloyl hexahydro-triazine in about 5 mL of anhydrous DMSO. About 50 mg (about 10 mg/mL) of CALB was added into the solution. The suspension stirred for about 24 hours at about 50° C. $^1$H NMR analysis of the product is seen in FIG. 23.

Figure 24:
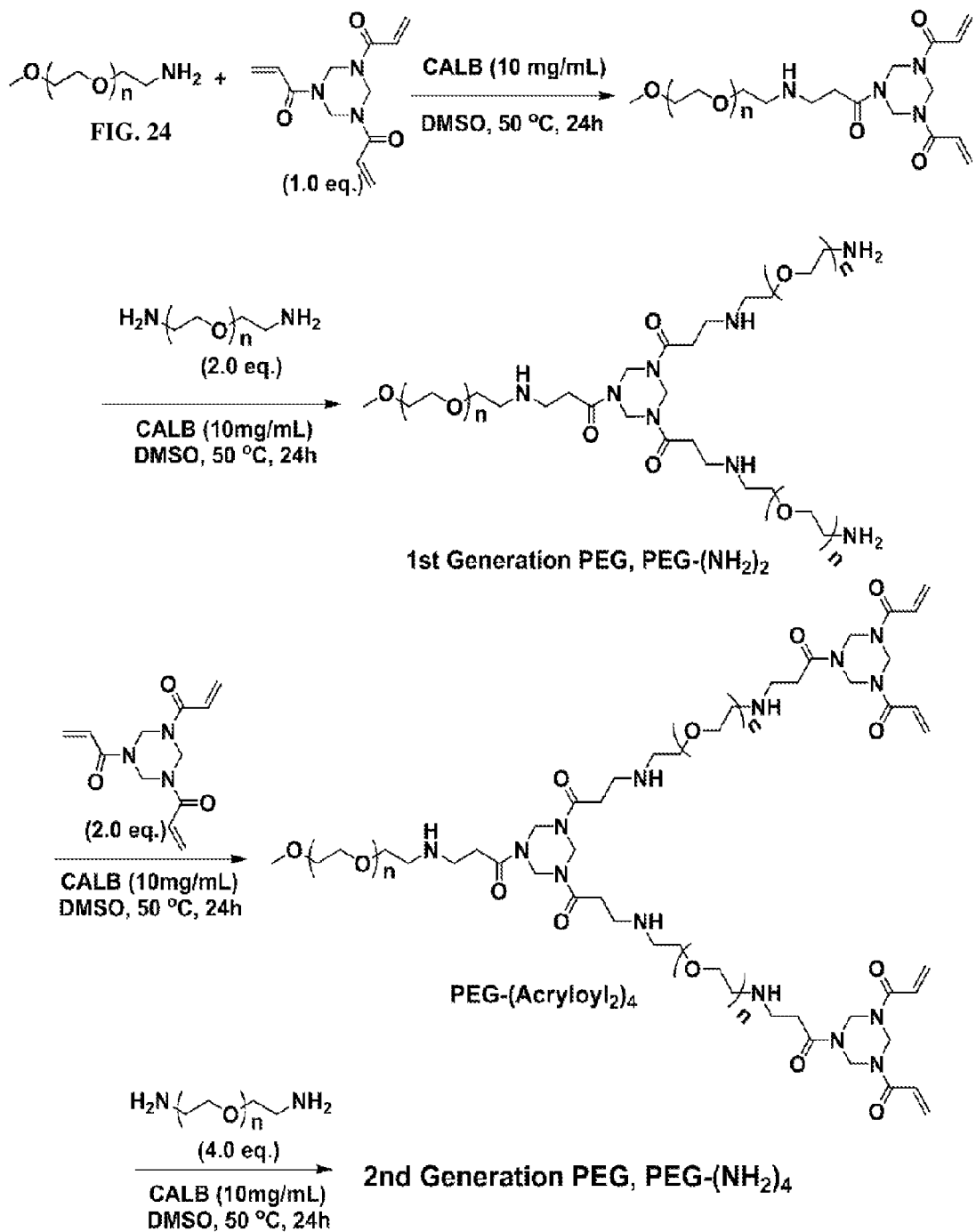
FIG. 24 illustrates the synthesis of a dendrimer using Michael addition.

In another embodiment of the invention, it is envisioned that functionalized polymers prepared via a transesterification process with an enzymatic catalyst as described in examples, may be further modified for the purposes of drug delivery. In one example, it is envisioned that a methacrylate-functionalized glycol ether, such as a methacrylate-functionalized poly(ethylene glycol) monomethyl ether, may be reacted with a vitamin, such as folic acid, a mineral and combinations thereof, in the presence of an enzymatic catalyst to form a drug that may be administered to a patient. In one aspect of the invention, the drug is prepared by reacting a methacrylate-functionalized poly(ethylene glycol) monomethyl ether with folic acid via a Michael addition reaction in the presence of Amano Lipase M to form a folic acid modified methacrylate-functionalized poly(ethylene glycol) monomethyl ether compound (see FIG. 24).

Figure 25:
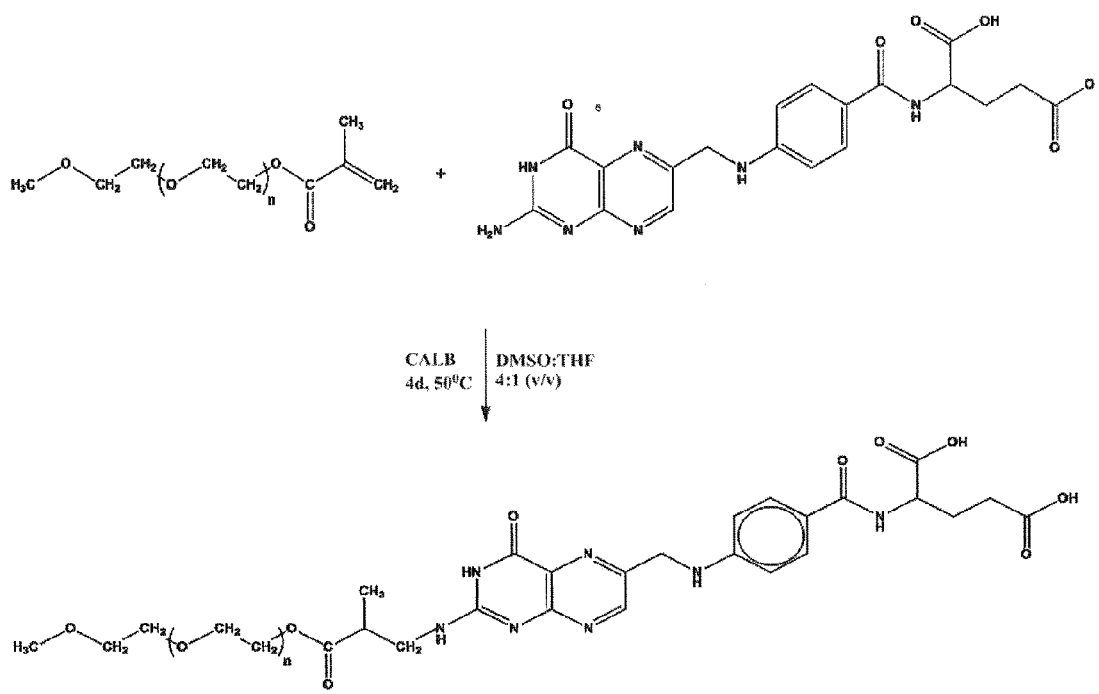
FIG. 25 illustrates a scheme of a reaction for conjugation of folic acid onto poly(ethylene glycol) monomethyl ether.

A scheme of a reaction for conjugation of folic acid onto poly(ethylene glycol) monomethyl ether in FIG. 25. In this example, folic acid (0.33 g, 0.75 mmol) was dissolved in DMSO (10 mL) at room temperature and then methacrylate-functionalized poly(ethylene glycol) monomethyl ether (0.5 g, 0.25 mmol) dissolved in 2.5 mL of THF was added dropwise to the folic acid solution. To neutralize the reaction medium, 0.3 mL of triethylamine was added and then CALB (125 mg) was added. The reaction flask was sealed with a septum, purged with nitrogen and the mixture was stirred at 300 rpm for 4 days at 50° C. The enzyme was removed by centrifuging the solution. The solvent was removed under reduced pressure and THF was added to the crude product to dissolve the polymer. The polymer was precipitated into hexane.

Figure 26:
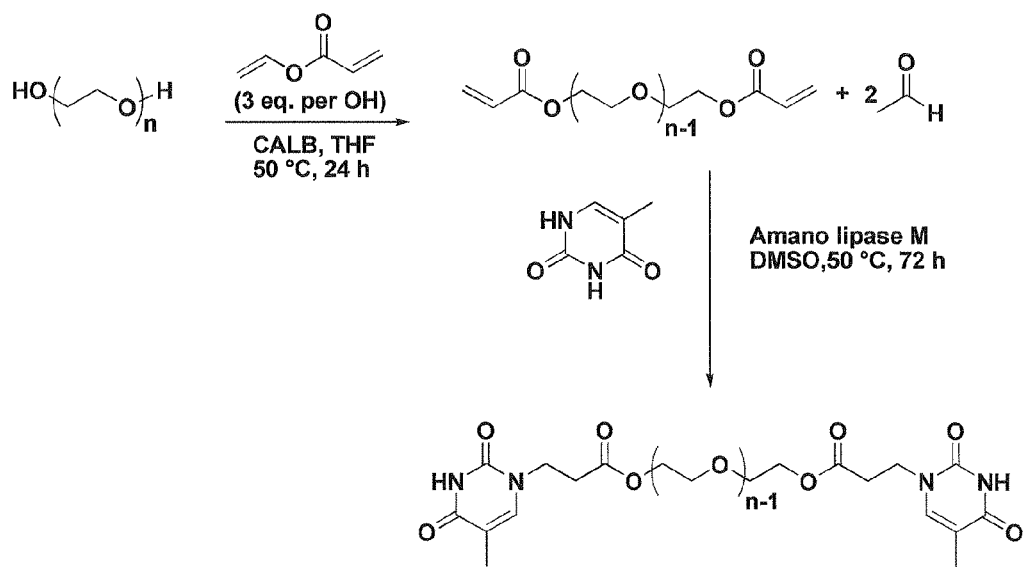
FIG. 26 illustrates an example of the preparation of thymine-functionalized PEG by CALB-catalyzed transesterification of vinyl acrylate followed by Amano lipase M-catalyzed Michael addition of thymine.

In a further example according to the invention, the preparation of thymine-funtionalized poly(ethylene glycol)s is described. The transesterification of vinyl (meth)acrylate with hydroxyl-functionalized polymers introduces (meth)acrylate functionality at the polymer chain end. Functional groups possessing sufficient nucleophilicity can add across the carbon-carbon double bond of the (meth)acrylate through a Michael addition reaction for further functionalization of the chain end. Functionalization of PEG with thymine by Michael addition was performed using ditelechelic PEG-acrylate as the Michael donor and Amano lipase M from Mucor javanicus as the enzyme. The PEG-diacrylate was prepared via transesterification of vinyl acrylate with PEG ($M_n$=2,200 g/mol, $M_w/M_n$=1.23) as shown in FIG. 26. The Michael addition reaction was carried out in DMSO because of the insolubility of thymine in non-polar solvents.

Figure 27A:
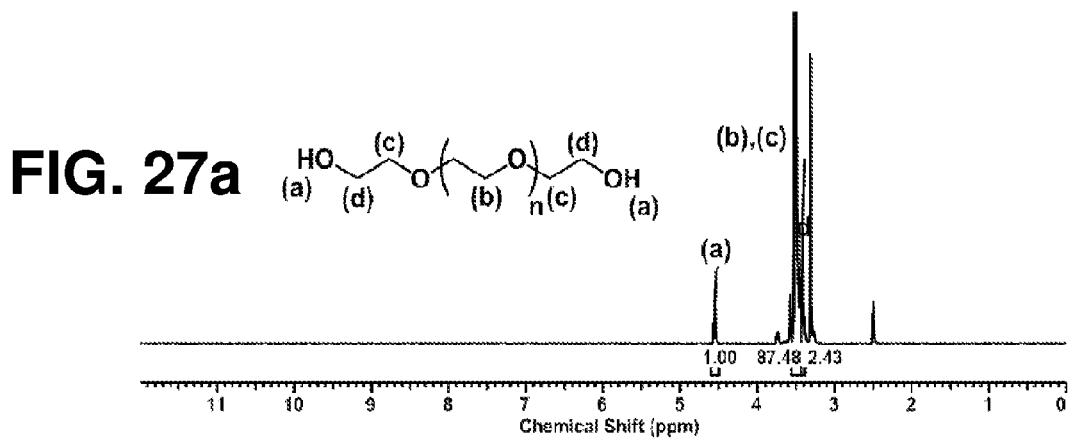
FIG. 27 are the $^1$H NMR spectra of the compounds prepared according to the reaction of FIG. 26, with (a) showing PEG ($M_n$=2,200 g/mol, $M_w/M_n$=1.23), (b) its transesterification product with vinyl acrylate, and (c) the product of Michael addition of thymine to ditelechelic PEG-acrylate (solvent: DMSO-$d_6$).
Figure 27B:
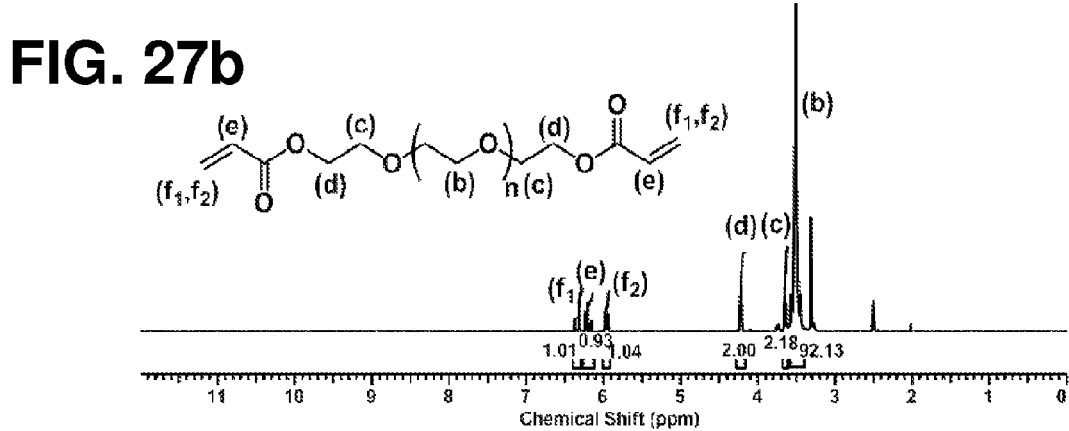
Figure 27C:
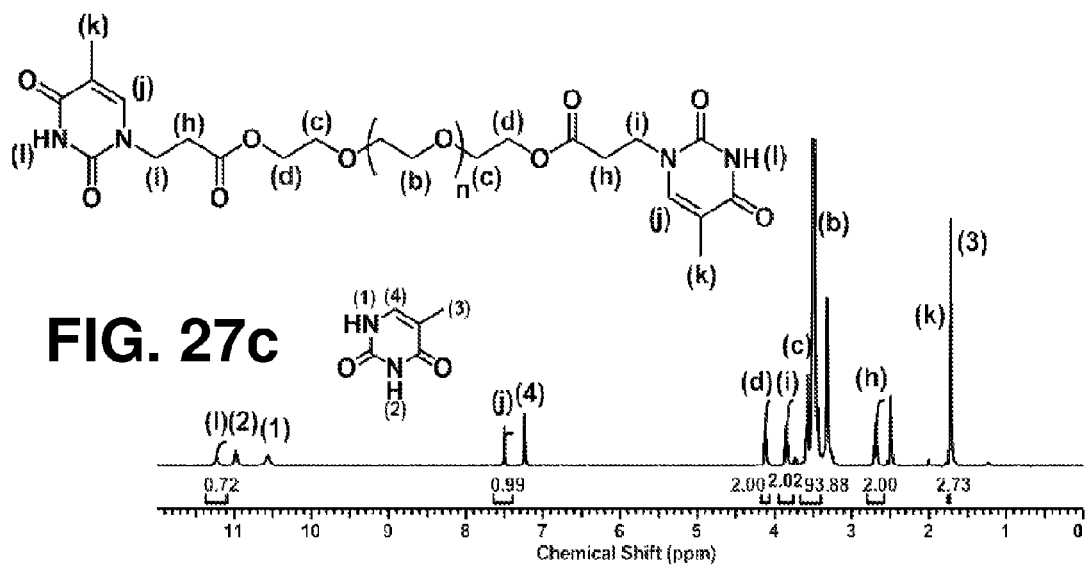
Figure 28:
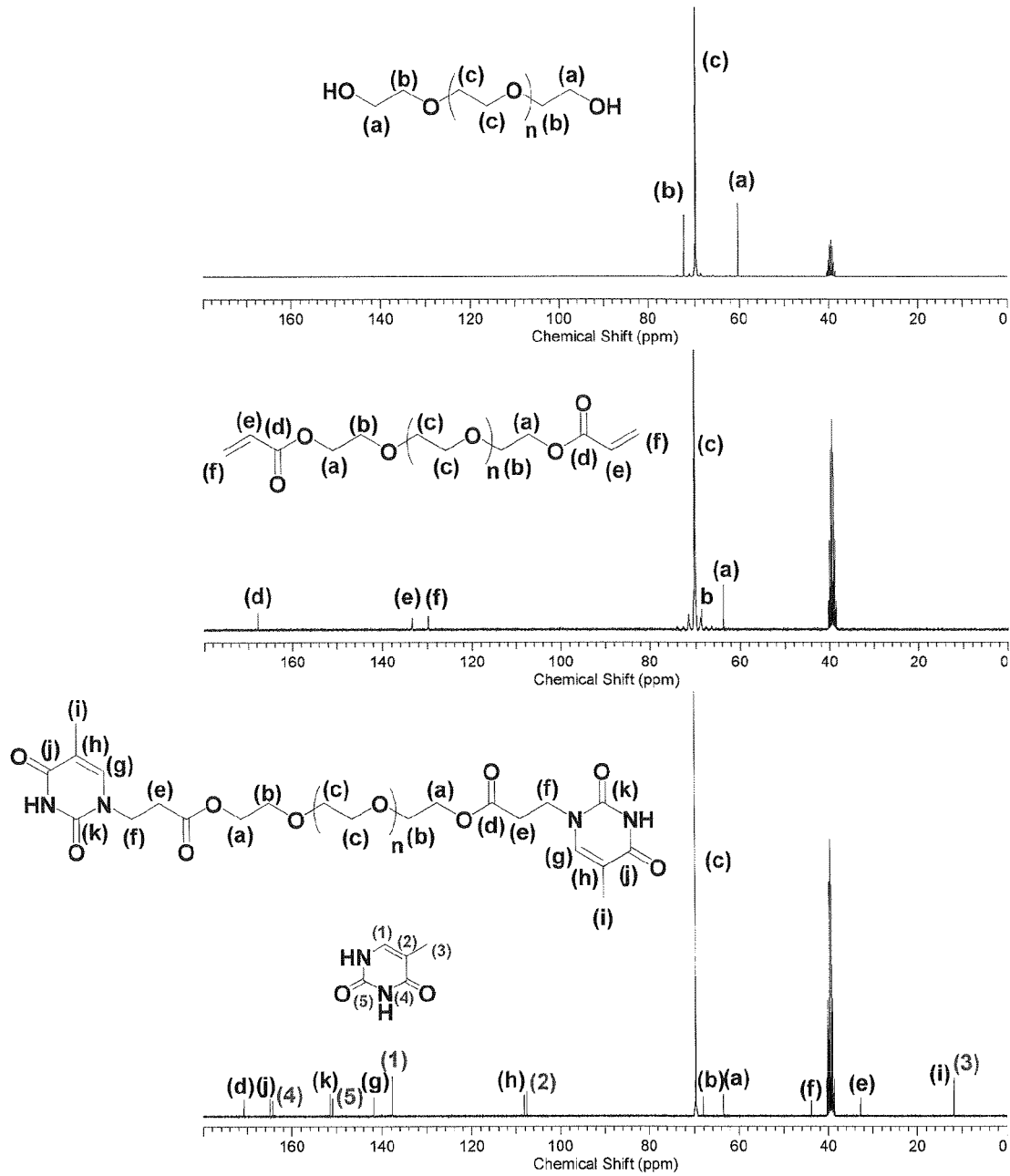
FIG. 28 are the $^{13}$C NMR spectra of the compounds prepared according to the reaction of FIG. 26, with (a) PEG ($M_n$=2,200 g/mol, $M_w/M_n$=1.23), (b) its transesterification product with vinyl acrylate, and (c) the product of Michael addition of thymine to ditelechelic PEG-acrylate (solvent: DMSO-$d_6$).

As the $^1$H NMR spectra show in FIG. 27, upon acrylation, the hydroxyl protons of the PEG precursor at δ=4.55 ppm disappeared and new peaks corresponding to the methine [δ=6.20 ppm (e)] and vinyl [δ=6.34 ppm ($f_1$) and δ=5.96 ppm ($f_2$)] are observed at the expected positions. After Michael addition, these acrylate protons disappeared and the methylene protons [δ=4.22 ppm (d)] next to the ester bond shifted upfield to δ=4.12 ppm. The integration ratios of the thymine protons [δ=11.23 ppm (1, —CO—NH—CO—), δ=7.51 ppm (j, —CH=C($CH_3$)) and δ=1.73 ppm (k, —C(CH)C(O))] and the methylene protons adjacent to the ester bond [δ=4.12 ppm (d)] are 1:1:3:2 confirming the presence of thymine. The extra set of peaks corresponded to the unreacted thymine [(1),(2),(3),(4)] which could not be removed completely from the polymer. The $^{13}$C NMR spectrum of the final product also displayed peaks consistent with the incorporation of the thymine unit at the chain end as seen in FIG. 28. The residual thymine peaks were also observed in the same spectrum.

In order to compare the catalytic activities of Amano lipase M and CALB in polymer functionalization through Michael addition, the reaction was repeated using CALB under the same reaction conditions. $^1$H NMR analysis revealed that the reaction was not complete in 72 hours as the characteristic peaks of PEG-diacrylate intermediate could still be observed. From the integral ratio, the conversion is calculated as 75.2%. Therefore, Amano lipase M was more reactive than CALB in Michael addition.

Figure 29:
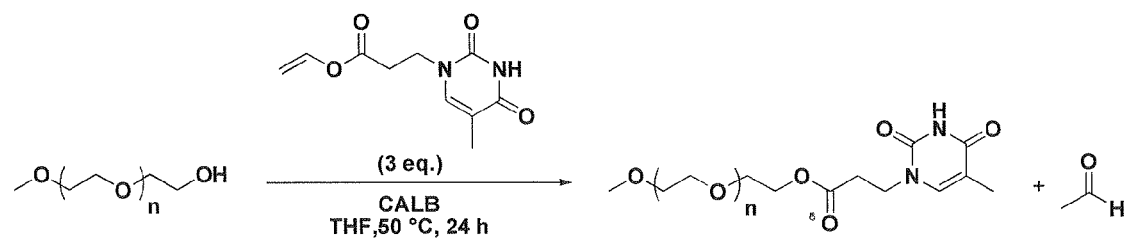
FIG. 29 shows the preparation of thymine-functionalized PEG by CALB-catalyzed transesterification with TVA.

Alternatively, the thymine unit was also attached to PEG by CALB-catalyzed transesterification of poly(ethylene glycol) monomethyl ether (mPEG-OH; $M_n$=2,250 g/mol, $M_w/M_n$=1.49) with the vinyl ester of thymine (TVA), as shown in FIG. 29, which was prepared by Michael addition of thymine to vinyl acrylate. The advantage of this strategy over the previous one is the solubility of TVA in THF which made the procedure applicable for functionalization of polymers that are not soluble in polar solvents such as DMSO. TVA was preferred over the ester prepared by the addition of thymine to vinyl methacrylate (TVMA) due to higher reactivity of TVA.

Figure 30A:
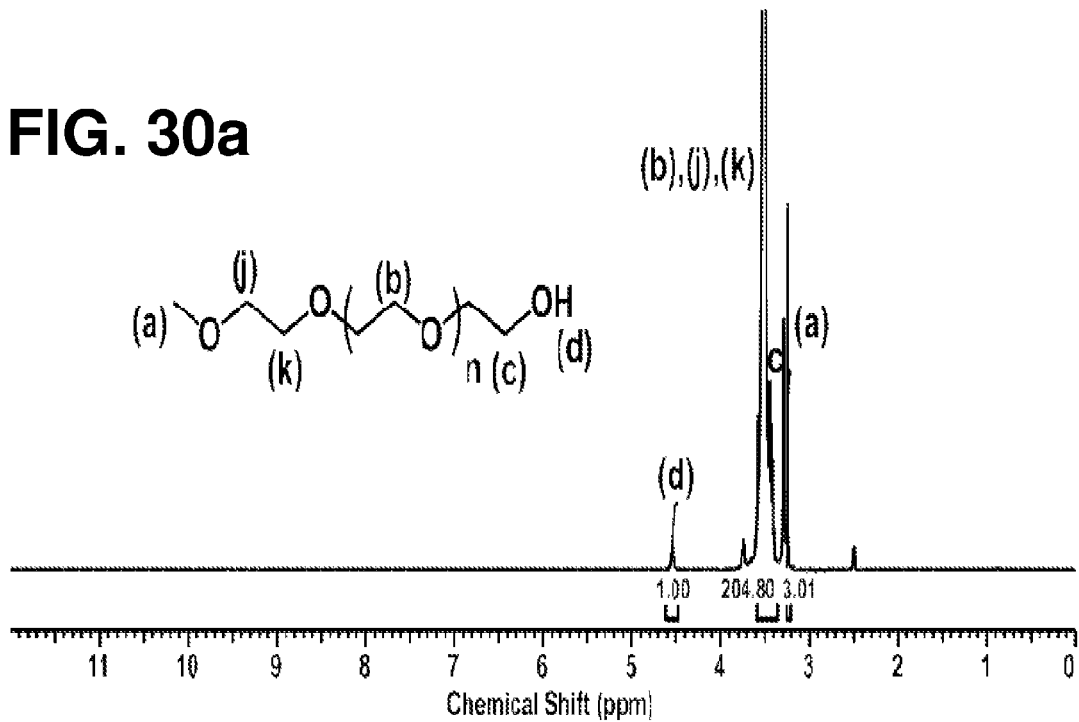
FIG. 30 shows the $^1$H NMR spectra of (a) mPEG-OH ($M_n$=2,250 g/mol, $M_w/M_n$=1.49) and (b) its transesterification product with TVA (solvent: DMSO-$d_6$).
Figure 30B:
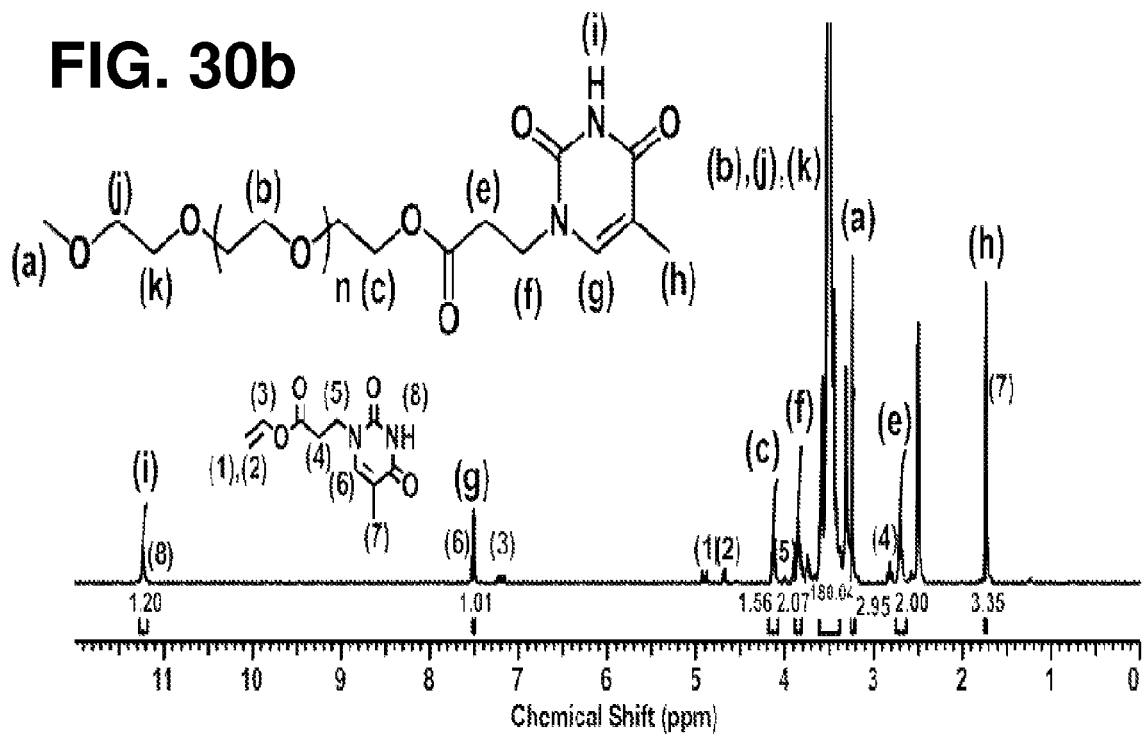

The $^1$H NMR spectrum of the product indicated the incorporation of thymine to the polymer as shown in FIG. 30. The hydroxyl protons of mPEG-OH at δ=4.54 ppm (d) disappeared and the methylene protons (c) next to the ester linkage shifted downfield to δ=4.13 ppm after the reaction. The protons corresponding to the thymine unit also appeared at the expected positions. The discrepancy in the relative integration of the thymine peaks resulted from the overlapping of the peaks of the unreacted TVA that could not be removed from the polymer.

Figure 31:
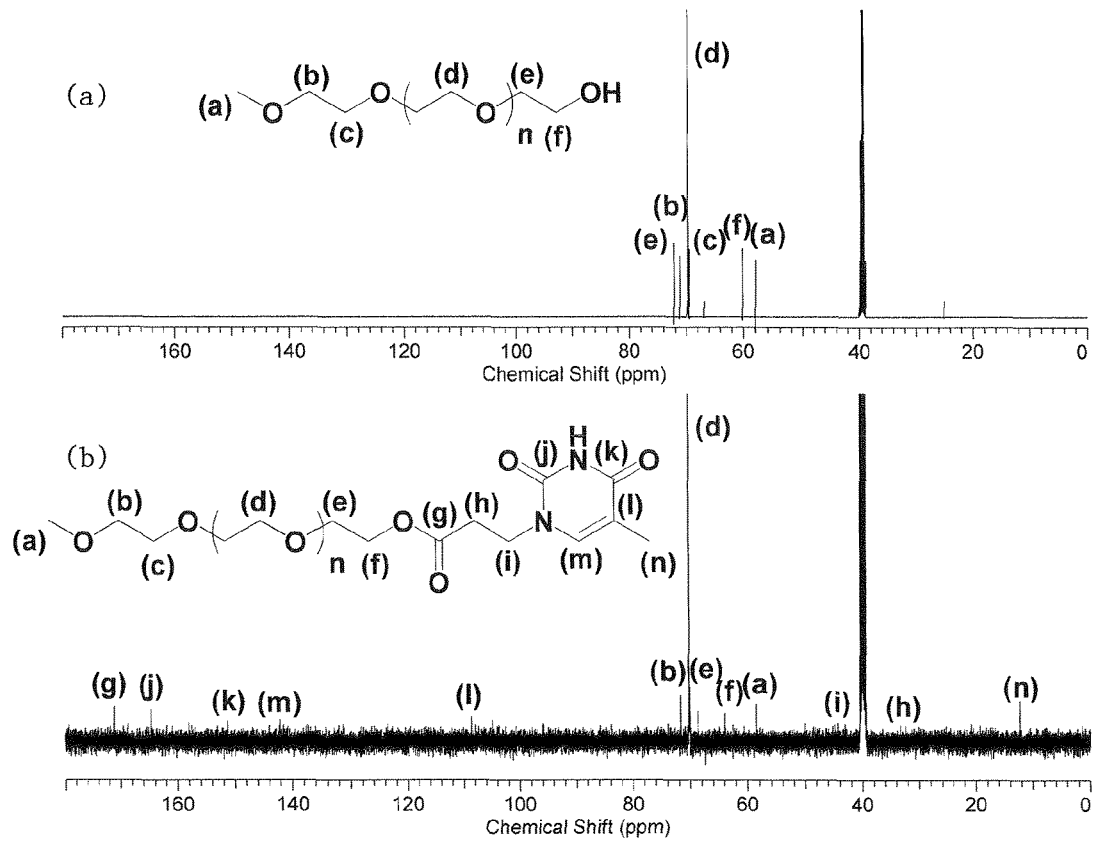
FIG. 31 shows the $^{13}$C NMR spectra of (a) mPEG-OH ($M_n$=2,250 g/mol, $M_w/M_n$=1.49) and (b) its transesterification product with TVA (solvent: DMSO-$d_6$).

The $^{13}$C NMR spectra of mPEG-OH and its transesterification product with TVA are given in FIG. 31. The resonance of the terminal methylene carbon in mPEG-OH shifted from δ=60.18 ppm (f) to δ=63.56 ppm after the attachment of thymine. The resonance of the methylene carbon adjacent to the terminal methylene carbon at δ=72.29 ppm (e) moved upfield to 63.56 ppm after the reaction. The spectrum of the product also displayed a series of peaks consistent with the incorporation of thymine to the polymer. The peak positions were in good agreement with the predictions made by ChemDraw Ultra® NMR software.

Relative to this example, both the Michael addition of thymine to acrylated PEG and transesterification of the vinyl ester of thymine (TVA) with PEG are shown to be effective ways to produce thymine-functionalized PEGs. It was also found that Amano lipase M was a more reactive catalyst as compared to CALB in PEG functionalization by Michael addition in DMSO. The presence of thymine functionality at polymer chain ends could not be further confirmed by MALDI-ToF MS due to the broad molecular weight distributions of the polymers.

Figure 32:
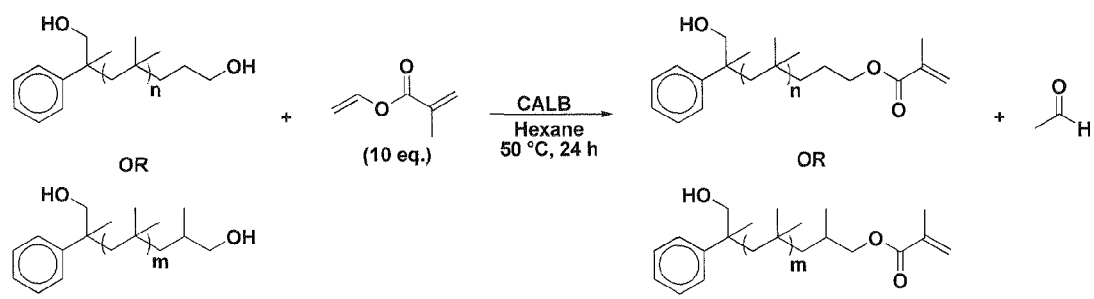
FIG. 32 shows an example of regioselective enzymatic methacrylation of asymmetric α,ω-hydroxyl-functionalized PIBs.

In accordance with a further example, the regioselectivity in enzymatic polymer functionalization is described. Both PIB-$CH_2$—$CH_2$—$CH_2$—OH and Glissopal-OH (PIB-$CH_2$—CH($CH_3$)—$CH_2$—OH) are shown to react effectively with CALB. On the other hand, the hydroxyl-functionalized PIB obtained from the α-methylstyrene epoxide (α-MSE)/$TiCl_4$ initiator system remained inactive towards the enzyme. Therefore, the asymmetric α,ω-hydroxyl-functionalized PIBs prepared with the α-MSE/$TiCl_4$ initiator system and bearing the same chain end structure at the ω-terminus as PIB-$CH_2$—$CH_2$—$CH_2$—OH and Glissopal-OH could be functionalized regioselectively at the ω-terminus. For this purpose two asymmetric α,ω-hydroxyl-functionalized PIBs, i.e. HO-PIB-$CH_2$—$CH_2$—$CH_2$—OH and HO-PIB-$CH_2$—CH($CH_3$)—$CH_2$—OH, were reacted with VMA in the presence of CALB as shown in FIG. 32.

Figure 33A:
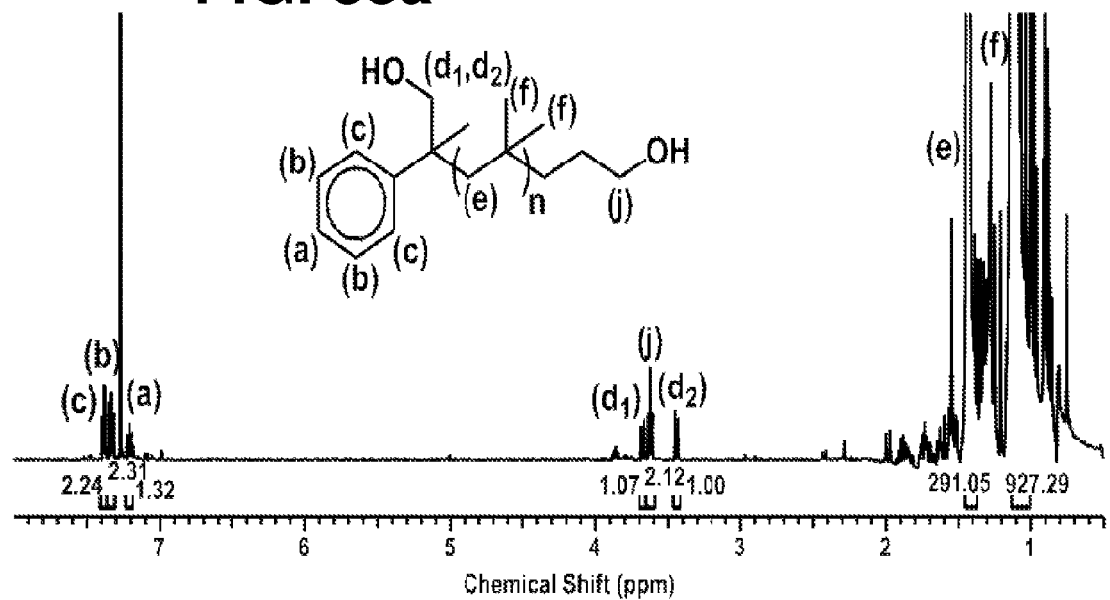
FIG. 33 shows the NMR spectra of HO-PIB-$CH_2$—$CH_2$—$CH_2$—OH: (a) $^1$H NMR spectrum and (b) $^{13}$C NMR spectrum (solvent: $CDCl_3$).
Figure 33B:
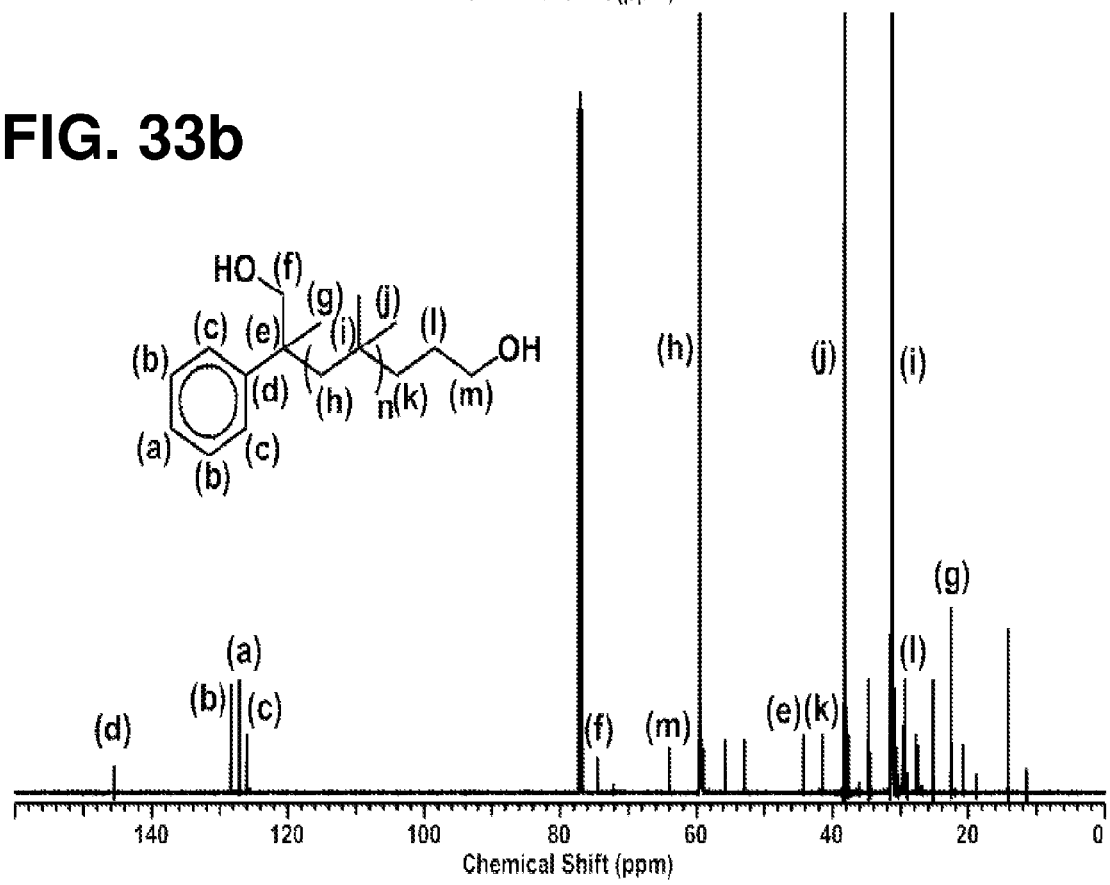

The $^1$H and $^{13}$C NMR spectra of HO-PIB-$CH_2$—$CH_2$—$CH_2$—OH are given in FIG. 33. The resonances of the methylene protons adjacent to the hydroxyl group at the α-terminus are observed at δ=3.68 ($d_1$) and 3.44 ppm ($d_2$); and the one adjacent to the hydroxyl group at the ω-terminus is observed at δ=3.63 ppm (j). The corresponding methylene carbon signals are observed at δ=74.50 ppm (f) and δ=63.98 ppm (m), respectively, in the $^{13}$C NMR spectrum.

FIG. 34 shows the $^1$H and $^{13}$C NMR spectra of the methacrylation product of HO-PIB-$CH_2$—$CH_2$—$CH_2$—OH. The methylene protons adjacent to the ω-hydroxyl end at δ=3.63 ppm (j) shifted downfield on methacrylation to δ=4.12 ppm (m) and the new signals corresponding to vinyl [δ=6.11 ($k_1$) and δ=5.55 ppm ($k_2$)] and methyl [δ=1.96 ppm (l)] protons of the methacrylate end appear at the expected positions with an integral ratio of 2:1:1:3, respectively, indicating successful conversion. The methylene protons next to the hydroxyl head group [δ=3.68 ($d_1$) and 3.44 ppm ($d_2$)], on the other hand, remained intact with relative integral values of 1.00 for $d_1$ and $d_2$ which demonstrated exclusive functionalization at the ω-terminus. The $^{13}$C NMR of the final product also displayed the peaks consistent with the incorporation of the methacrylate unit at the ω-position. The methylene carbon adjacent to the hydroxyl group at the α-terminus remained at the same position [δ=74.50 ppm (f)]. The methylene carbon next to the ω-hydroxyl chain end at δ=63.98 ppm (m) in the starting material shifted downfield to δ=65.55 ppm (s) on methacrylation and the carbonyl carbon of the methacrylate unit was observed at δ=167.46 ppm (n). The peaks at δ=136.57 (o), 125.06 (p) and 18.33 (r) ppm correspond to the α-carbon and the vinyl and methyl carbons connected to the α-carbon of the methacrylate, respectively.

Figure 35:
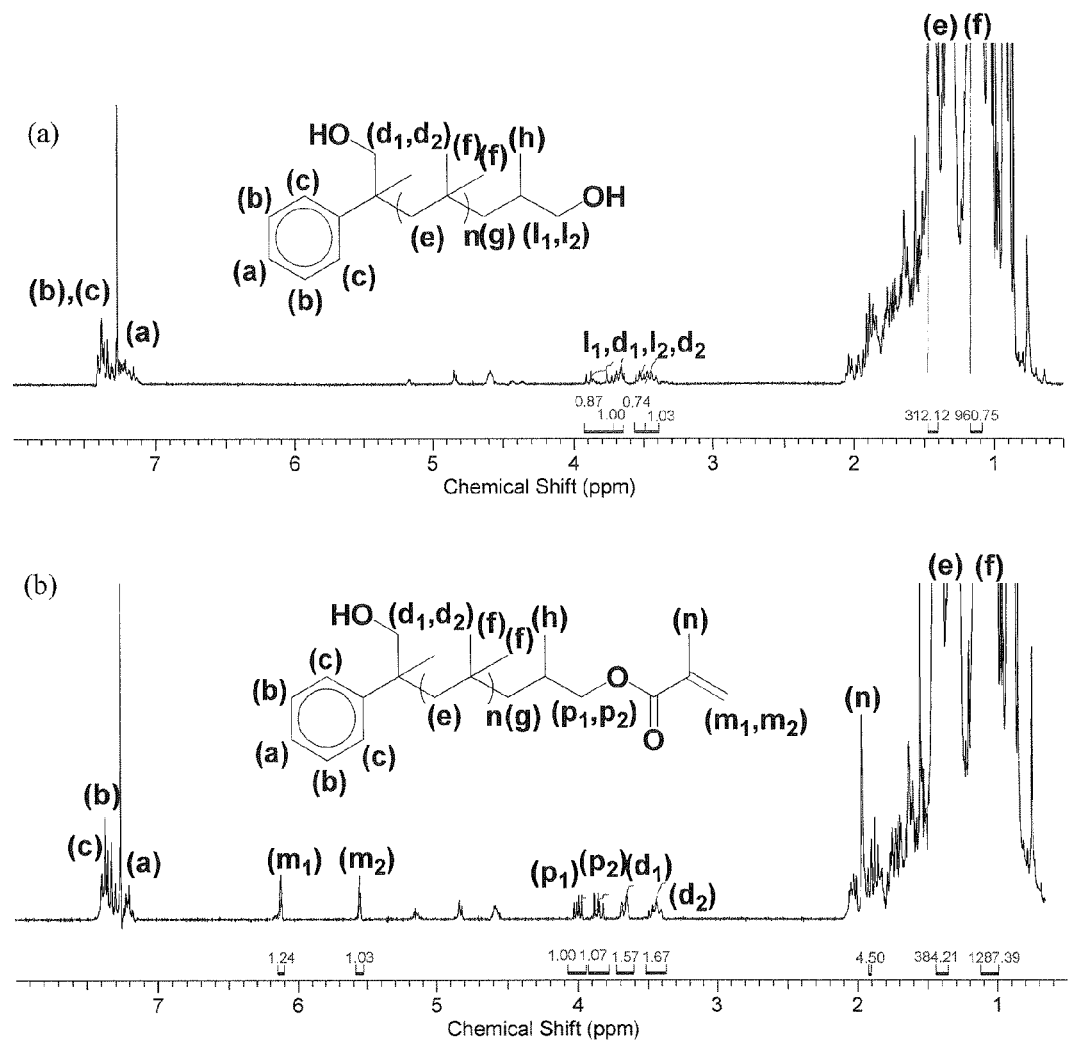
FIG. 35 shows the $^1$H NMR spectra of (a) HO-PIB-$CH_2$—CH($CH_3$)—$CH_2$—OH and (b) its methacrylation product (solvent: $CDCl_3$).

Similarly, HO-PIB-$CH_2$—CH($CH_3$)—$CH_2$—OH was also regioselectively methacrylated at the ω-terminus. As the $^1$H NMR shows in FIG. 35, the methylene protons adjacent to the hydroxyl group at the ω-end shifted from δ=3.49-3.93 ppm ($l_1$ and $l_2$) to δ=3.81-4.05 ppm ($p_1$ and $p_2$) on methacrylation and new peaks corresponding to the methacrylate endgroup are observed at the expected positions. The methylene protons next to the hydroxyl head group at δ=3.38-3.72 ppm ($d_1$ and $d_2$) remained intact.

Figure 36:
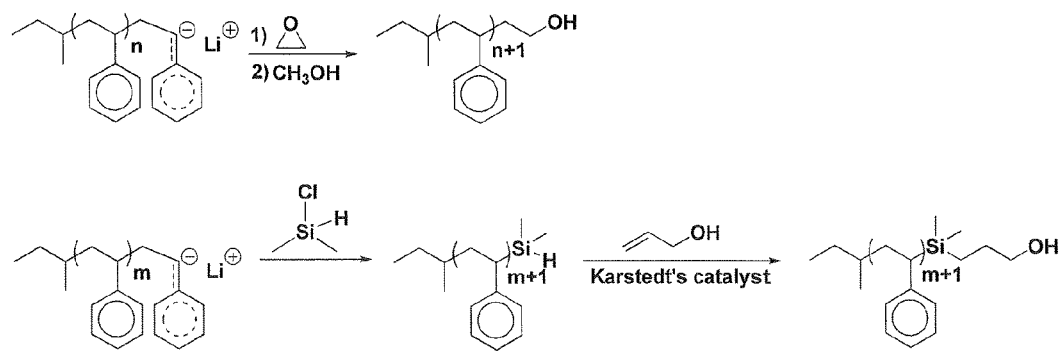
FIG. 36 shows the preparation of primary hydroxyl-functionalized polystyrenes used in enzymatic methacrylation according to an example.

Therefore, the inactivity of the hydroxyl group at the α-terminus towards the enzyme led to regioselectively methacrylated PIBs. This inactivity was apparently due to the steric hindrance around the hydroxyl head group created by the phenyl ring. The effect of steric hindrance was further demonstrated using two primary hydroxyl-functionalized polystyrenes with different chain end structures: one was a commercial product (from Polymer Source Inc.) prepared by end-capping of poly(styryl)lithium with ethylene oxide (PS—CH$_2$—CH$_2$—OH); and the other one was previously synthesized via end-capping of poly(styryl)lithium with chlorodimethylsilane followed by hydrosilation with allyl alcohol which led to a spacer between the last styrene unit and the 2-hydroxyethyl chain end (PS-Si(CH$_3$)$_2$—CH$_2$—CH$_2$—CH$_2$—OH), as shown in FIG. 36.

Figure 37:
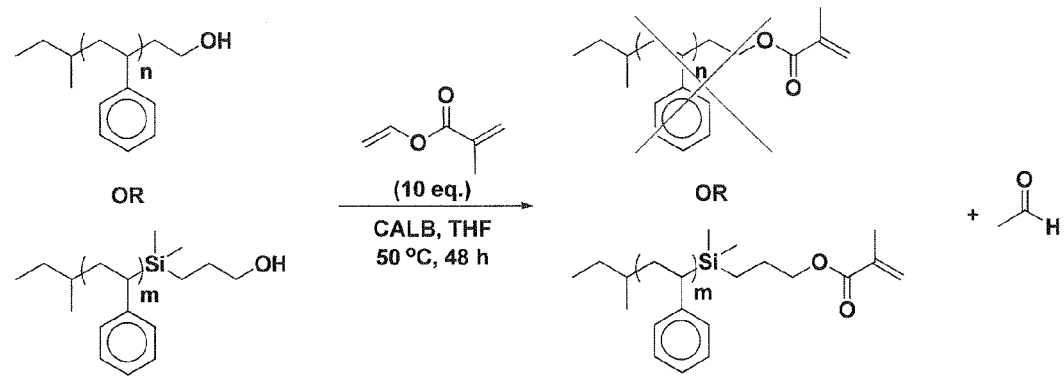
FIG. 37 shows the transesterification of VMA with hydroxyl-functionalized polystyrenes: (a) unsuccessful reaction with PS-$CH_2$—$CH_2$—OH and (b) quantitative reaction with PS-Si($CH_3$)$_2$—$CH_2$—$CH_2$—$CH_2$—OH.

The two polymers were reacted with about 10 equivalents of VMA in THF in the presence of CALB as seen in FIG. 37; and the reactions were monitored with TLC using toluene as the eluent. It was observed that there was no progress in the reaction with the PS-CH$_2$—CH$_2$—OH as the spot corresponding to hydroxyl-functionalized polymer at R$_f$=0.2 remain unchanged. On the other hand, the TLC analysis of the methacrylation of PS-Si(CH$_3$)$_2$—CH$_2$—CH$_2$—CH$_2$—OH indicated that the spot at R$_f$=0.2 corresponding to the starting material disappeared within 48 hours and a new spot formed at R$_f$=0.7. The analysis of both the PS-Si(CH$_3$)$_2$—CH$_2$—CH$_2$—CH$_2$—OH and its methacrylation product are discussed below.

Figure 38:
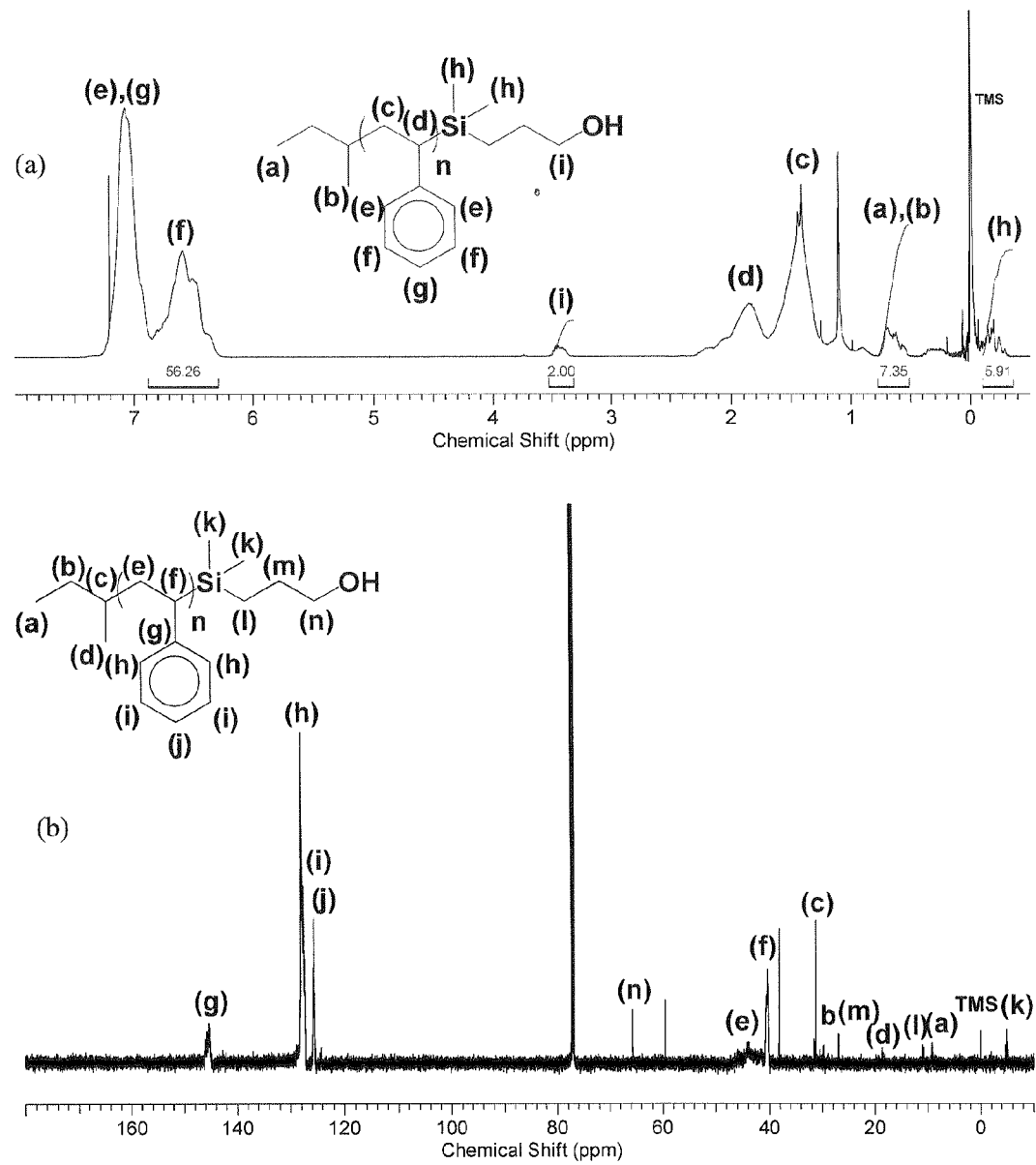
FIG. 38 shows the NMR spectra of PS-Si($CH_3$)$_2$—$CH_2$—$CH_2$—$CH_2$—OH: (a) $^1$H NMR spectrum and (b) $^{13}$C NMR spectrum (solvent: $CDCl_3$).
Figure 39:
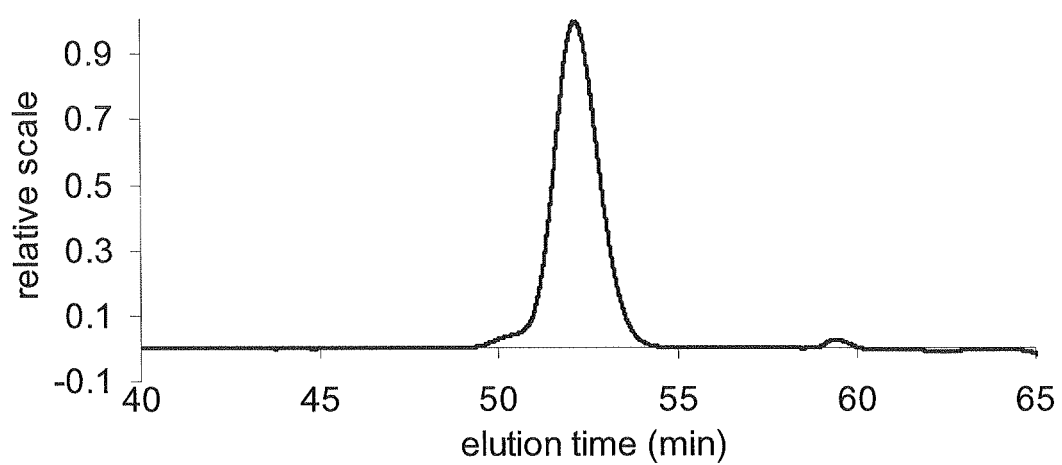
FIG. 39 shows the SEC chromatogram of PS-Si($CH_3$)$_2$—$CH_2$—$CH_2$—$CH_2$—OH.

The $^1$H and $^{13}$C NMR spectra of PS-Si(CH$_3$)$_2$—CH$_2$—CH$_2$—CH$_2$—OH are given in FIG. 37. The peak at δ=3.34-3.53 ppm (i) is attributed to the methylene protons next to the hydroxyl group. The integral ratios between these two protons, six methyl protons coming from the sec-BuLi initiator and six methyl protons coming from the methyl groups attached to silicon are 2.00:7.35:5.91 which are close to the expected ratios of 2:6:6. The SEC analysis of this polymer revealed the presence of a small amount of high molecular weight polymer as seen in FIG. 38.

In the $^{13}$C NMR spectrum shown in FIG. 37, the resonance corresponding to the methylene carbon next to the hydroxyl group is observed at δ=65.69 ppm (n). All the other carbon signals except those at δ=38.0 and 60.0 ppm could be assigned to the structure. These unidentified peaks may come from an impurity.

Figure 40:
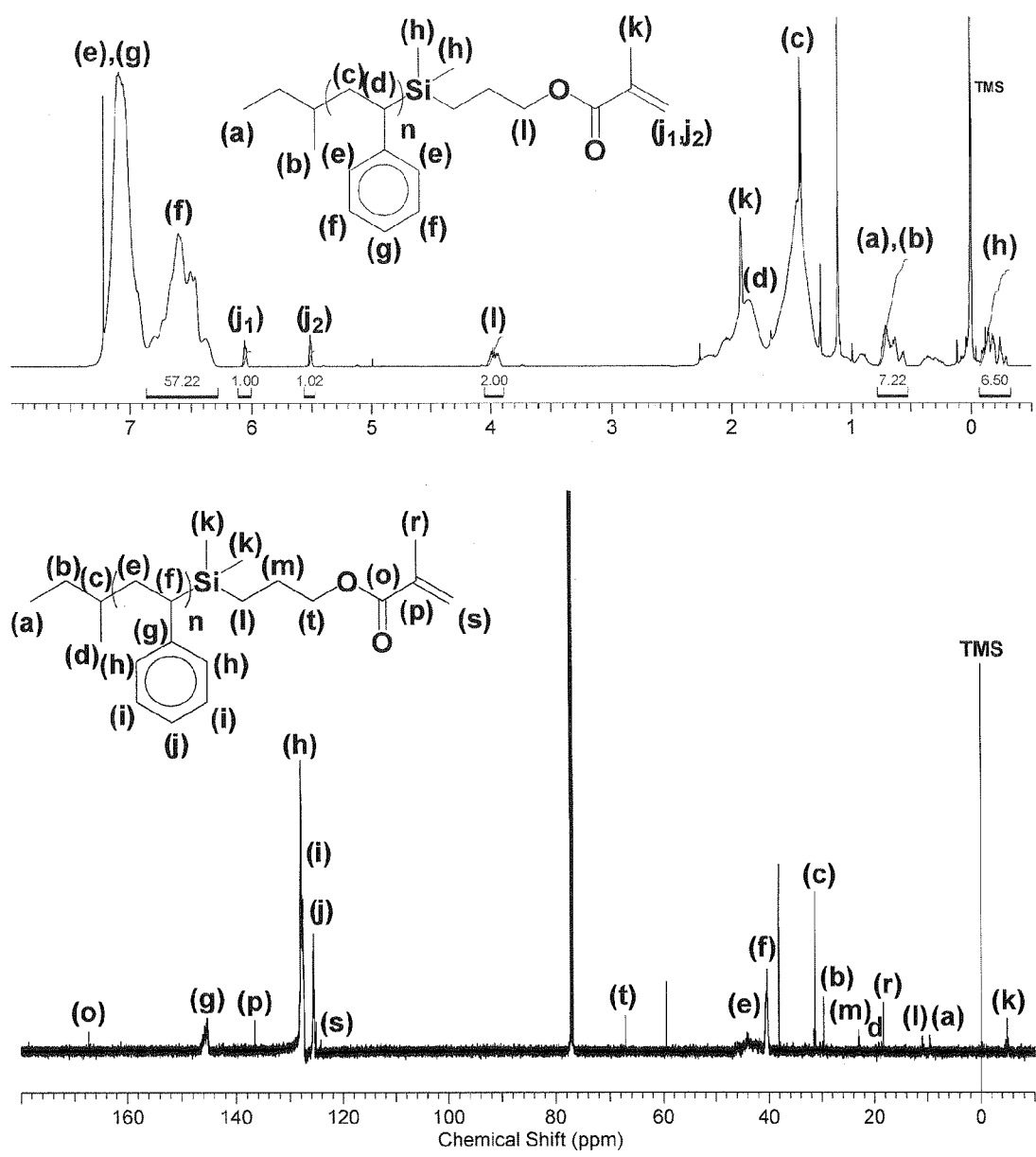
FIG. 40 shows the NMR spectra of the methacrylation product of PS-Si($CH_3$)$_2$—$CH_2$—$CH_2$—$CH_2$—OH: (a) $^1$H NMR spectrum and (b) $^{13}$C NMR spectrum (solvent: $CDCl_3$).

The $^1$H and $^{13}$C NMR spectra of the methacrylation product of this polymer are shown in FIG. 40. The peak corresponding to the methylene protons next to the hydroxyl group at δ=3.34-3.53 ppm (i) shifted downfield to δ=3.89-4.05 ppm (l) after the reaction and new peaks were observed at 6.05 ppm (j$_1$) and δ=5.51 ppm (j$_2$) and δ=1.93 ppm (k), corresponding to the vinyl and methyl protons of the methacrylate end, respectively.

$^{13}$C NMR spectroscopy also confirmed the incorporation of methacrylate unit at the chain end. The resonance at δ=65.69 ppm (n) corresponding to the methylene carbon next to the oxygen atom in the starting material shifted downfield to δ=67.13 ppm (t) after the reaction. The resonance of the carbonyl carbon of methacrylate group appear at δ=167.41 ppm (o) and the resonances of vinyl, methyl and α-carbons of the methacrylate end are observed at δ=125.09 (s), 18.34 (r), and 136.58 ppm (p), respectively.

Figure 41:
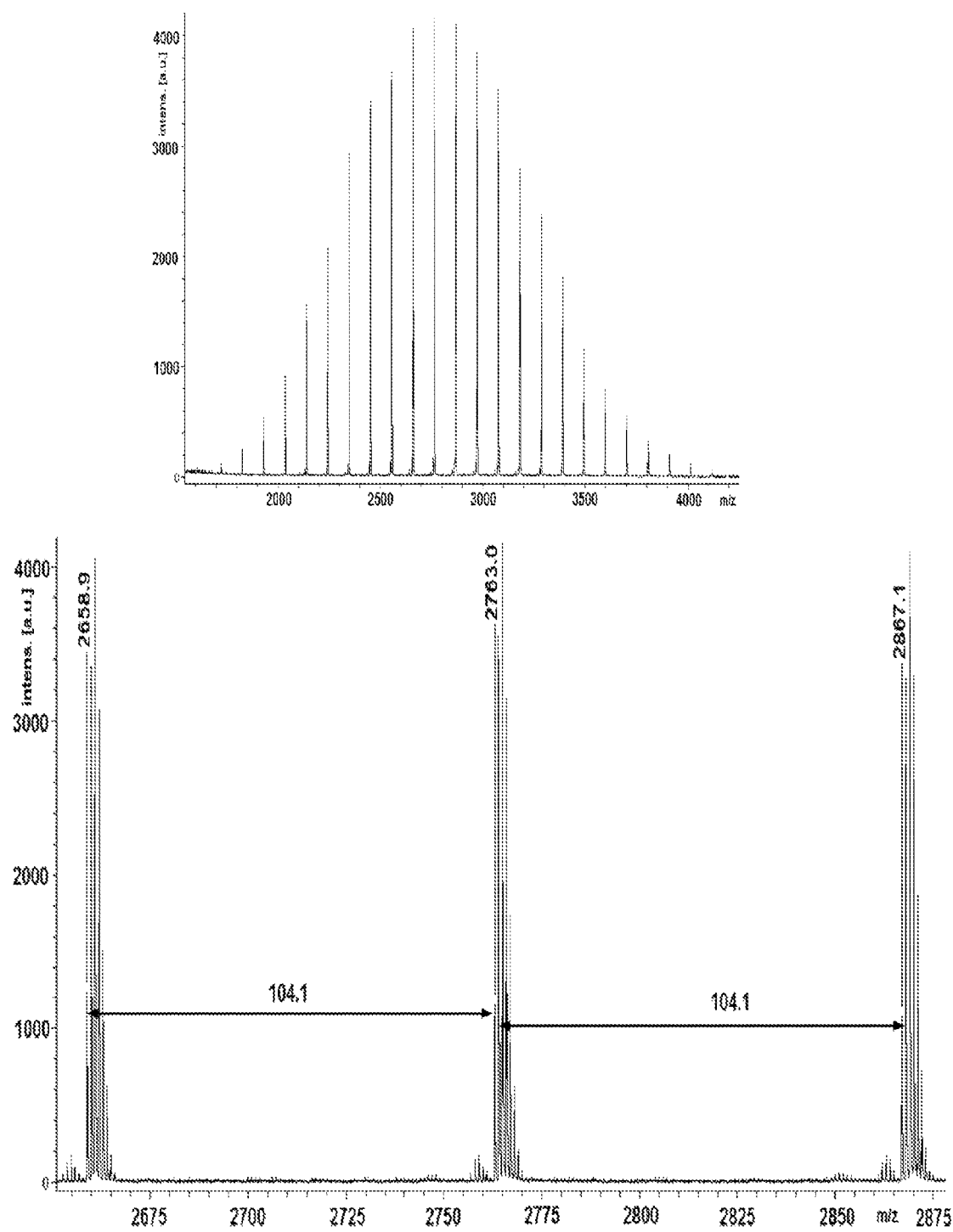
FIG. 41 shows the MALDI-ToF mass spectrum of the methacrylation product of PS-Si($CH_3$)$_2$—$CH_2$—$CH_2$—$CH_2$—OH.

Further evidence for the quantitative methacrylation was provided by MALDI-ToF MS analysis using dithranol and sodium trifluoroacetate as matrix and cationizing salt, respectively, with a ratio of 10:1:2 (matrix:cationizing salt:polymer), with reference to FIG. 41. The representative peak at m/z=2763.0 corresponds to the monoisotopic mass of the sodiated 24-mer of methacrylated polystyrene. The calculated monoisotopic mass for this peak [m/z=57.07 (C$_4$H$_9$ head group)+24×104.06 (C$_8$H$_8$ repeat unit)+185.10 (C$_9$H$_{17}$O$_2$Si end group)+22.99 (Na$^+$)] is 2762.60 Da. The mass between two consecutive peaks is equal to 104.1, which corresponds to the mass of one styrene repeat unit. Therefore, the introduction of the (—Si(CH$_3$)$_2$—CH$_2$—) spacer between the last styrene unit and the 2-hydroxyethyl chain end (—CH$_2$—CH$_2$—OH) rendered the PS reactive for enzymatic methacrylation. On the other hand, the fact that the hydroxyl-functionalized PIBs having a methyl group at the close proximity of the terminal methylene group [PIB-CH$_2$—CH(CH$_3$)—CH$_2$—OH] reacted quite effectively with the enzyme while PS with no methyl groups close to hydroxyl end (PS-CH$_2$—CH$_2$—OH) showed no activity could not be explained.

Figure 42:
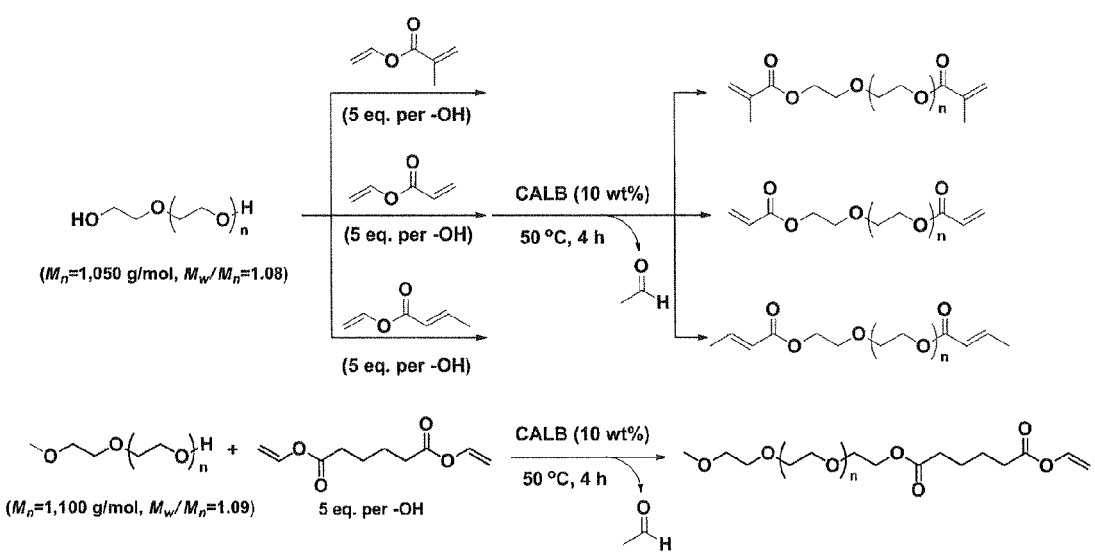
FIG. 42 shows the scheme for transesterification of vinyl esters with PEGs in bulk condition according to an example.

A further example of the invention is shown regarding the synthesis of PEG-diacrylate, PEG-dimethacrylate, PEG-dicrotonate and PEG-vinyl adipate in bulk condition. PEG-diacrylate, PEG-dimethacrylate, PEG-dicrotonate and PEG-vinyl adipate were prepared by the transesterification of vinyl acrylate (VA), vinyl methacrylate (VMA), divinyl adipate (DVA) and vinyl crotonate (VC) with PEGs in bulk in the presence of CALB, respectively, as shown in FIG. 42. Monitoring the reaction with $^1$H and $^{13}$C NMR revealed that the reaction was quantitative within 4 hours when 5 equivalents of vinyl esters per OH group in PEGs was used.

Figure 43:
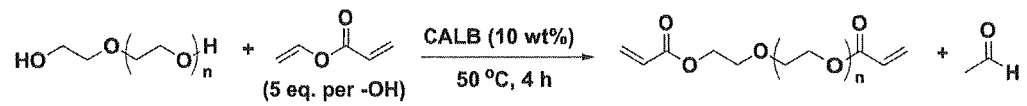
FIG. 43 shows the scheme for transesterification of vinyl acrylate with HO-PEG-OH in bulk.

In another example, the synthesis of PEG-diacrylate by transesterification of VA with HO-PEG-OH in bulk in shown in FIG. 43. In this example, 0.3405 g of HO-PEG-OH (0.3243 mmol, 1050 g/mol), 40 mg of CALB (~10 wt % relative to HO-PEG-OH) and 0.2963 g of VA (3.020 mmol, 5 eq. per —OH) were added in a flask. The HO-PEG-OH was able to dissolve in VA. The reactants were purged with Ar. The reaction was stirred for 4 hours at 50° C. The liquid product was dissolved in 5 mL of THF and the CALB was filtered out using 0.45 μm syringe filter. The product solution was precipitated in 200 mL of hexane and diethyl ether mixture (1:1 ratio). The white precipitate was collected and dried using vacuum pump.

Figure 44:
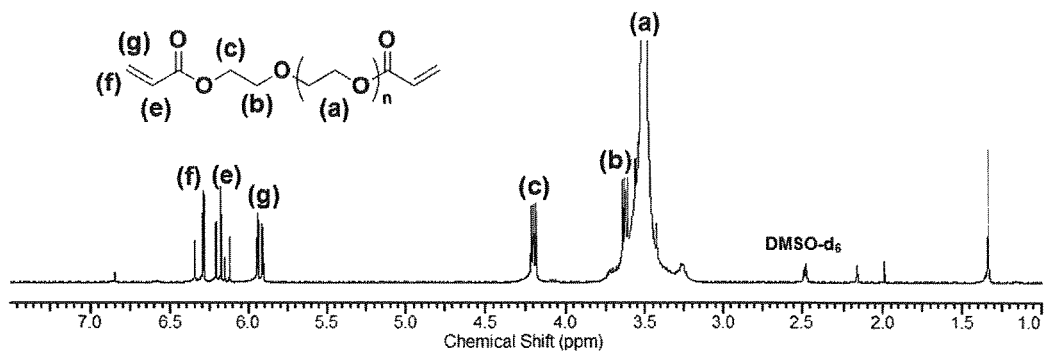
FIG. 44 shows the $^1$H NMR spectrum of the acrylation product of a HO-PEG-OH ($M_n$=1000 g/mol, $M_w/M_n$=1.08) in bulk after 4 hours of reaction time (NMR solvent: DMSO-$d_6$).

The product of the synthesis provides the $^1$H NMR spectrum of was FIG. 44, wherein it shows the PEG-diacrylate. The hydroxyl protons at δ=4.55 ppm from the HO-PEG-OH completely disappeared and the peak corresponding to the methylene protons adjacent to hydroxyl group shifted downfield from δ=3.50 to δ=4.42 ppm (c) after the reaction. The new peaks corresponding to the methine [δ=6.19 ppm (e)] and vinyl [δ=6.38 ppm (f) and δ=5.92 ppm (g)] protons of the acrylate group were observed at the expected positions with integral values of 2:1:1:1 [(c):(e):(f):(g)] confirming successful functionalization.

Figure 45:
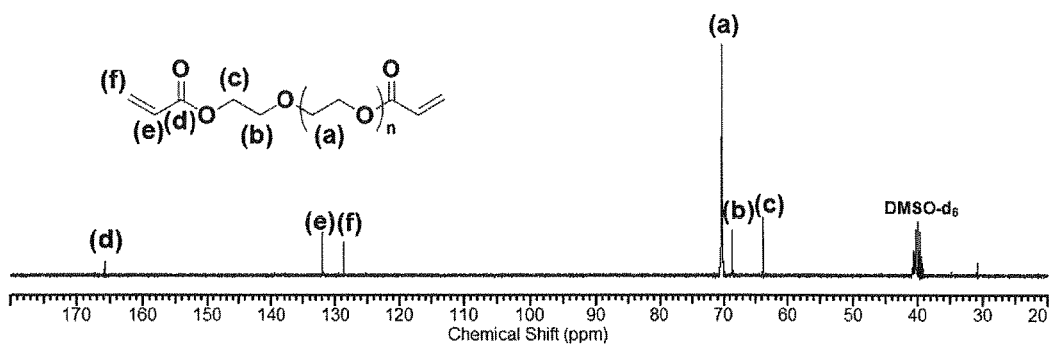
FIG. 45 shows the $^{13}$C NMR spectrum of the acrylation product of a HO-PEG-OH ($M_n$=1000 g/mol, $M_w/M_n$=1.08) in bulk after 4 hours of reaction time (NMR solvent: DMSO-$d_6$).

The $^{13}$C NMR spectrum of the acrylation product also confirmed the structure of the polymer as shown in FIG. 45. The carbons connected to the hydroxyl group in the starting material at δ=60.13 ppm shifted downfield to δ=63.89 ppm (c) after the reaction and the carbon resonances of the acrylate group appeared at δ=165.87 ppm (d), δ=132.01 ppm (e) and δ=128.66 ppm (f) corresponding to carbonyl carbon, α-carbon and the vinyl carbons connected to the α-carbon, respectively.

Figure 46:
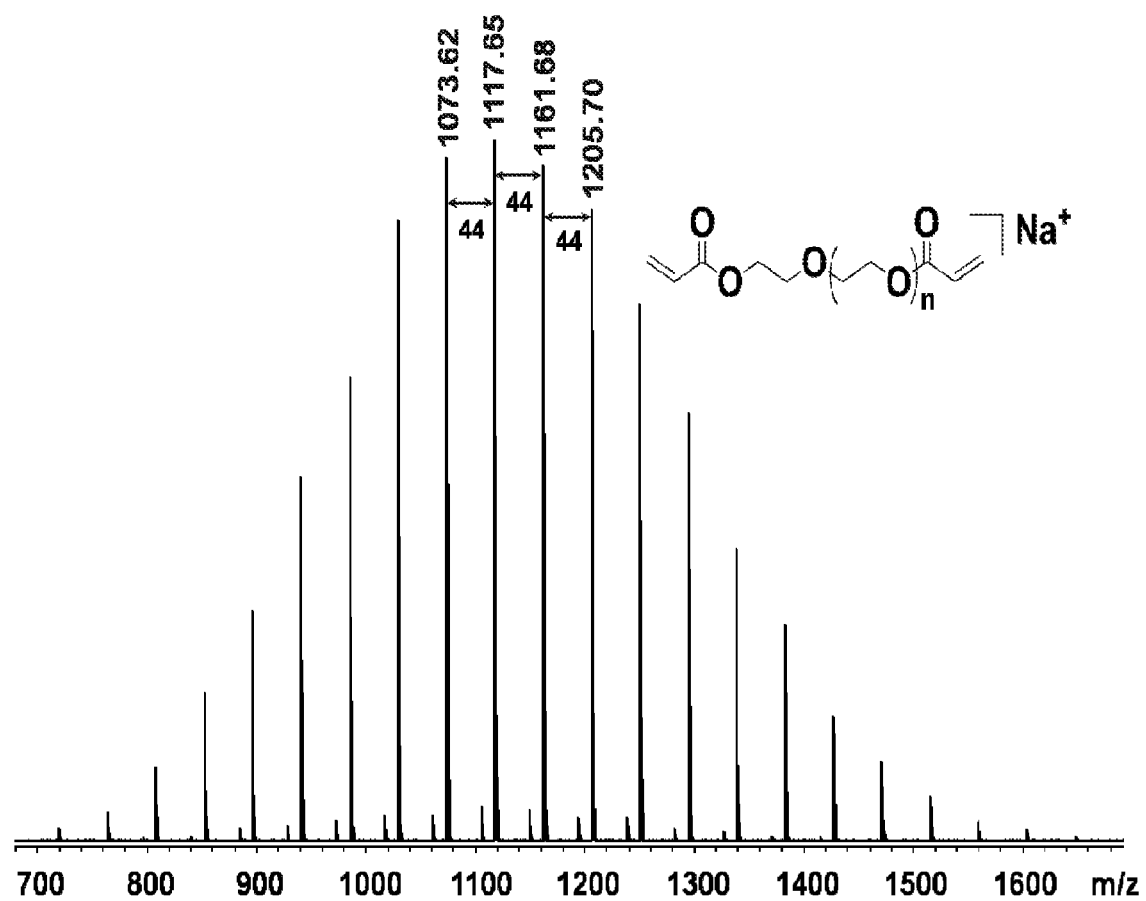
FIG. 46 shows the MALDI-ToF mass spectrum of the PEG-diacrylate product (cationizing salt: sodium trifluoroacetate).
Figure 47:
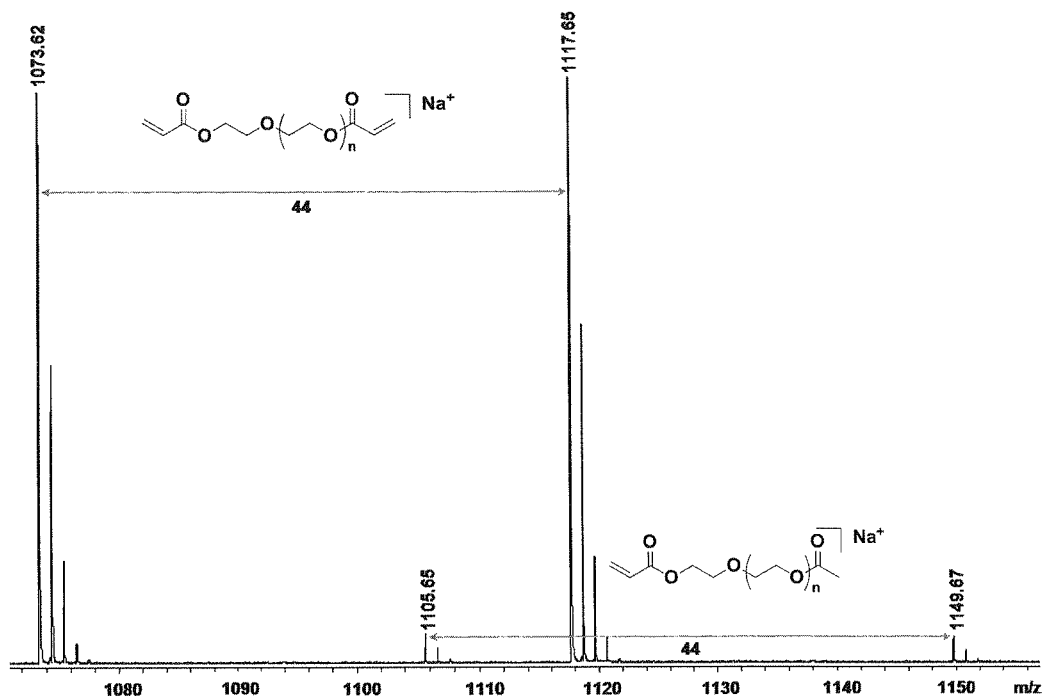
FIG. 47 shows the magnification of MALDI-ToF mass spectrum of the PEG-diacrylate product (cationizing salt: sodium trifluoroacetate).

MALDI-ToF mass spectrometry was also utilized for further confirmation of the chain end structure. A single product with the expected structure was observed as indicated in FIG. 46. For example, the peak at m/z 1073.62 corresponds to the sodium complex of the 21-mer of PEG-arcylate. The calculated monoisotopic mass for this peak is [21×44.03 (C$_2$H$_4$O repeat unit)+126.11 (C$_6$H$_6$O$_3$ end groups)+22.99 (Na$^+$)] 1073.73 Da. Within the series the peaks were separated by m/z 44, corresponding to an ethylene glycol repeating unit. Upon a closer examination, a minor set of peaks which differ from the main series by 12 m/z units were observed (See FIG. 47). This pattern can be attributed to acrylate-PEG-acetate which may form by the reaction of the polymer with vinyl acetate, the starting material used in the production of VA.

Figure 48:
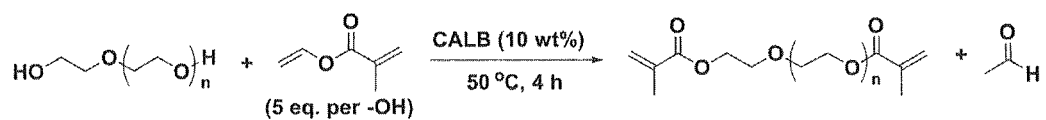
FIG. 48 shows a scheme for transesterification of VMA with HO-PEG-OH in bulk.

In another example, the synthesis of PEG-dimethacrylate by transesterification of vinyl methacrylate with HO-PEG-OH in bulk is shown in FIG. 48. In this example, 0.5109 g of HO-PEG-OH (0.4865 mmol) was dissolved in 0.5561 g of vinyl methacrylate (4.959 mmol, ~5 eq per —OH). 52 mg of CALB (~10 wt % relative to HO-PEG-OH) was added in the reactant, followed by purging it with Ar gas. The reaction was stirred for 4 hours at 50° C. The liquid product was dissolved in 5 mL of THF and the CALB was filtered out using 0.45 μm syringe filter. The product solution was precipitated in 200 mL of hexane and diethyl ether mixture (1:1 ratio). The white precipitate was collected and dried using vacuum pump.

Figure 49:
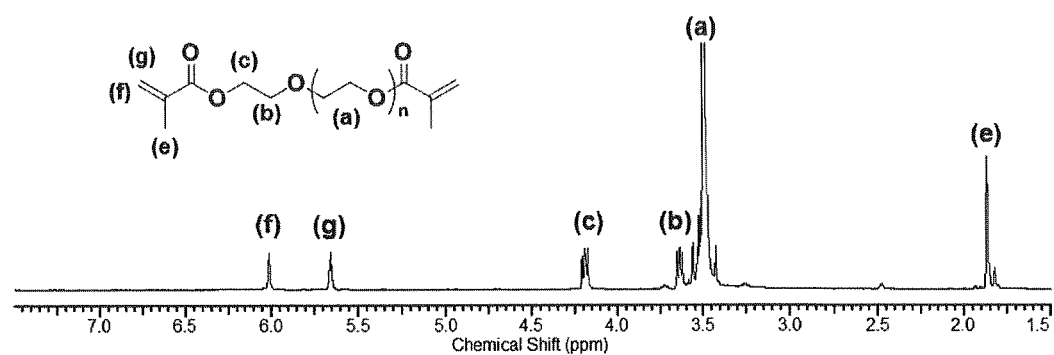
FIG. 49 shows the $^1$H NMR spectrum of the methacrylation product of a HO-PEG-OH ($M_n$=1000 g/mol, $M_w/M_n$=1.08) in bulk after 4 hours of reaction time (NMR solvent: DMSO-$d_6$).

The $^1$H NMR spectrum of the PEG-dimethacrylate is shown in FIG. 49. The hydroxyl protons at δ=4.55 ppm from the HO-PEG-OH completely disappeared and the peak corresponding to the methylene protons adjacent to hydroxyl group shifted downfield from δ=3.50 to δ=4.42 ppm (c) after the reaction. The new peaks corresponding to the methyl [δ=1.73 ppm (e)] and vinyl [δ=6.07 ppm (f) and δ=5.81 ppm (g)] protons of the methacrylate group were observed at the expected positions with integral values of 2:3:1:1 [(c):(e):(f):(g)] confirming successful functionalization.

Figure 50:
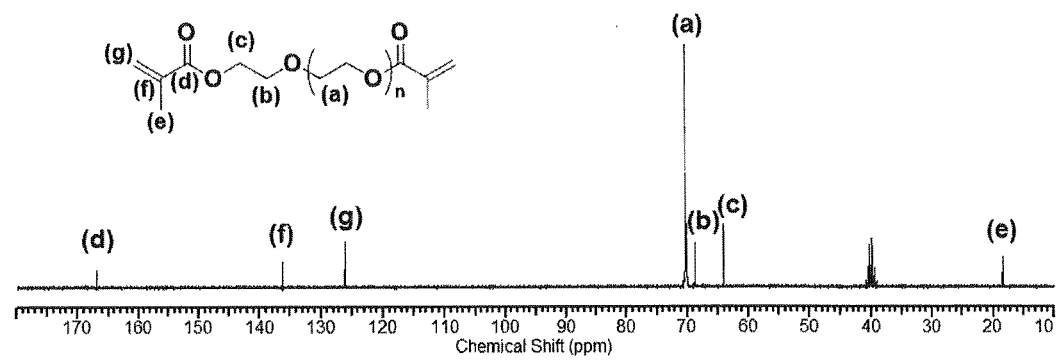
FIG. 50 shows the $^{13}$C NMR spectrum of the methacrylation product of a HO-PEG-OH ($M_n$=1000 g/mol, $M_w/M_n$=1.08) in bulk after 4 hours of reaction time (NMR solvent: DMSO-$d_6$).

The $^{13}$C NMR spectrum of the methacrylation product is shown in FIG. 50 and also confirmed the structure of the polymer. The carbons connected to the hydroxyl group in the starting material at δ=60.13 ppm shifted downfield to δ=63.89 ppm (c) after the reaction and the carbon resonances of the methacrylate group appeared at δ=166.97 ppm (d), δ=18.12 ppm (e), δ=136.24 ppm (f) and δ=126.11 ppm (g) corresponding to carbonyl carbon, methyl carbon, α-carbon and the vinyl carbons connected to the α-carbon, respectively.

Figure 51:
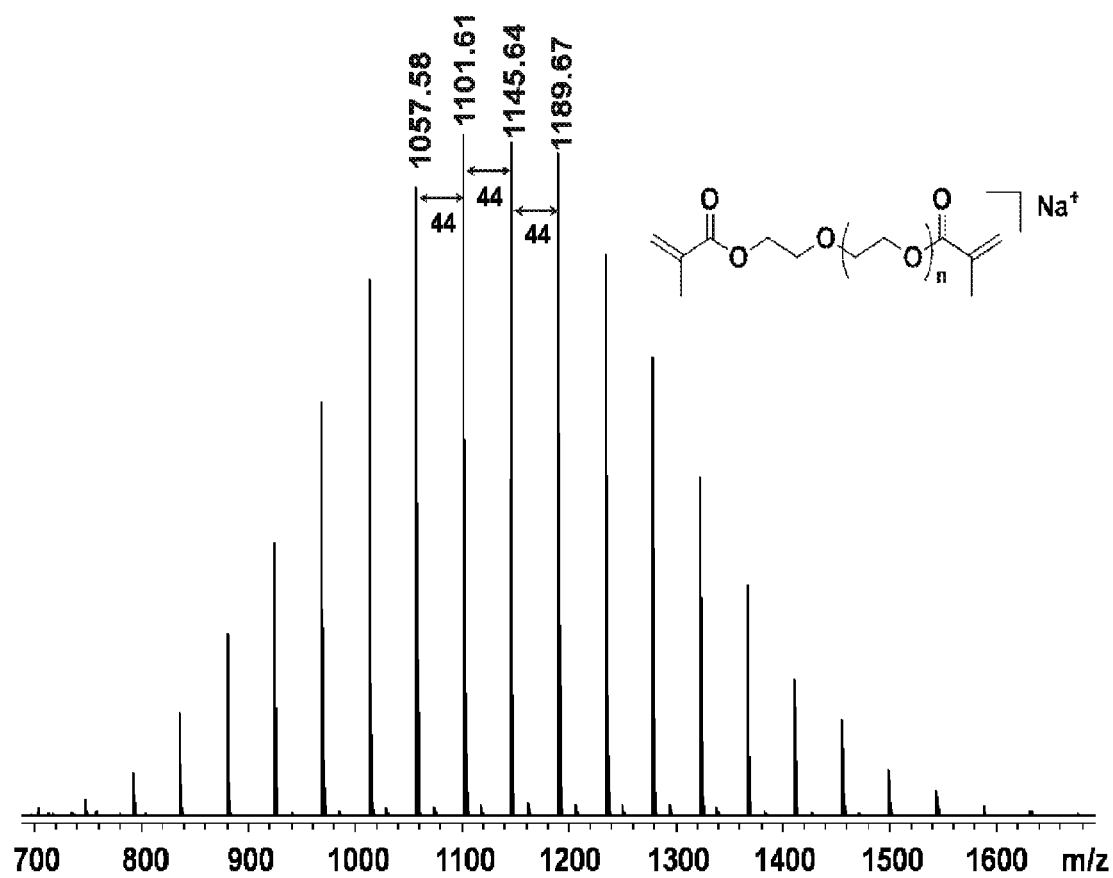
FIG. 51 shows the MALDI-ToF mass spectrum of the PEG-dimethacrylate product (cationizing salt: sodium trifluoroacetate).
Figure 52:
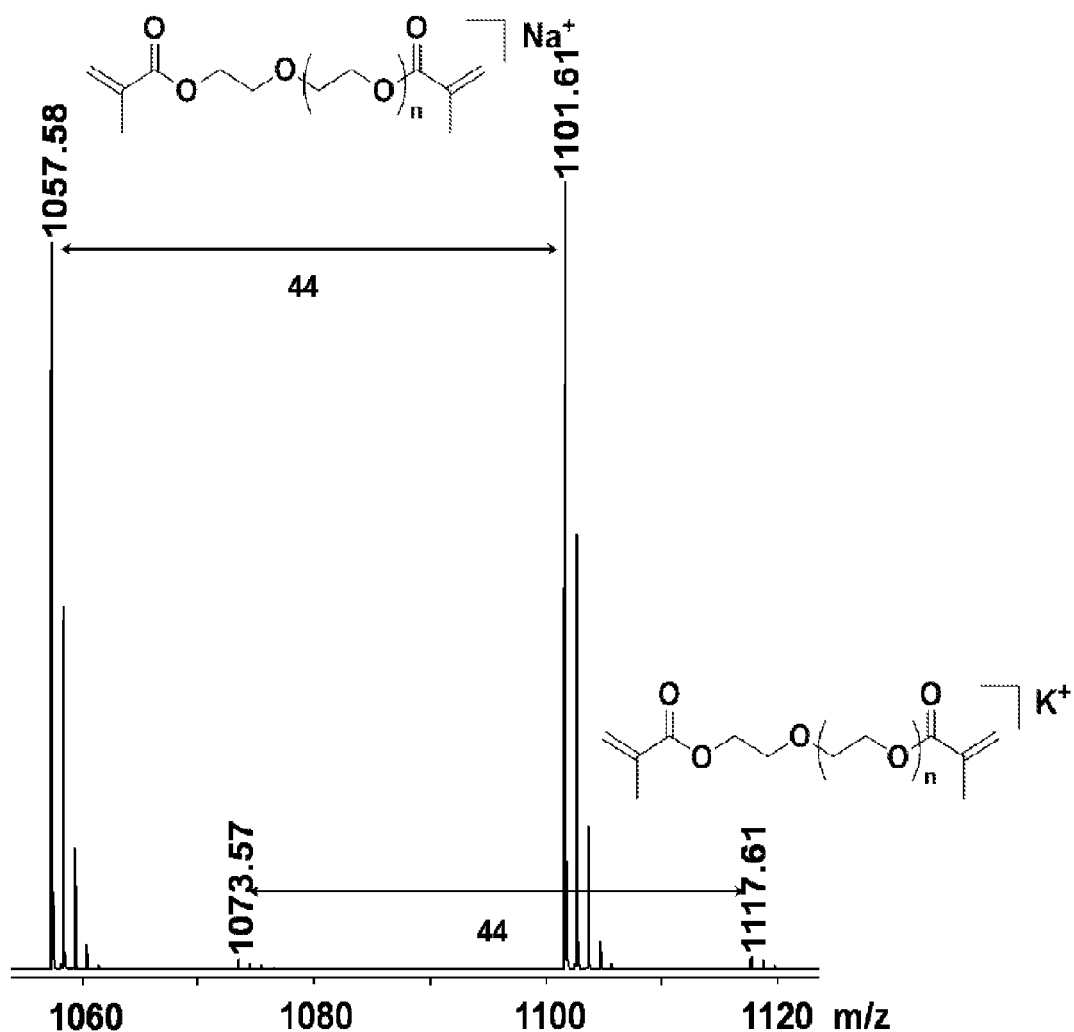
FIG. 52 shows the magnification of MALDI-ToF mass spectrum of the PEG-dimethacrylate product (cationizing salt: sodium trifluoroacetate).

In the MALDI-ToF MS of the product, a single distribution corresponding to the expected structure was observed as indicated in FIG. 51. For example, the peak at m/z 1101.61 corresponds to the sodium complex of the 21-mer of PEG-dimethacrylate. The calculated monoisotopic mass for this peak is [21×44.03 ($C_2H_4O$ repeat unit)+154.08 ($C_8H_{10}O_3$ end groups)+22.99 (Na$^+$)] 1101.70 Da. Within the series the peaks were separated by m/z 44, corresponding to an ethylene glycol repeating unit. Upon a closer examination, minor distributions of peaks which differ from the main series by 16 m/z units were observed (FIG. 52). This can be attributed to the K$^+$ cationized PEG-dimethacrylate as it is known that K$^+$ contamination could occur during sample preparation and the mass difference between Na$^+$ and K$^+$ is 16 amu. Therefore, MALDI-ToF MS analysis confirmed that the conversion of HO-PEG-OH to PEG-dimethacrylate was quantitative within 4 hours of reaction time in bulk.

Figure 53:
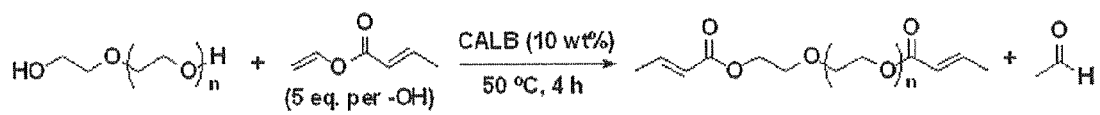
FIG. 53 shows a scheme for transesterification of VC with HO-PEG-OH in bulk.

According to a further example, the synthesis of PEG-dicrotonate by transesterification of vinyl crotonate (VC) with HO-PEG-OH in bulk is shown in FIG. 53. In this example, 0.409 g of HO-PEG-OH (0.389 mmol) was dissolved in 0.427 g of VC (3.808 mmol, ~5 eq per —OH). 42 mg of CALB (~10 wt % compared to HO-PEG-OH) was added in the reactant, followed by purging it with Ar gas. The reaction was stirred for 4 hours at 50° C. The liquid product was dissolved in 5 mL of THF and the CALB was filtered out using 0.45 μm syringe filter. The product solution was precipitated in 200 mL of hexane and diethyl ether mixture (1:1 ratio), The white precipitate was collected and dried using vacuum pump.

Figure 54:
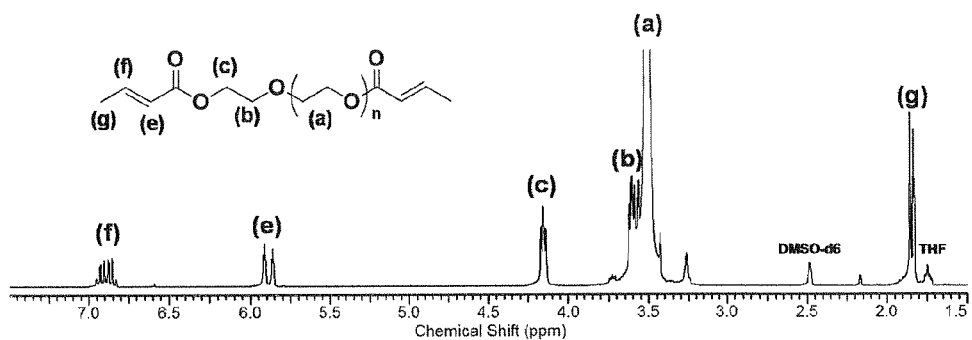
FIG. 54 shows the $^1$H NMR spectrum of the PEG-dicrotonate in bulk after 4 hours of reaction time (NMR solvent: DMSO-$d_6$).

FIG. 54 shows the $^1$H NMR spectrum of the PEG-dicrotonate. The hydroxyl protons at δ=4.55 ppm from the HO-PEG-OH completely disappeared and the peak corresponding to the methylene protons adjacent to hydroxyl group shifted downfield from δ=3.50 to δ=4.30 ppm (c) after the reaction. The new peaks corresponding to the methyl [δ=1.71 ppm (g)] and vinyl [δ=6.82 ppm (f) and δ=5.90 ppm (e)] protons of the crotonate group were observed at the expected positions with integral values of 2:1:1:3 [(c):(e):(f):(g)] confirming successful functionalization.

Figure 55:
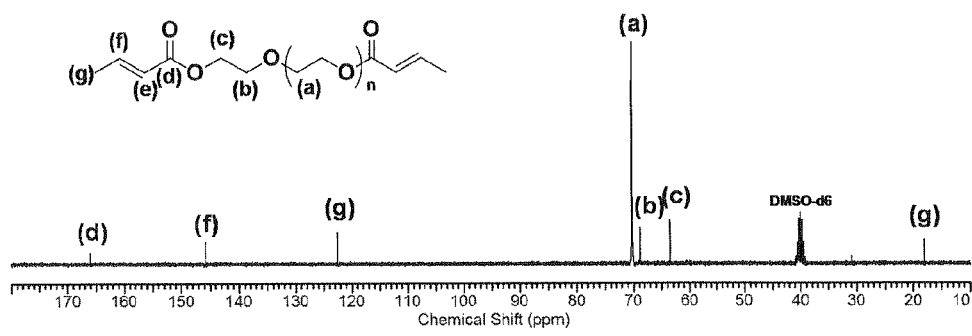
FIG. 55 shows the $^{13}$C NMR spectrum of the PEG-dicrotonate in bulk after 4 hours of reaction time (NMR solvent: DMSO-$d_6$).

The $^{13}$C NMR spectrum of the PEG-dicrotonate product is shown in FIG. 55 and also confirmed the structure of the polymer. The carbons connected to the hydroxyl group in the starting material at δ=60.13 ppm shifted downfield to δ=63.89 ppm (c) after the reaction and the carbon resonances of the crotonate group appeared at δ=166.13 ppm (d), δ=17.20 ppm (g), δ=145.85 ppm (f) and δ=122.77 ppm (g) corresponding to carbonyl carbon, α-carbon, β-carbon and the methyl carbon connected to the β-carbon, respectively.

Figure 56:
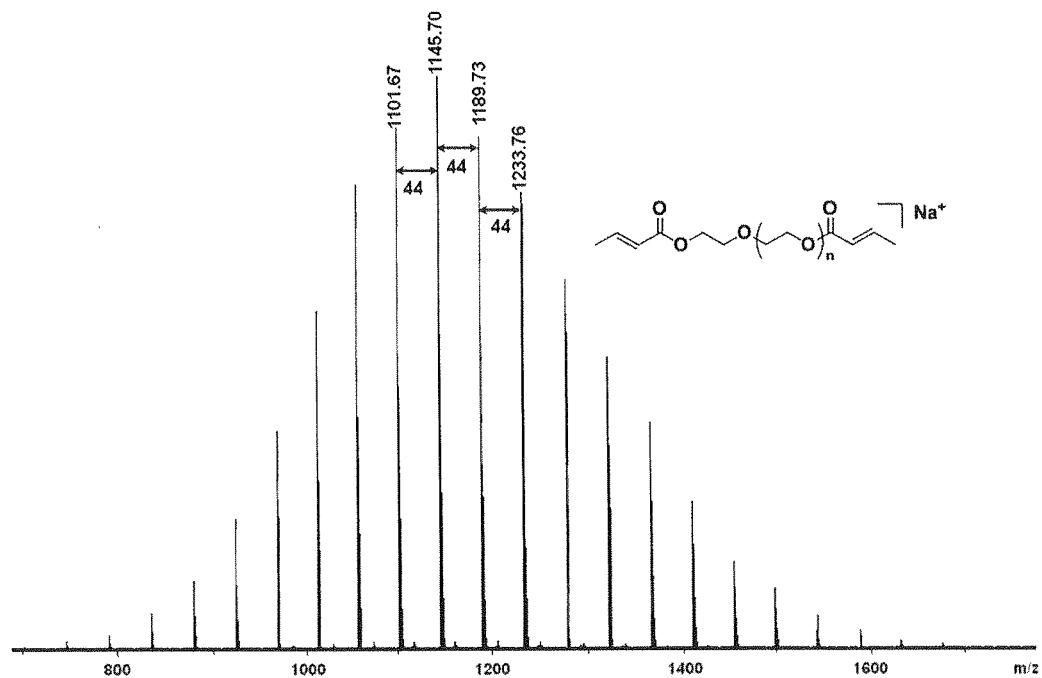
FIG. 56 shows the MALDI-ToF mass spectrum of the PEG-dicrotonate product (cationizing salt: sodium trifluoroacetate).
Figure 57:
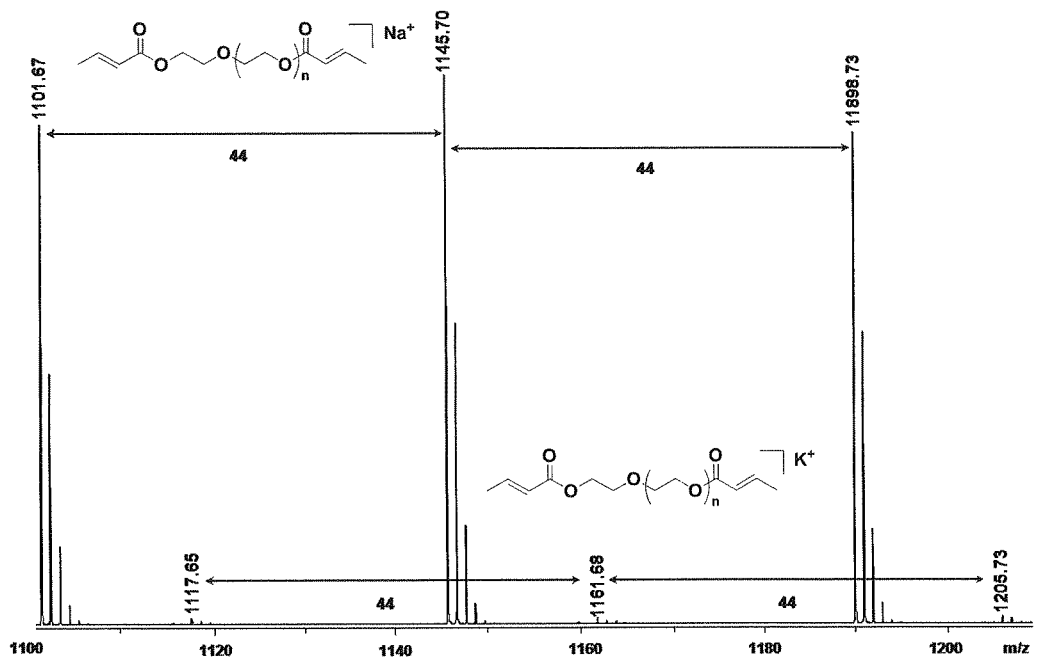
FIG. 57 shows the magnification of MALDI-ToF mass spectrum of the PEG-dicrotonate product (cationizing salt: sodium trifluoroacetate).

In MALDI-ToF mass spectrum a single product with the expected structure was observed as indicated in FIG. 56. For example, the peak at m/z 1101.67 corresponds to the sodium complex of the 21-mer of PEG-dicrotonate. The calculated monoisotopic mass for this peak is [21×44.03 ($C_2H_4O$ repeat unit)+154.08 ($C_8H_{10}O_3$ end groups)+22.99 (Na$^+$)] 1101.70 Da. Within the series the peaks were separated by m/z 44, corresponding to an ethylene glycol repeating unit. Upon a closer examination, a minor distribution of peaks which differ from the main series by 16 m/z units were observed (FIG. 57). This can be attributed to the K$^+$ cationized PEG-dimethacrylate as it is known that K$^+$ contamination could occur during sample preparation and the mass difference between Na$^+$ and K$^+$ is 16 amu.

Figure 58:
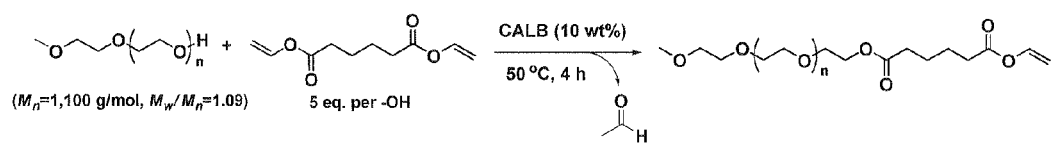
FIG. 58 shows a scheme for the transesterification of divinyl adipate with MPEG-OH in bulk according to a further example of the invention.

In another example, the synthesis of MPEG-vinyl adipate by transesterification of divinyl adipate (DVA) with poly(ethylene glycol) monomethyl ether (MPEG-OH) in bulk is shown in FIG. 58. In this scheme, 1.0 g of MPEG-OH (0.909 mmol, $M_n$=1100 g/mol, $M_w/M_n$=1.09) was dissolved in 0.901 g of DVA (4.545 mmol, ~5 eq per —OH). 100 mg of CALB (~10 wt % compared to MPEG-OH) was added in the reactant, followed by purging it with Ar gas. The reaction was stirred for 4 hours at 50° C. The liquid product was dissolved in 5 mL of THF and the CALB was filtered out using 0.45 μm syringe filter. The product solution was precipitated in 200 mL of hexane and diethyl ether mixture (1:1 ratio). The white precipitate was collected and dried using vacuum pump.

Figure 59:
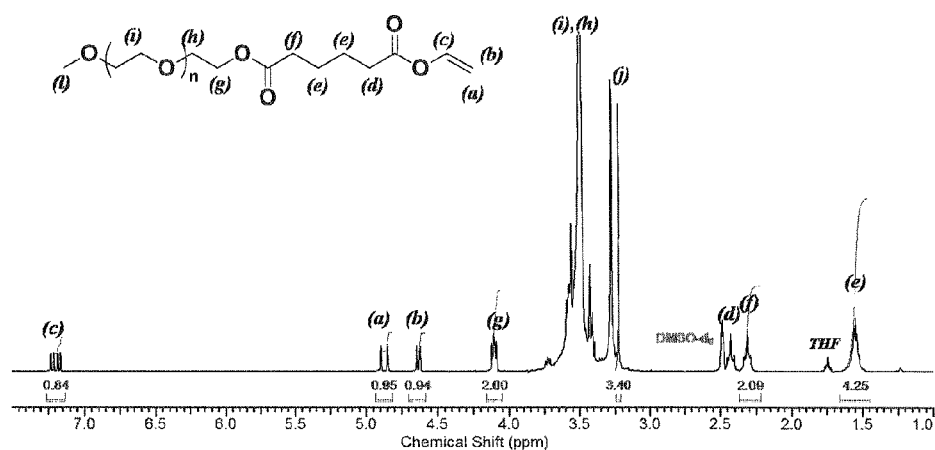
FIG. 59 shows the $^1$H NMR spectrum of the MPEG-vinyl adipate in bulk after 4 hours of reaction time (NMR solvent: DMSO-$d_6$).

The $^1$H NMR spectrum of the PEG-vinyl adipate is shown in FIG. 59. The hydroxyl protons at δ=4.55 ppm from the MPEG-OH completely disappeared and the peak corresponding to the methylene protons adjacent to hydroxyl group shifted downfield from δ=3.50 to δ=4.11 ppm (g) after the reaction. The new peaks corresponding to vinyl [δ=4.87 ppm (a), δ=4.64 ppm (b) and δ=7.18 ppm (c)] protons of the vinyl ester group were observed at the expected positions with integral values of 2:1:1:1 [(g):(a):(b):(c)] confirming successful functionalization.

Figure 60:
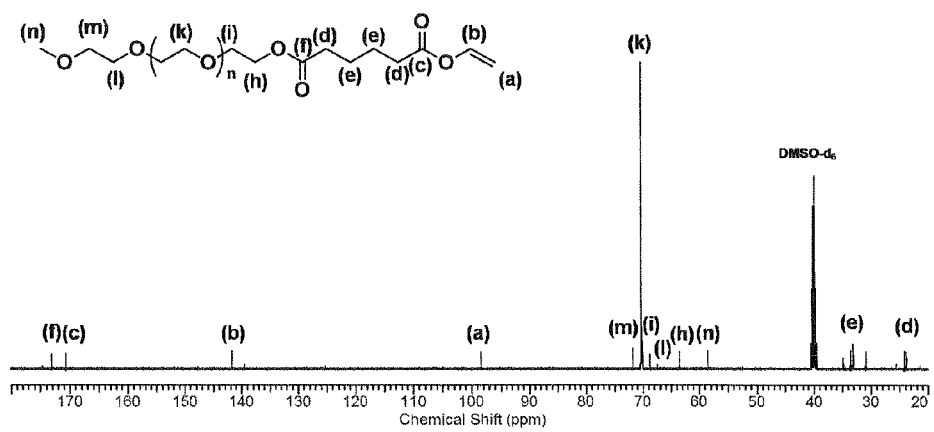
FIG. 60 shows the $^{13}$C NMR spectrum of the MPEG-vinyl adipate in bulk after 4 hours of reaction time (NMR solvent: DMSO-$d_6$).

The $^{13}$C NMR spectrum of the MPEG-vinyl adipate product is shown in FIG. 60 and also confirmed the structure of the polymer. The carbons connected to the hydroxyl group in the starting material at δ=60.13 ppm shifted downfield to δ=63.47 ppm (h) after the reaction and the carbon resonances of the vinyl ester group appeared at δ=98.22 ppm (a), δ=141.49 ppm (b), δ=170.25 ppm (c) and δ=173.05 ppm (f) corresponding to carbonyl carbon, β-carbon, α-carbon and the carbonyl carbon at the chain end and the middle of product, respectively.

Figure 61:
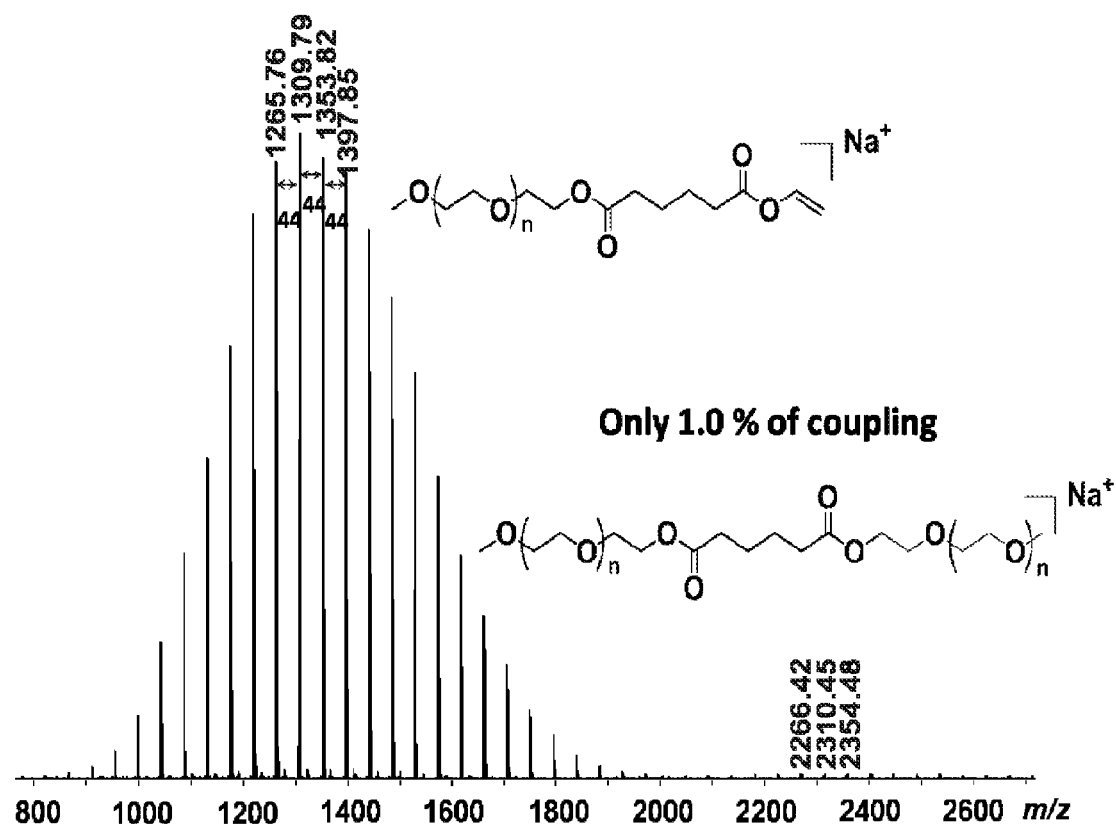
FIG. 61 shows the MALDI-ToF mass spectrum of the MPEG-vinyl adipate product (cationizing salt: sodium trifluoroacetate).

A spectrum with only 1.0% of coupled product was observed as indicated in FIG. 61. For example, the peak at m/z 1309.79 corresponds to the sodium complex of the 25-mer of MPEG-vinyl adipate. The calculated monoisotopic mass for this peak is [25×44.03 ($C_2H_4O$ repeat unit)+186.01

Figure 62:
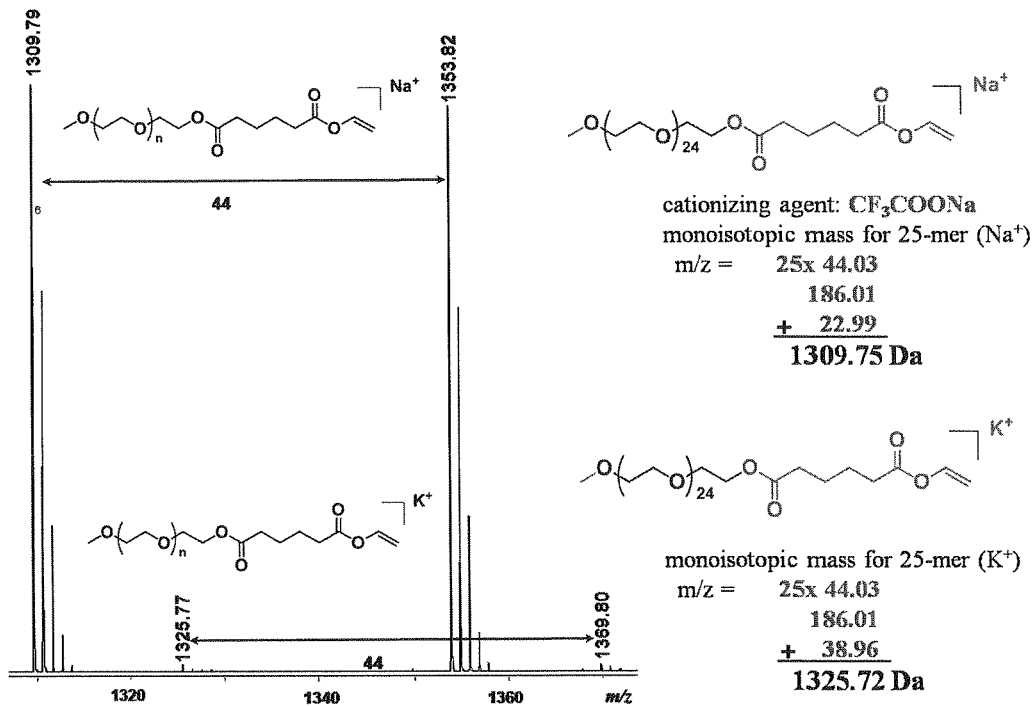
FIG. 62 shows the magnification of MALDI-ToF mass spectrum of the PEG-vinyl adipate product (cationizing salt: sodium trifluoroacetate).

($C_9H_{14}O_4$ end groups)+22.99 ($Na^+$)] 1309.75 Da. Within the series the peaks were separated by m/z 44, corresponding to an ethylene glycol repeating unit. Upon a closer examination, a minor set of peaks which differ from the main series by 12 m/z units were observed (FIG. 62).

Figure 63:
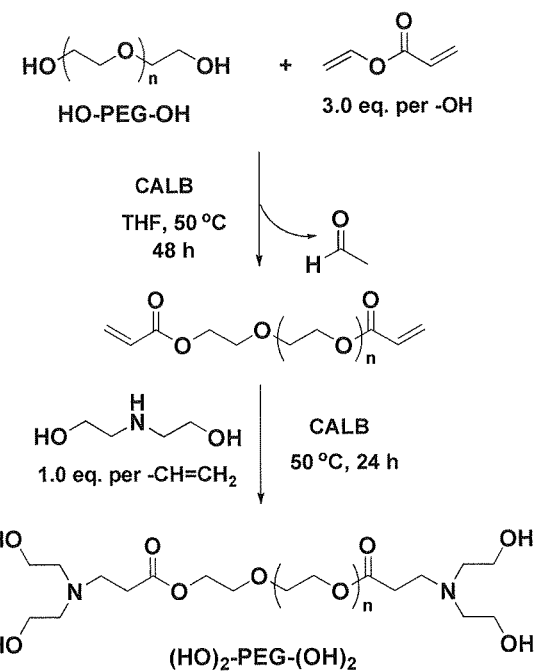
FIG. 63 shows a scheme for the synthesis of (HO)$_2$-PEG-(OH)$_2$ as a dendrimer core using CALB according to a further example of the invention.
Figure 64:
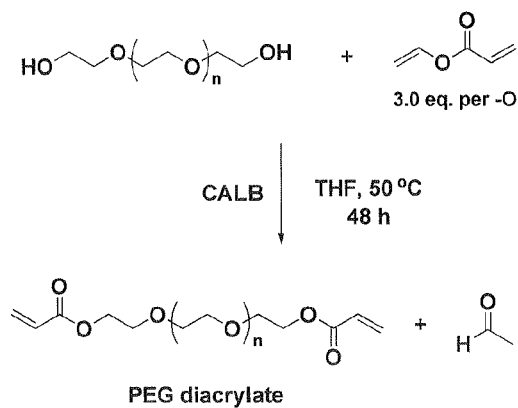
FIG. 64 shows a scheme for the transesterification of vinyl acrylate with HO-PEG-OH in THF using CALB according to a further example of the invention.

In a further example of the invention, the synthesis of PEG dendrimers is described. For example, the synthesis of (HO)$_2$-PEG-(OH)$_2$ as a dendrimer core using CALB is shown in FIG. 63. Another scheme for synthesis of PEG diacrylate is shown in FIG. 64. To synthesize PEG diacrylate, 2 g of HO-PEG-OH (1.905 mmol, 1M, $M_n$=1,050 g/mol, PDI=1.08, Polymer Source Inc.) was dissolved in 0.95 mL of dried THF (Na/Benzophenone). 64 mg of CALB (0.4 mM) was added into the PEG solution. Then 1.122 g of vinyl acrylate (11.43 mmol, 3.0 eq. per —OH) was added into the reaction. It was purged with $N_2$ for 5 min. The reaction was stirred for 48 hours at 50° C. The CALB was filtered out using 0.45 μm syringe filter. The solution was precipitated in 150 mL of hexane followed with washing it using diethyl ether. The yellowish product was dried in vacuum oven for further analysis.

Figure 65:
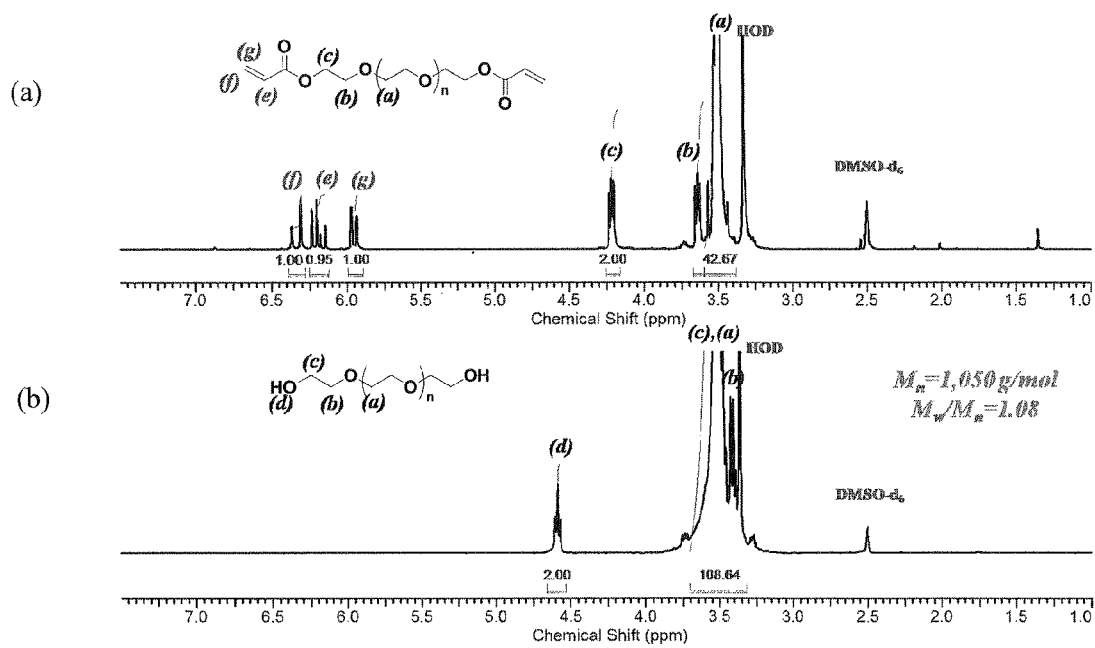
FIG. 65 shows the $^1$H NMR spectrum of HO-PEG-OH (b) and the PEG diacrylate (a) in THF after 48 hours of reaction time (NMR solvent: DMSO-$d_6$).
Figure 66:
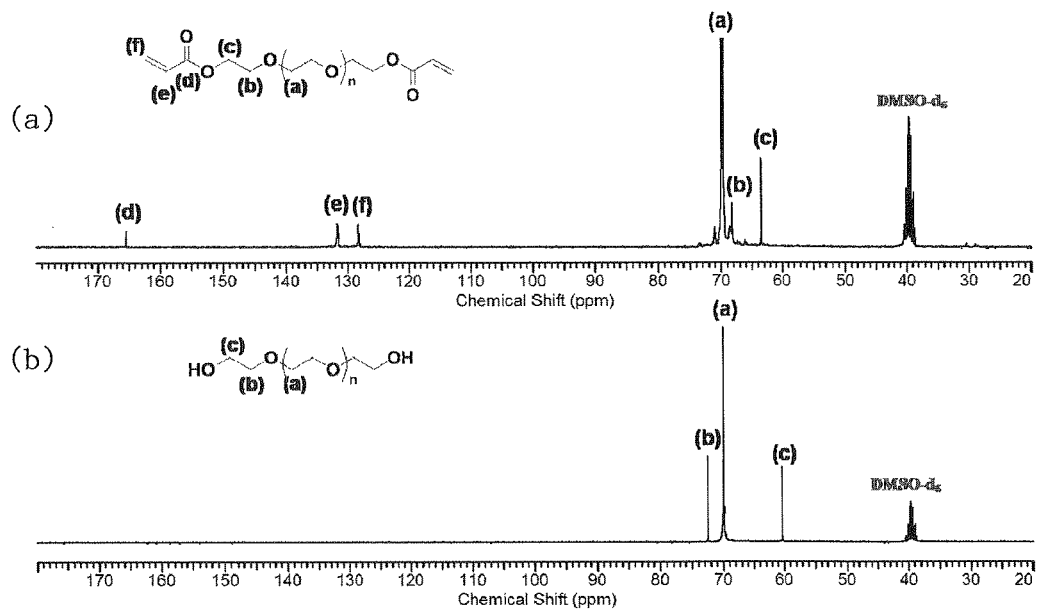
FIG. 66 shows the $^{13}$C NMR spectrum of HO-PEG-OH (b) and the PEG diacrylate (a) in THF after 48 hours of reaction time (NMR solvent: DMSO-$d_6$).

In FIG. 65, the $^1$H NMR spectra for the PEG diacrylate is shown. The —OH group (d) in HO-PEG-OH completely disappeared and acrylate group (e, f, g) appeared on 5.8-6.4 ppm. —$CH_2$— (c) in PEG was shifted from 3.5 ppm to 4.2 ppm. In the $^{13}$C NMR shown in FIG. 66, the carbon near to —OH at δ=60 ppm was completely shifted to δ=63.5 ppm and new carbon resonances corresponding to acrylate group (d, e, f) appeared.

Figure 67:
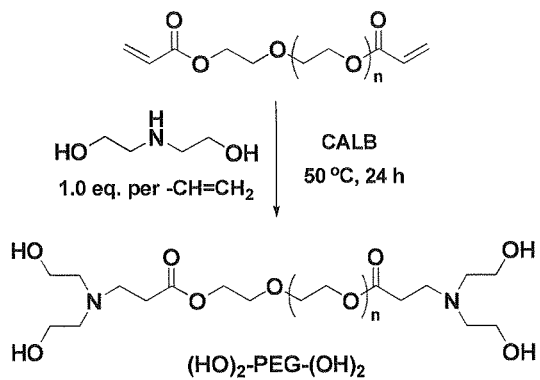
FIG. 67 shows a scheme representing the Michael addition of PEG-diacrylate with diethanolamine in DMSO using CALB according to an example of the invention.

In another example, the synthesis of (HO)$_2$-PEG-(OH)$_2$ in DMSO using CALB is shown in FIG. 67. To synthesize (HO)$_2$-PEG-(OH)$_2$, 0.124 g of PEG diacrylate (0.108 mmol, 0.1 M) was dissolved in 1 mL of anhydrous DMSO. 18 mg of CALB was added into the solution. 0.023 g of diethanolamine (0.215 mmol, 1 eq. per —CH=$CH_2$) was added into the reaction. The solution was purged with $N_2$ for 5 min. The reaction was stirred for 24 hours at 50° C. The CALB was removed and washed with THF. The excess diethanolamine and DMSO was removed using vacuum pump at 70° C. for 3 hours. The viscous product was dissolved in THF, and then precipitated in 50 mL of hexane, followed by diethyl ether. The white product was dried using vacuum oven for further analysis.

Figure 68:
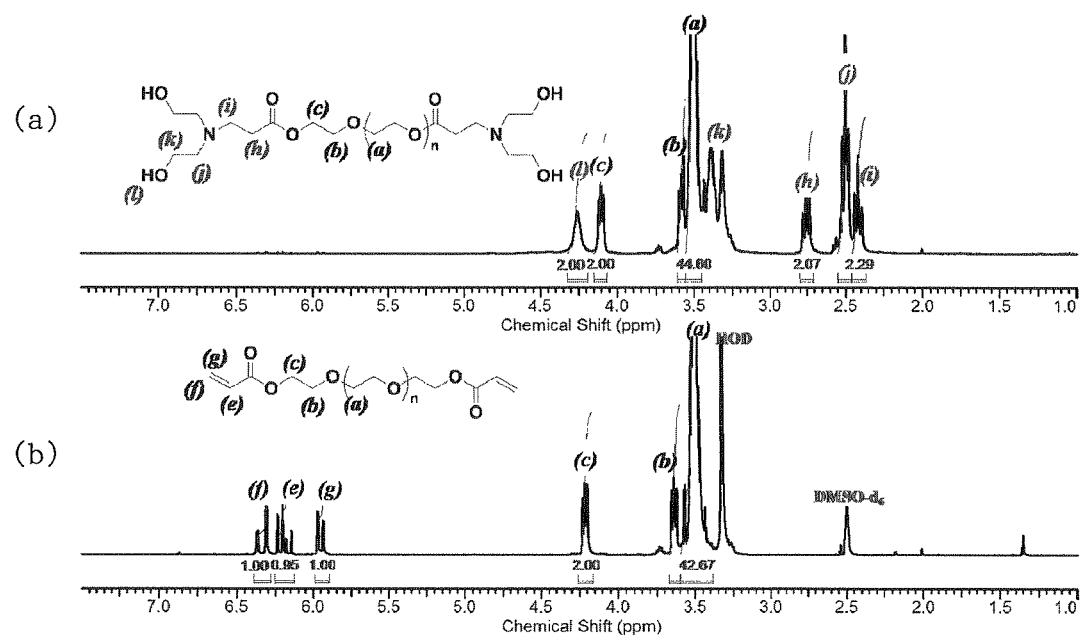
FIG. 68 shows the $^1$H NMR spectrum of PEG diacrylate (b) and (HO)$_2$-PEG-(OH)$_2$ (a) in THF after 24 hours of reaction time (NMR solvent: DMSO-$d_6$).

The $^1$H NMR spectra of PEG diacrylate and (HO)$_2$-PEG-(OH)$_2$ are shown in FIG. 68(b) and FIG. 68(a), respectively. The 99.5% of peaks corresponding to the methine [δ=6.19 ppm (e)] and vinyl [δ=6.38 ppm (f) and δ=5.92 ppm (g)] protons of the acrylate group disappeared and the peak corresponding to the methylene protons adjacent to acrylate group shifted upfield from δ=4.23 to δ=4.12 ppm (c) after the reaction. The new peaks corresponding to product [δ=4.25 ppm (l), δ=2.75 ppm (h) and δ=2.41 ppm (i)] protons were observed at the expected positions with integral values of 2:2:2 [(l):(c):(h)].

Figure 69:
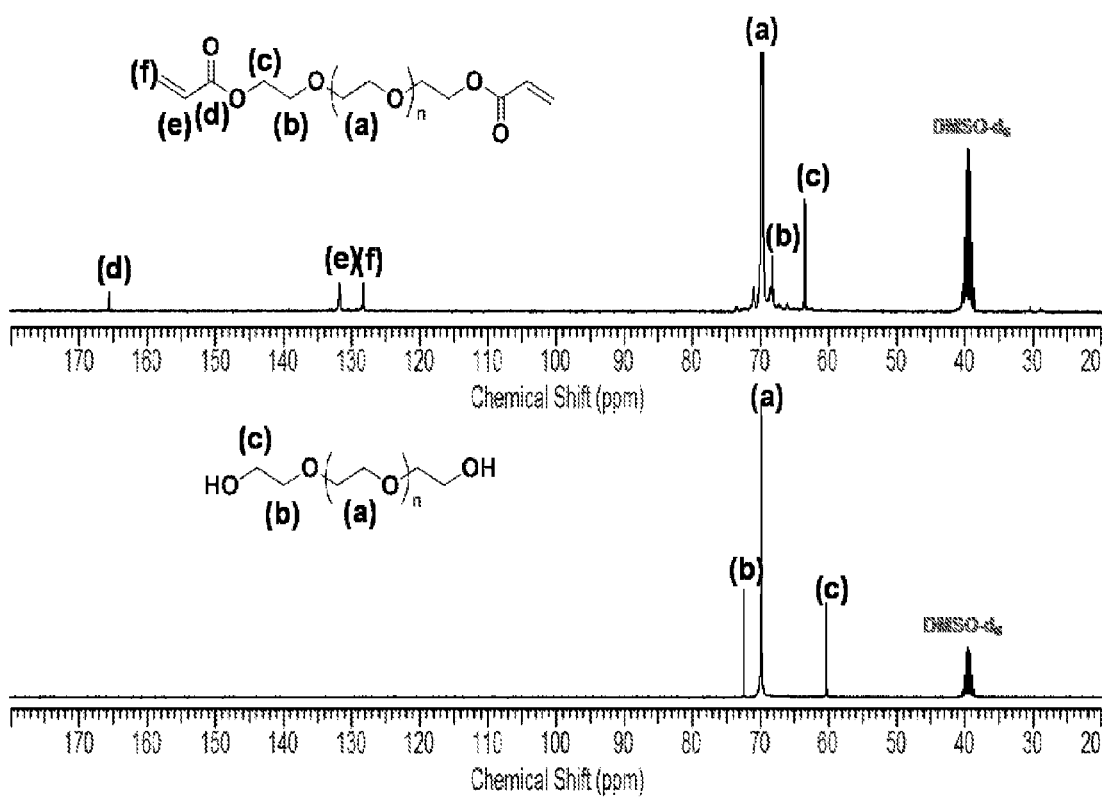
FIG. 69 shows the $^{13}$C NMR spectrum of PEG diacrylate at (b) and (HO)$_2$-PEG-(OH)$_2$ at (a) in THF after 24 hours of reaction time (NMR solvent: DMSO-$d_6$).
Figure 70:
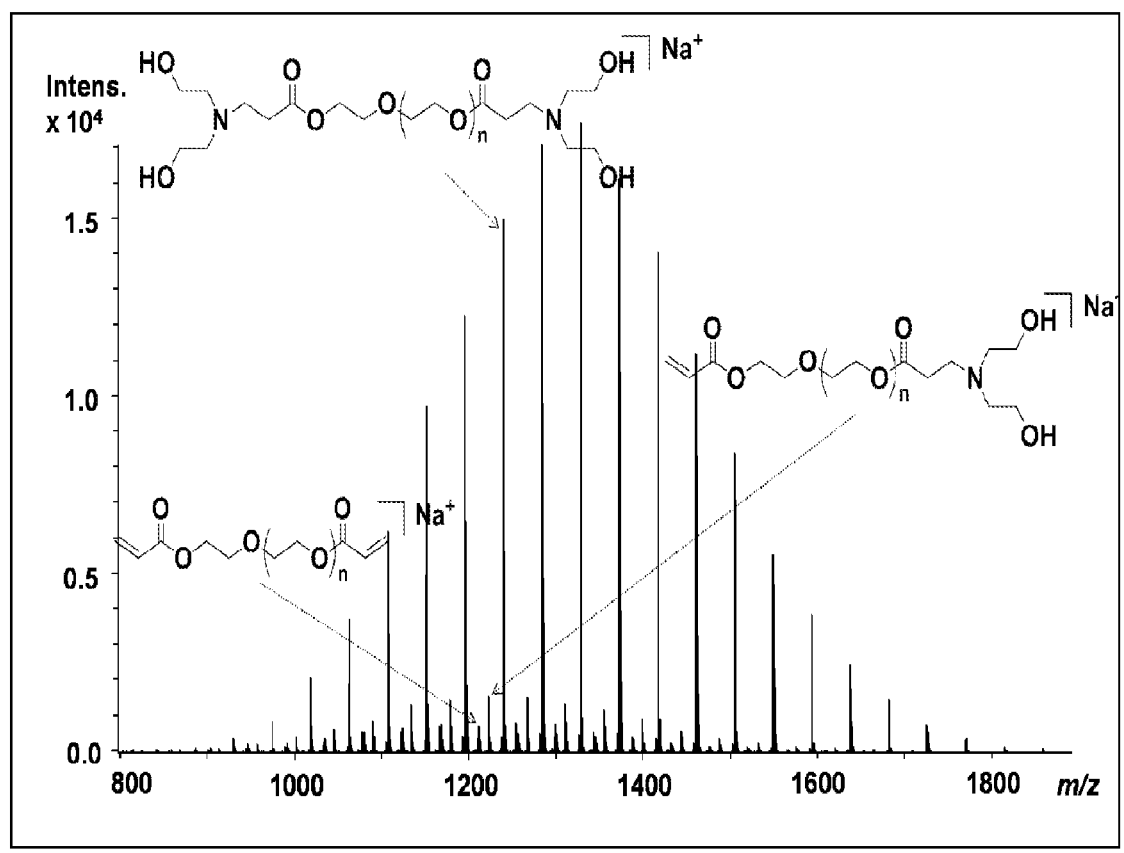
FIG. 70 shows the MALDI-ToF mass spectrum of the (HO)$_2$-PEG-(OH)$_2$ product (cationizing salt: sodium trifluoroacetate).

The $^{13}$C NMR spectrum of the (HO)$_2$-PEG-(OH)$_2$ as shown in FIG. 69 also confirmed the structure of the polymer (FIG. 20). the carbon resonances of the acrylate group at δ=165.87 ppm (d), δ=132.01 ppm (e) and δ=128.66 ppm (f) corresponding to carbonyl carbon, α-carbon and the vinyl carbons connected to the α-carbon completely shifted to δ=172.64 ppm (d), δ=32.23 ppm (e) and δ=50.01 ppm (f), respectively. The carbons connected to the hydroxyl group appeared at δ=59.77 ppm (h) and δ=56.31 ppm (g) after the reaction. MALDI-ToF mass spectrum of the (HO)$_2$-PEG-(OH)$_2$ product showed the three distributions as described in FIG. 70. The desired product, (HO)$_2$-PEG-(OH)$_2$, comprised 91% of the mixture and the two minor distributions corresponded to mono-functional PEG-acrylate (6%) and the starting material (3%).

Figure 71:
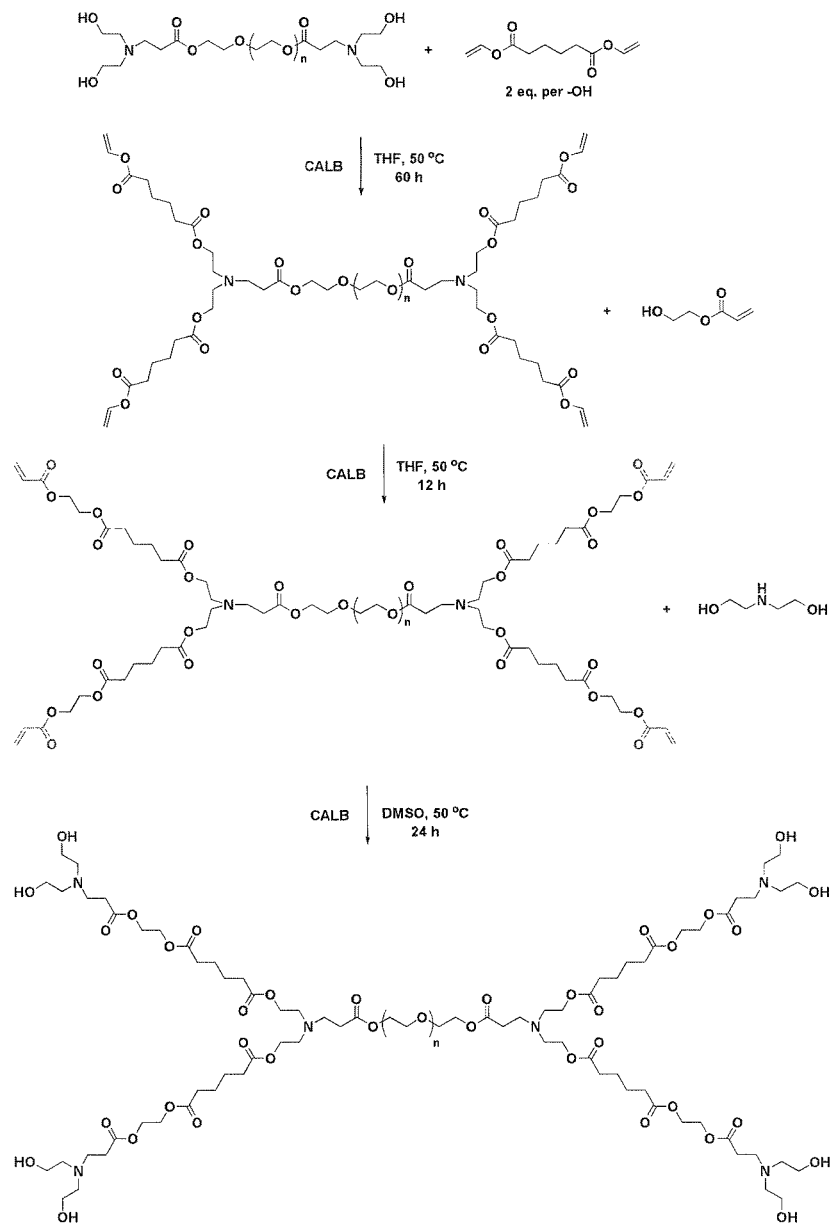
FIG. 71 shows a scheme of synthesis of (HO)$_4$-PEG-(OH)$_4$ as 2$^{nd}$ generation PEG dendrimer using CALB according to a further example of the invention.

In another example, the synthesis of (HO)$_4$-PEG-(OH)$_4$ as $2^{nd}$ generation PEG dendrimer using CALB is shown in FIG. 71. The PEG dendrimer can be prepared by the same sequences of transesterification and Michael addition with (HO)$_2$-PEG-(OH)$_2$ using enzyme catalyst as those processes were already proven in tetraethylene glycol dendrimer as a model reaction. To prepare the PEG dendrimer, (HO)$_2$-PEG-(OH)$_2$ is reacted with 2 equivalents of DVA per —OH of the polymer via transesterification generating the PEG tetravinyl ester. PEG tetraacrylate can be prepared by transesterification of 2-hydroxylethyl acrylate with PEG tetravinyl ester in the presence of CALB. Finally, (HO)$_4$-PEG-(OH)$_4$ as $2^{nd}$ generation PEG dendrimer can be synthesized by Michael addition of diethanolamine with acrylate groups on PEG. By repeating these reaction sequences, higher generation of PEG dendrimer can be established.

In the foregoing examples, the MALDI-ToF mass spectra were acquired on a Bruker Ultraflex-III ToF/ToF mass spectrometer (Bruker Daltonics, Inc., Billerica, Mass.) equipped with a Nd:YAG laser (355 nm). All spectra were measured in positive reflector mode. The instrument was calibrated prior to each measurement with an external PMMA standard. For example, individual solutions of PEG dimethacrylate (10 mg/mL), 1,8,9-trihydroxyanthracene (dithranol, 20 mg/mL, 97%, Alfa Aesar), and sodium trifluoroacetate (NaTFA, 10 mg/mL) in anhydrous THF were mixed in the ratio of polymer:matrix:cationizing salt (1:10:2), and 0.5 μL of the resulting mixture were deposited on microtiter plate wells (MTP 384-well ground steel plate). After evaporation of the solvent, the plate was inserted into the MALDI source. The attenuation of the Nd:YAG laser was adjusted to minimize unwanted polymer fragmentation and to maximize the sensitivity.

Based upon the foregoing disclosure, it should now be apparent that the method of preparing functionalized polymers through enzymatic catalysis as described herein will carry out the objects set forth hereinabove. It is, therefore, to be understood that any variations evident fall within the scope of the claimed invention and thus, the selection of specific component elements can be determined without departing from the spirit of the invention herein disclosed and described.

What is claimed is:

1. A method of preparing a functionalized polymer through enzymatic catalysis, the method comprising the steps of:
    reacting a polymer with at least one acyl donor selected from the group consisting of vinyl acrylate and vinyl (meth)acrylate in the presence of an enzymatic catalyst in a transesterification reaction to produce a transesterification reaction product; and
    thereafter reacting the transesterification reaction product with a nucleophile in the presence of an enzymatic catalyst in a Michael Addition reaction.

2. The method of claim 1, wherein the polymer is a glycol ether.

3. The method of claim 2, wherein the glycol ether is selected from the group consisting of poly(ethylene glycol), poly(ethylene glycol) monomethyl ether and aminoethoxy polyethylene glycol monomethyl ether.

4. The method of claim 1, wherein the polymer is a polysiloxane.

5. The method of claim 4, wherein the polysiloxane is polydimethylsiloxane.

6. The method of claim 1, wherein the polymer is a hydroxy-functionalized polyisobutylene.

7. The method of claim 1, wherein the enzyme catalyst is *Candida Antarctica* lipase B.

8. The method of claim 1, wherein the at least one acyl donor renders the transesterification reaction substantially irreversible.

9. The method of claim 8, wherein the transesterification reaction is rendered substantially irreversible through formation of an unstable enol which tautomerizes to an acetaldehyde.

10. A method of preparing a telechelic polymer through enzymatic catalysis, the method comprising the steps of:
    reacting a glycol ether with at least one ester selected from the group consisting of vinyl acrylate and vinyl (meth) acrylate in the presence of an effective amount of a lipase in a transesterification reaction to produce a transesterification reaction product; and
    thereafter reacting the transesterification reaction product with a nucleophile in the presence of an enzymatic catalyst in a Michael Addition reaction.

11. The method of claim 10, wherein the glycol ether is poly(ethylene) glycol poly(ethylene glycol) monomethyl ether and aminoethoxy polyethylene glycol monomethyl ether.

12. The method of claim 11, wherein the glycol ether is aminoethoxy polyethylene glycol monomethyl ether.

13. The method of claim 10, wherein the lipase is *Candida antarctica* lipase B.

14. The method of claim 10, wherein the transesterification reaction is irreversible.

15. The method of claim 1, wherein the nucleophile is selected from an aminoethoxy glycol ether and thymine.

16. The method of claim 15, wherein the nucleophile is aminoethoxy polyethylene glycol monomethyl ether.

17. The method of claim 10, wherein the nucleophile is selected from an aminoethoxy glycol ether and thymine.

18. The method of claim 17, wherein the nucleophile is aminoethoxy polyethylene glycol monomethyl ether.

* * * * *